US006262241B1

United States Patent
Cook et al.

(10) Patent No.: US 6,262,241 B1
(45) Date of Patent: Jul. 17, 2001

(54) COMPOUND FOR DETECTING AND MODULATING RNA ACTIVITY AND GENE EXPRESSION

(75) Inventors: Phillip Dan Cook; David J. Ecker, both of Carlsbad; Charles John Guinosso, Vista; Oscar Leobardo Acevedo, San Diego; Andrew Kawasaki, Oceanside; Kandasamy Ramasamy, Laguna Hills, all of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/383,666

(22) Filed: Feb. 3, 1995

Related U.S. Application Data

(62) Continuation of application No. 07/854,634, filed on Jul. 1, 1992, now abandoned, which is a continuation-in-part of application No. 07/463,358, filed as application No. PCT/US91/00243 on Jan. 11, 1991, now abandoned, which is a continuation-in-part of application No. 07/566,977, filed on Aug. 13, 1990, now abandoned.

(51) Int. Cl.[7] .............................. C12Q 1/68; C07H 21/02; C07H 21/04
(52) U.S. Cl. ................................ 536/22.1; 435/5; 435/6; 436/501; 514/44; 536/25.3
(58) Field of Search ................... 435/5, 6, 172.3, 435/810; 436/501; 514/44; 536/22.1, 23.1, 25.3; 935/77, 78

(56) References Cited

U.S. PATENT DOCUMENTS

| | | | | |
|---|---|---|---|---|
| 4,381,344 | * | 4/1983 | Rideout et al. | 435/87 |
| 4,511,713 | | 4/1985 | Miller et al. | 536/27 |
| 4,547,569 | | 10/1985 | Letsinger et al. | 536/29 |
| 4,689,320 | * | 8/1987 | Kaji | 514/44 |
| 4,719,295 | * | 1/1988 | Cook et al. | 536/26 |
| 4,760,017 | * | 7/1988 | McCormick | 435/6 |
| 4,795,700 | * | 1/1989 | Dervan et al. | 435/5 |
| 4,876,335 | * | 10/1989 | Yamane et al. | 536/27 |
| 4,965,350 | * | 10/1990 | Inoue et al. | 536/28 |
| 5,013,830 | | 5/1991 | Ohtsuka et al. | 536/27 |
| 5,212,295 | * | 5/1993 | Cook | 536/26.7 |
| 5,214,135 | | 5/1993 | Srivastava et al. | 536/26.7 |
| 5,359,051 | * | 10/1994 | Cook et al. | 536/26.7 |
| 5,466,786 | * | 11/1995 | Buhr et al. | 536/26.26 |
| 5,914,396 | * | 6/1999 | Cook et al. | 536/26.1 |

FOREIGN PATENT DOCUMENTS

| | | |
|---|---|---|
| 3010399 | * 9/1981 | (DE) . |
| 4110085 | 10/1992 | (DE) . |
| 0017465 | 10/1980 | (EP) . |
| 0085440 | * 8/1983 | (EP) . |
| 0260032 | * 3/1988 | (EP) . |
| 0266099 | 5/1988 | (EP) . |
| 0 269 574 A2 | 6/1988 | (EP) . |
| 0286028 | * 10/1988 | (EP) . |
| 0329348 | 8/1989 | (EP) . |
| 0 339 842 A2 | 11/1989 | (EP) . |
| 0393920 | * 10/1990 | (EP) . |
| 20-00277 | 1/1990 | (JP) . |
| WO 91/10671 | 7/1991 | (WO) . |

OTHER PUBLICATIONS

Marcus–Sekura (1988) Anal. Bioch., vol. 172, pp. 289–295.*

Agarwal, K.L. and Riftina, "Synthesis and Enzymatic Properties of Deoxyribooligonucleotides Containing Methyl and Phenylphosphonate Linkages", *Nucleic Acids Research* 1979, 6, 3009–3024.

Agrawal, S. et al., "Oligodeoxynucleoside Phosphoramidates and Phosphorothioates as Inhibitors of Human Immunodeficiency Virus" *PNAS USA* 1988, 85, 7079–7083.

Agris, C.H. et al., "Inhibition of Vesicular Stomatitis Virus Protein Synthesis and Infection by Sequence–Specific Oligodeoxyribonucleoside Methylphosphonates", *Biochemistry* 1986, 25, 6268–6275.

Arnott and Hukins, "Optimised Parameters for A–DNA and B–DNA" *Biochemical and Biophysical Research Communication* 1972, 47, 1504–1510.

Beaucage, S. et al., "Deoxynucleoside phosphoramidites—A new class of key intermediates for deoxypolynucleotide synthesis", *Tetrahedron Letters* 1981, 22, 1859–1862.

Bhat, V. et al., "A Simple and Convenient Method for the Selective N–Acylations of Cytosine Nucleosides", *Nucleosides and Nucleotides* 1989, 8, 179–183.

Biggadike, K. et al., "Short convergent route to homochiral carbocyclic 2′-deoxynucleosides and carbocyclic robonucleosides", *J. Chem. Soc., Chem. Commun.* 1987, 1083–1084.

Brill, W. et al., "Synthesis of Deoxydinucleoside phosphorodithioates", *Journal of the American Chemical Society* 1991, 113, 3972–3980.

Butke, G. et al., in "Nucleic Acid Chemistry," Part 3, pp. 149–152, Townsend, L.B. and Tipson, eds., J. Wiley and Sons, New York, 1986.

(List continued on next page.)

*Primary Examiner*—Ardin H. Marschel
(74) *Attorney, Agent, or Firm*—Woodcock Washburn Kurtz Mackiewicz & Norris LLP

(57) ABSTRACT

Compositions and methods for modulating the activity of RNA and DNA are disclosed. In accordance with preferred embodiments, antisense compositions are prepared comprising targeting and reactive portions. Reactive portions which act, alternatively, through phosphorodiester bond cleavage, through backbone sugar bond cleavage or through base modification are preferably employed. Groups which improve the pharmacodynamic and pharmacokinetic properties of the oligonucleotides are also useful in accordance with certain embodiments of this invention. Delivery of the reactive or non-reactive functionalities into the minor groove formed by the hybridization of the composition with the target RNA is also preferably accomplished. Therapeutics, diagnostics and research methods and also disclosed. Synthetic nucleosides and nucleoside fragments are also provided useful for elaboration of oligonucleotides and oligonucleotide analogs for such purposes.

29 Claims, No Drawings

OTHER PUBLICATIONS

Caruthers, M., "Oligonucleotides. Antisense Inhibitors of Gene Expression", Cohen, J.S., ed., pp. 7–24, CRC Press, Inc., Boca Raton, FL 1989.

Castle, R., "Imidazo[4,5–d]pyridazines. I. Synthesis of 4,7–Disubstituted Derivatives", *Journal of Organic Chemistry* 1958, 23, 1534–1538.

Cazenave et al., "Enzymatic Amplification of Translation Inhibition of Rabbit β–globin mRNA Mediated by Anti–Messenger Oligodeoxynucleotides Covalently Linked to Intercalating Agents", *Nucleic Acid Research* 1987, 15, 4717–4736.

Chen, Y. and Wu, "Studies on Fluoroalkylation and Fluoralkoxylation. Part 33. Direct Trifluoromethylation of Aryl Halides with Fluorosulphonyldifluoromethyl Iodide in the Presence of Copper: an Electron Transfer Induced Process", *Journal of Chemical Society Perkin Transactions* 1989, 2385–2387.

Butke et al., "Facile Synthesis of 2'–Amino–2'–Deoxyadenosine", *Journal of Carbohydrates, Nucleosides & Nucleotides* 1980, 7, 63–75.

Cohen, "Oligonucleotides: Antisense Inhibitors of Gene Expression", CRC Press, Inc., Boca Raton, FL, 1989.

Constant, J.F. et al., "Heterodimeric Molecules Including Nucleic Acid Bases and 9–Aminoacridine Spectroscopic Studies, Conformations, and Interactions with DNA" *Biochemistry* 1988, 27, 3997–4003.

Cook et al., "Synthesis and Antiviral and Enzymatic Studies of Certain 3–Deazaguanines and Their Imidazolecarboxamide Precursors", *Journal of Medicinal Chemistry* 1978, 21, 1212–1218.

Daves, G. and Cheng, "The Chemistry and Biochemistry of C–Nucleosides", *Progress in Medicinal Chemistry* 1976, 13, 304–349.

Calvo, Mateo et al., "3'–C–Cyano–3'–Deoxythymidine", *Tetrahedron Letters* 1988, 29, 941–944.

Le Doan, P.L. et al., "Sequence–Targeted Chemical Modifications of Nucleic Acids by Complementary Oligonucleotides Covalently Linked to Porphyrins", *Nucleic Acids Research* 1987, 15, 8643–8659.

Dreyer, G. and Dervan, "Sequence–specific cleavage of single–stranded DNA: Oligodeoxynucleotide–EDTA–Fe(II)", *PNAS USA* 1985, 82, 968–972.

Hobbs et al., "Polynucleotides Containing 2'–Chloro–2'–Deoxyribose", *Biochemistry* 1972, 11, 4336–4344.

Codington et al., "Nucleosides. XVIII. Synthesis of 2'–Fluorothymidine, 2'–Fluorodeoxyuridine, and Other 2'–Halogeno–2'–Deoxy Nucleosides", *Journal of Organic Chemistry* 1964, 29, 558–564.

Freskos, J., "Synthesis of 2'Deoxypyrimidine Nucleosides Via Copper (I) Iodide Catalysis", *Nucleosides and Nucleotides* 1989, 8, 1075–1076.

Gaffney, B. and Jones, "A New Strategy for the Protection of Deoxyguanosine During Oligonucleotide Synthesis", *Tetrahedron Letters* 1982, 23, 2257–2260.

Guschlbauer, W. and Jankowski, "Nucleoside conformation is Determined by the Electronegativity of the Sugar Substituent", *Nucleic Acids Research* 1980, 8, 1421–1433.

Hertel, L.W. et al., "Synthesis of 2–Deoxy–2, 2–difluoro–D–ribose and 2–Deoxy–2,2–difluoro–D–ribofuranosyl Nucleosides", *Journal of Organic Chemistry* 1988, 53, 2406–2409.

Ikehara, M. et al., "Polynucleotides. LII.synthesis and properties of poly (2'–deox–2'–fluoroadenylic acid)", *Nucleic Acids Research* 1978, 5, 1877–1887.

Ikehara, M. et al., "Polynucleotides. LVI. Synthesis and Properties of Poly(2'–deoxy–2'–fluoroinosinic Acid", *Nucleic Acids Research* 1978, 5, 3315–3324.

Ikehara, M. et al., "A Linear Relationship Between Electronegativity of 2'–Substituents and conformaiton of Adenine Nucleosides", *Tetrahedron Letters* 1979, 42, 4073–4076.

Ohtanka et al., "Recognition by Restriction Endonuclease EcoRI of Deoxyoctanucleotides Containing Modified Sugar Moieties", *European Journal of Biochemistry* 1984, 139, 447–450.

Ikehara, M. et al., "Polynucleotides. L. synthesis and properties of poly (2'chloro–2'–deoxyandenylic acid) and poly (2'–bromo–2'–deoxyadenylic acid)", *Nucleic Acids Research* 1977, 4, 4249–4260.

Ikehara, M., "Studies of Nucleosides and Nucleotides–LXXXII.[1]) cyclonucleosides. (39).[2]) synthesis and properties of 2'halogen–2'–deoxyadenosines", *Chemistry and Pharmaceutical Bulletin* 1978, 26, 2449–2453.

Ikehara, M., "Purine 8–Cyclonucleosides", *Accounts of Chemical Research* 1969, 2, 47–53.

Ikehara, M. et al., "Studies of Nucleosides and Nucleotides–LXXIV[1]", *Tetrahedron* 1978, 34, 1133–1138.

Ikehara, M. et al, "Studies of Nucleosides and Nucleotides–LXXXIX., Purine cyclonucleosides. (43). synthesis and properties of 2'halogen–2'–deoxyguanosines[1])", *Chemical and Pharmaceutical Bulletin* 1981, 29, 3281–3285.

Vesugi et al., "Improved Synthesis of 2'–Fluoro–2'–Deoxyadenosine and Synthesis and Carbon–13 NMR Spectrum of Its 3',5'–Cyclic Phosphate Derivative", *Nucleosides and Nucleotides* 1983, 2, 373–385.

Ikehara, M. et al., "Studies of Nucleosides and Nucleotides–LXXXVII.[1]), Purine cyclonucleosides. XLII. synthesis of 2'deoxy–2'fluorofunaosine", *Chemical and Pharmaceutical Bulletin* 1981, 29, 1034–1038.

Ikehara, M., "Studies of Nucleosides and Nucleotides–LXXIX.1), Purine cyclonucleosides. (37). The total synthesis of an antibiotic 2'–amino–2'deoxyguanosine2)", *Chemistry and Pharmaceutical Bulletin* 1978, 26, 240–244.

Ikehara, M. et al., "Studies of Nucleosides and Nucleotides–LXV[1]", *Tetrahedron* 1975, 31, 1369–1372.

Inoue, H. et al., "Synthesis and hybridization studies on two complementary nona(2'–O–methyl) ribonucleotides", *Nucleic Acids Research* 1987, 15, 6131–6148.

Iyer, R., Beaucage, Serge L. et al., "3H–1, 2–benzodithiole–3–one 1,1–dioxide as an improved sulfurizing reagent in the solid–phase synthesis of oligodeoxyribonucleoside phosphorothiioates", *Journal of American Chemical Society* 1990, 112, 1253–1255.

Jager, A. et al., "Oligonucleotide N–Alkylphosphoramidates: Synthesis and Binding to Polynucleotides", *Biochemistry* 1988, 27, 7237–7246.

Jarvi, E.T. et al., "Synthesis and biological evaluation of dideoxynucleosides containing a difluoromethylene unit", *Nucleosides and Nucleotides* 1989, 8, 1111–1114.

Jayaraman, K. et al., "Selective inhibition of *escherichia coli* protein synthesis and growth by nonionic oligonucleotides omplementary to the 3' end of 16S rRNA", *PNAS USA* 1981, 78, 1537–1541.

Ti et al. "Transient protection: Efficient one–flask synthesis of protected deoxynucleosides", *J. Am. Chem. Soc.*, 1982, 104, 1316–1319.

Jones, G. et al., "4'–substituted nucleosides. 5. hydroxymethylation of nucleoside 5'–aldehydes", *J. Org. Chem.* 1979, 44, 1309–1317.

Balban, I. and Pyman, "Bromo–Derivatives of Glyoxaline", *Journal of Chemical Society* 1922, 121, 947–958.

Kazimierczuk, Z. et al., "Synthesis of 2'–deoxytubercidin, 2'–deoxyadenosine, and related 2'–deoxynucleosides via novel direct stereospecific sodium salt glycosylation procedure", *Journal of American Chemical Society* 1984, 106, 6379–6382.

Knoore, D. and Vlassov, "Complementary–Addressed (Sequence–Specific) Modificaiton of Nucleic Acids", *Progress in Nucleic Acid Research and Molecular Biology* 1985, 32, 291–320.

Koole, L. et al., "Synthesis of phosphate–methylated DNA fragments using 9–fluorenylmethoxycarbonyl as transient base protecting group", *Journal of Organic Chemistry* 1989, 54, 1657–1664.

Letsinger, R. et al., "Effects of pendant groups at phosphorus on binding properties of d–ApA analogues", *Nucleic Acids Research* 1986, 14, 3487–3499.

Loose–Mitchell, D., "Antisense Nucleic Acids as a Potential Class of Pharmaceutical Agents", *TIPS* 1988, 9, 45–47.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucleic Acid Research* 1987, 15, 5749–5763.

Markiewicz, W. and Wiewiorowski, "Nucleic Acid Chemistry", Part 3, pp. 229–231, Townsend, L. and Tipson, eds., J. Wiley and Sons, New York, 1986.

Matsukura, M. et al., "Phosphorothioate analogs of oligodeoxynucleotides: Inhibitors of replication and cytopathic effects of human immunodeficiency virus", *PNAS USA* 1987, 84, 7706–7710.

Meyer, R.B., "Efficient, Specific Cross–Linking and Cleavage of DNA by Stable, Synthetic Complementary Oligodeoxynucleotides" *Journal of the American Chemical Society* 1989, 111, 8517–8519.

Miller, P.S. and Ts'O, "A New Approach to Chemotherapy Based on Molecular Biology and Nucleic Acid Chemistry: Matagen (Masking Tape for Gene Expression", *Anti–Cancer Drug Design* 1987, 2, 117–128.

Miller, P.S. et al., "Nonionic Nucleic Acid Analogues. Synthesis and Characterization of Dideoxyribonucleoside Methylphosphonates" *Biochemistry* 1979, 18, 5134–5143.

Miller, P.S. et al., "Synthesis and Properties of Adenine and Thymine Nucleoside Alkyl Phosphotriesters, the Neutral Analogs of Dinucleoside Monophosphates", *Journal of the American Chemical Society* 1971, 93, 6657–6665.

Miller, P.S. et al., "Biochemical and Biological Effects of Nonionic Nucleic Acid Methylphosphonates", *Biochemistry* 1981, 20, 1874–1880.

Mitsunobu, "The Use of Diethyl Azodicarboxylate and Triphenylphosphine in Synthesis and Transformation of Natural Products", *Synthesis* 1981, 1–28.

Nair V., "Development of Methodologies for the Strategic Modification of Purine Ribonucleoside Systems", *Nucleosides and Nucleotides* 1989, 8, 699–708.

Damha et al. "Solution and Solid Phase Chemical Synthesis of Arabinonucleotides", *Can. J. Chem.* 1989, 67, 831–839.

Wu et al. "Prevention of Chain Cleavage in the Chemical Synthesis of 2'–silylated Oligoribonucleotides", *Nucleic Acids Research,* 1989 17, 3501–3517.

Outten R. and Daves, "Synthetic 1–methoxybenzo[d]naphtho[1,2–b]pyran–6–one c–glycosides", *Journal of Organic Chemistry* 1987, 52, 5064–5066.

Parkes, K. and Taylor, "A Short Synthesis of 3'–Cyano–3'–Deoxythymidine", *Tetrahedron Letters* 1988, 29, 2995–2996.

Pfitzner, K.E. and Moffatt, J.G., "The synthesis of nucleoside–5' aldehydes", *Journal of American Chemical Society* 1963, 85, 3027.

Ranganathan, R., "Modification of the $2^1$–Position of Purine Nucleosides: Synthesis of $2^1$–a–Substituted–$2^1$–Deoxyadenosine Analogs", *Tetrahedron Letters* 1977, 15, 1291–1294.

Stufkens, D.J., "Dynamic Jahn–Teller Effect in the Excited States of $SeCl^6{}_{2-}$, $SeBr^6{}_{2-}$, $TeCl^6{}_{2-}$ and $TeBr^6{}_{2-}$", *Rec. Trav. Chim.,* 1970, 89, 1185–1201.

Divakar et al., "4'(1,2,4–Triazol–1–yl)–and 4'(3'Nitro'1,2,4–triazol–1–yl)–1–(β–D–2,3, 5–tri–O–acetylarabinofuranosyl)pyrimidin–2(1H)–ones. Valuable Intermediates in the Synthesis of Derivatives of 1–(β–D–Arabinofuranosyl)cytosine (Ara–C)", *J. Chem. Soc. Perkin Trans I* 1982, 1171–1176.

Revankar et al., "Synthesis and Antiviral/Antitumor of Certain 3–Seazaguanine Nucleosides and Nucleotides", *Journal of Medicinal Chemistry* 1984, 27, 1389–1396.

Robins, M. et al, "Nucleic acid related compounds. 46. A general procedure for the efficient deoxygenation of secondary alcohols. Regiospecific and stereoselective conversion of ribonucleosides to 2'–deoxynucleosides", *J. Am. Chem. Soc.* 1983, 105, 4059–4065.

Hansske et al., "2'– and 3'–Ketonucleosides and their Arabino and Xylo Reduction Products" *Tetrahedron* 1984, 40, 125–135.

Roelen, HCPF, et al., "Synthesis of nucleic acid methylphos–phonothioates", *Nucleic Acid Research* 1988, 16, 7633–7645.

Ruby, S.W. and Abelson, "An early hierarchic role of U1 small nuclear ribonucleoprotein in splicesome assembly", *Science* 1988, 242, 1028–1035.

Schmidt, Richard R. et al., "C–Glycosides from O–Glycosyl Trichloroacetimidates" *Tetrahedron Letters* 1982, 23, 409–412.

Seela, F. and Kehne, "Palindromic Octa– and Dodecanucleotides Containing 2'–Deoxytubercidin: Synthesis, Hairpin Formation, and Recognition by the Endodeoxyribonuclease EcoRI", *Biochemistry* 1987, 26, 2232–2238.

Shibahara, S. et al., "Inhibition of Human Immunodeficiency Virus (HIV–1) Replication by Synthetic Oligo–RNA Derivatives", *Nucleic Acids Research* 1987, 17, 239–252.

Sigman, D., "Nuclease Activity of 1,10–Phenanthroline–Copper Ion", *Accounts of Chemical Research* 1986, 19, 180–186.

Smith, C. et al., "Antiviral effect of an oligo(nucleoside methylphosphonate) complementary to the splice junction of herpes simplex virus type 1 immediate early pre–mRNAs 4 and 5" *Proc. Nat Acad Sci,* vol. 83, pp. 2787–2791, (1986).

Sproat, B. et al., "Highly Efficient Chemical Synthesis of 2'–O–methyloligoribonucleotides and Tetrabiotinylated Derivatives; Novel Probes that are Resistant to Degradation by RNA or DNA Specific Nucleases", *Nucleic Acids Research* 1989, 17, 3373–3386.

Sproat, B.S. et al., "New synthetic routes to protected purine 2'–O–methylriboside–3'–O–phosphoramidites using a novel alkylation procedure", *Nucleic Acids Research* vol. 18, pp. 41–49, (1990).

Stein, C.A. et al., "Physicochemical properties of phosphorothioate oligodeoxynucleotides", *Nucleic Acids Research* 1988, 16, 3209–3221.

Stein, C.A. and Cohen, "Oligodeoxynucleotides as Inhibitors of Gene Expression: A Review", *Cancer Research* 1988, 48, 2659–2668.

Suciu et al., "Synthesis of 9–(2,5–dideoxy–β–D–glycero–pent–4–enofuranosyl)adenine", *Carbohydr. Res.* 1975, 44, 112–115.

Bhat, C., "2–Deoxy–3,5–di–O–p–toluoyl–D–erythro–pentosyl Chloride" in *Synthetic Procedures in Nucleic Acid Chemistry* 1968, vol. 1, Zorbach, ed., Interscience pp. 521–522.

Tidd, D.M. et al., "Evaluation of N–ras oncogene anti–sense, sense and nonsense sequence methylphosphonate oligonucleotide analogues", *Anti–Cancer Drug Design,* 3, pp. 117–127, (1988.

Van der Krol, A.R. et al., "Modulation of Aukaryotic Gene Expression by Complementary RNA or DNA Sequences", *BioTechniques* 1988, 6, 958–973.*

Walder, R. and Walder, "Role of RNase H in hybrid–arrested translation by antisense oligonucleotides", *PNAS USA* 1988, 85, 5011–5015.*

Walder, J., "Antisense DNA and RNA: Progress and Prospects" *Genes and Development* 1988, 2, 502–504.*

Weissberger, ed., "The Chemistry of Heterocyclic Compounds, Imidazole and Derivatives", Part 1, Interscience, N.Y., 1953.*

Yeung, A. et al., "Photoreactives and thermal properties of psoralen cross–links", *Biochemistry* 1988, 27, 3204–3210.*

Youssefyeh, R. et al., "Synthetic routes to 4'–hydroxymethlnucleosides", *Tetrahedron Letters* 1977, 435–438.*

Zon, G., "Synthesis of backbone–modified DNA analogues for biological applicatins", *Journal of Protein Chemistry* 1987, 6, 131–145.*

Zon, G., "Oligonucleotide analogues as potential chemotherapeutic agents", *Pharmaceutical Research* 1988, 5, 539–549.*

Gagnier, R.P. et al., "1–(β–D–Ribofuranosyl)imidazo[4,5–d]pyridazine–4(5H)–one: A New Analogue of Inosine (1)", *J. Heterocyclic Chem.* 1982, 19, 221–223.

Hobbs, J. Et al., "Polynucleotides Containing 2'–Chloro–2'–deoxyribose", *Biochemistry* 1972, 11(23), 4336–4344.

Webb, T. and Matteucci, "Hybridization Triggered Cross–linking of Deoxyoligonucleotides", *Nucleic Acids Res.* 1986, 14(19), 7661–7674.

Hobbs et al., "Polynucleotides Containing 2'–Amino–2'deoxyribose and 2'–Azido–2'–deoxyribose," *Biochem.,* 1973, 12(25), 5138–5145.

Uhlmann, E. et al., "Antisense Oligonucleotides: A New Therapeutic Principle", *Chem. Reviews,* 1990, 90(4), 543–584.

Kurshid et al., FEBS Letters 1972, 28:1,25–28.

Kielanowska et al., Nucleic Acids Research 1976, 3:3, 817–824.

Kusmierek et al., ACTA Biochimica Polonica 1973, 20:4, 365–381.

Pike et al., J. Org. Chem. 1974, 39:25,3674–3676.

Ransford et al., J. Carbohydrates—Nucleosides—Nucleotides 1974, 1:3,275–278.

Rottman et al., Biomchemistry 1974, 13,2762–2771.

Tazawa et al., Biochemistry 1972, 11, 4931–4937.

M. Khurshid Alam Khan et al. J. Chem. Soc. Pak. Vol. 6, No. 4, 1984, 239–244.

* cited by examiner

COMPOUND FOR DETECTING AND MODULATING RNA ACTIVITY AND GENE EXPRESSION

This is a continuation of application Ser. No. 07/854,634, filed on Jul. 1, 1992, now abandoned, which is a continuation-in-part of U.S. Ser. No. 07/463,358, filed on Jan. 11, 1990, now abandoned, which is a continuation-in-part of U.S. Ser. No. 07/566,977, filed on Aug. 13, 1990 now abandoned. This case is also the United States National Phase filing of PCT application Ser. No. PCT/US91/00243, filed on Jan. 11, 1991.

BACKGROUND OF THE INVENTION

This invention relates to materials and methods for detecting and modulating the activity of RNA. The invention generally relates to the field of "antisense" compounds, compounds which are capable of specific hybridization with a nucleotide sequence of an RNA. In accordance with preferred embodiments, this invention is directed to the design, synthesis and application of oligonucleotides and to methods for achieving therapeutic treatment of disease, regulating gene expression in experimental systems, assaying for RNA and for RNA products through the employment of antisense interactions with such RNA, diagnosing diseases, modulating the production of proteins and cleaving RNA in site specific fashions.

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complementary to a specific, target, messenger RNA, mRNA sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172, 289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques*, vol. 6, pp. 958–973 (1988) and D. S. Loose-Mitchell, *TIPS*, vol. 9, pp. 45–47 (1988). Each of the foregoing provide background concerning general antisense theory and prior techniques.

Thus, antisense methodology has been directed to the complementary hybridization of relatively short oligonucleotides to single-stranded mRNA or single-stranded DNA such that the normal, essential functions of these intracellular nucleic acids are disrupted. Hybridization is the sequence specific hydrogen bonding of oligonucleotides to Watson-Crick base pairs of RNA or single-stranded DNA. Such base pairs are said to be complementary to one another.

Prior attempts at antisense therapy have provided oligonucleotides or oligonucleotide analogs which are designed to bind in a specific fashion to—which are specifically hybridizable with—a specific mRNA by hybridization. Such analogs are intended to inhibit the activity of the selected mRNA—to interfere with translation reactions by which proteins coded by the mRNA are produced—by any of a number of mechanisms. The inhibition of the formation of the specific proteins which are coded for by the mRNA sequences interfered with have been hoped to lead to therapeutic benefits.

A number of chemical modifications have been introduced into antisense oligonucleotides to increase their therapeutic activity. Such modifications are designed to increase cell penetration of the antisense oligonucleotides, to stabilize them from nucleases and other enzymes that degrade or interfere with the structure or activity of the oligonucleotide analogs in the body, to enhance their binding to targeted RNA, to provide a mode of disruption (terminating event) once sequence-specifically bound to targeted RNA, and to improve their pharmacokinetic properties. At present, however, no generalized antisense oligonucleotide therapeutic or diagnostic scheme has been found. The most serious deficiency of prior efforts has been the complete lack of a termination event once appropriate hybridization takes place or the presence of only a termination event that is so inefficient that a useful potency cannot be achieved due to the inability of oligonucleotides to be taken into cells at effective concentrations. The activity of the antisense oligonucleotides presently available has not been sufficient for effective therapeutic, research reagent, or diagnostic use in any practical sense. Accordingly, there has been and continues to be a long-felt need for oligonucleotides and oligonucleotide analogs which are capable of effective therapeutic and diagnostic antisense use.

This long-felt need has not been satisfied by prior work in the field of antisense oligonucleotide therapy and diagnostics. Others have failed to provide materials which are, at once, therapeutically or diagnostically effective at reasonable rates of application.

Initially, only two mechanisms or terminating events have been thought to be operating in the antisense approach to therapeutics. These are the hybridization arrest mechanism and the cleavage of hybridized RNA by the cellular enzyme, ribonuclease H (RNase H). It is likely that additional "natural" events may be involved in the disruption of targeted RNA, however.

These naturally occurring events are discussed by Cohen in *Oligonucleotides: Antisense Inhibitors of Gene Expression,* CRC Press, Inc., Boca Raton, Fla. (1989). The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides; P. S. Miller & P.O.P. Ts'O, *Anti-Cancer Drug Design,* 2:117–128 (1987), and α-anomer oligonucleotides are the two most extensively studied antisense agents which are thought to disrupt nucleic acid function by hybridization arrest.

The second "natural" type of terminating event is the activation of RNase H by the heteroduplex formed between the DNA type oligonucleotide and the targeted RNA with subsequent cleavage of target RNA by the enzyme. The oligonucleotide or oligonucleotide analog, which must be of the deoxyribo type, hybridizes with the targeted RNA and this duplex activates the RNase H enzyme to cleave the RNA strand, thus destroying the normal function of the RNA. Phosphorothioate oligonucleotides are the most prominent example of antisense agents which are thought to operate by this type of antisense terminating event. R. Y. Walder and J. A. Walder, in *Proceedings of the National Academy of Sciences of the U.S.A.,* Vol. 85, pp.5011–5015 (1988) and C. A. Stein, C. Subasinghe, K. Shenozuka, and J. Cohen, in

*Nucleic Acids Research*, Vol 16, pp.3209–3221 (1988) describe the role the RNase H plays in the antisense approach.

To increase the potency via the "natural" termination events the most often used oligonucleotide modification is modification at the phosphorus atoms. One oligonucleotide analog that has been developed in an effort to secure hybridization arrests is a methyl phosphonate oligonucleotide. Such analogs of oligonucleotides, analogs in the sense that the ordinary structure of the oligonucleotide has been modified into one or more methylphosphonate-substituted structures, have been extensively reported on. A number of authors including K. L. Agarwal & F. Riftina, *Nucleic Acids Research*, vol. 6, pp. 3009–3024 (1979); P. S. Miller, J. Yano, E. Yano, C. Carroll, C. Jayaraman, K. & P.O.P. Ts'o, *Biochemistry*, vol. 18, pp. 5134–5143 (1979); K. Jayaraman, K. McParland & P.O.P. Ts'o, *Proceedings of the National Academy of Sciences of the U.S.A.*, vol. 78, pp. 1537–1541 (1981); P. S. Miller, K. B. McParland, K. Jayaraman and P.O.P. Ts'o, *Biochemistry*, vol. 20, pp. 1874–1880 (1981); P. S. Miller, K. N. Fang, N. S. Kondo and P.O.P. Ts'o, *Journal of the American Chemical Society*, vol. 93, pp. 6657–6665 (1971); C. H. Agris, K. R. Blake, P. S. Miller, M. P. Reddy, and P.O.P. Ts'o, *Biochemistry*, vol. 25, 6268–6275 (1986); C. C. Smith, L. Aurelian, M. P. Reddy, P. S. Miller & P.O.P. Ts'o, *Proceedings of the National Academy of Sciences of the U.S.A.*, vol. 83, pp. 2787–2791 (1986); and S. W. Ruby and J. Abelson, *Science*, vol. 242, pp. 1028–1035 (1988) have reported on such oligonucleotide modifications. In such modifications, a non-bonding phosphoryl oxygen of the phosphorodiester linking moiety is replaced or the nucleotide elements together are replaced, either in total or in part, by methyl groups. This modification gives the molecule a greater resistance to nucleases. Inhibition of gene expression has been demonstrated with methylphosphonate oligonucleotides targeted to several mRNA's as reported, for example, by D. M. Tidd, T. Hawley, H. M. Warenius & I. Gibson, *AntiCancer Drug Design*, vol. 3, pp. 117–127, (1988). Methyl phosphonate modified oligonucleotides do not activate RNase H on hybridization to RNA and only operate in a strictly hybridization arrest mode. Oligonucleotides from this modification class typically possess inferior binding to targeted RNA, likely due to an R/S stereoisomer at each phosphorus atom, as well as increased steric bulk about the phosphate linkage.

Other workers have made other types of modifications to the phosphorus atom of the phosphate backbone of oligonucleotides in attempts to increase the efficiency of oligonucleotide therapy. The most prominent example is the use of phosphorothioate oligonucleotides. These have included HCPF Roelen, E. DeVroom, G. A. Van der Marel & J. H. VanBoom, *Nucleic Acid Research*, vol. 16, pp. 7633–7645 (1988) who employed methyl phosphorothionates. S. Agarwal, J. Goodchild, M. P. Civeira, A. H. Thornton, P. S. Sarin & P. C. Zamecnik, in *Proceedings of the National Academy of Sciences of the U.S.*, vol. 85, pp. 7079–7083 (1988); M. Matsukura, K. Shinozuka, G. Zon, H. Mitsuya, M. Reitz, J. S. Cohen & S. Broder, in *Proceedings of the National Academy of Sciences of the U.S.*, vol. 84, pp. 7706–7710 (1987); and C. J. Marcus-Sekura, A. M. Woerner, K. Shinozuka, G. Zon & G. V. Quinnan, in *Nucleic Acid Research*, vol. 15, pp. 5749–5763 (1987) employed phosphorothioates. See also Biosis/CA Selects abstract 110:88603e, reflecting U.S. Ser. No. 30,075 filed Sep. 1, 1987 which relates to phosporothioate modified oligonucleotides. The phosphorothioate modified oligonucleotides are thought to terminate RNA by activation of RNase H upon hybridization to RNA although hybridization arrest of RNA function may play some part in their activity.

Phosphorodithioates for such use have been disclosed by W. K. D. Brill, J. Y. Yang, Y. X. Ma, & M. H. Caruthers, *Journal of the American Chemical Society*, vol. 111, pp. 2321–2322 (1989). The phosphorothioate and phosphorodithioate type modifications possess a non-antisense mode of action in that they bind to and inhibit protein function. Protein interactions of oligonucleotides of this type unfortunately undermines the concept of the antisense approach which originally attracted researchers to this novel area. In addition, phosphoroamidates have been disclosed for such uses by A. Jager, M. J. Levy and S. M. Hecht in *Biochemistry*, vol. 27, pp. 7237–7246 (1988); and R. L. Letsinger, S. A. Bach & J. S. Eadie, in *Nucleic Acids Research*, vol. 14 pp. 3487–3499 (1986).

In contemplating the application of oligonucleotides and oligonucleotide analogs as antisense agents for therapeutic purposes, all applications of oligonucleotides as diagnostic, research reagents, and potential therapeutic agents require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides toward nuclease degradation.

A serious deficiency of oligonucleotides for these purposes, particularly antisense therapeutics, is the enzymatic degradation of the administered oligonucleotide by a variety of ubiquitous nucleolytic enzymes, intracellularly and extracellularly located, hereinafter referred to as "nucleases". It is unlikely that unmodified, "wild type", oligonucleotides will be useful therapeutic agents because they are rapidly degraded by nucleases. Modification of oligonucleotides to render them resistant to nucleases is therefore currently a primary focus of antisense research.

Modifications of oligonucleotides to enhance nuclease resistance have heretofore exclusively taken place on the sugar-phosphate backbone, particularly on the phosphorus atom. Phosphorothioates, methyl phosphonates, phosphorimidates, and phosphorotriesters (phosphate methylated DNA) have been reported to have various levels of resistance to nucleases. However, while the ability of an antisense oligonucleotide to bind to specific DNA or RNA with fidelity is fundamental to antisense methodology, modified phosphorous oligonucleotides, while providing various degrees of nuclease resistance, suffer from inferior hybridization properties.

Phosphorus atom modifications such as methyl phosphonates, phosphorothioates, and phosphoramidates, as described above, confer chirality at the phosphorus atom. Due to this prochiral nature of the phosphorous atom, modifications on the internal phosphorus atoms of modified phosphorous oligonucleotides result in Rp and Sp stereoisomers. Since a practical synthesis of stereoregular oligonucleotides (all Rp or Sp phosphate linkages) is unknown, oligonucleotides with modified phosphorus atoms have $n^2$ isomers with n equal to the number of the phosphorus atoms in the oligonucleotide so modified. Furthermore, modifications on the phosphorus atom have unnatural bulk about the phosphorodiester linkage which interferes with the conformation of the sugar-phosphate backbone and consequently, effects the stability of the duplex. The effects of phosphorus atom modifications cause inferior hybridization to the targeted nucleic acids relative to the unmodified oligonucleotide hybridizing to the same target.

The relative ability of an oligonucleotide to bind to complementary nucleic acids is compared by determining the melting temperature of a particular hybridization complex. The melting temperature ($T_m$), a characteristic physical property of double helixes, denotes the temperature in degrees centigrade at which 50% helical versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the $T_m$, the greater the strength of the binding of the strands. Non-Watson-Crick base pairing has a strong destabilizing effect on the $T_m$. Consequently, absolute fidelity of base pairing is necessary to have optimal binding of an antisense oligonucleotide to its targeted RNA.

Considerable reduction in the hybridization properties of methyl phosphonates and phosphorothioates has been reported by Cohen. Methyl phosphonates have a further disadvantage in that the duplex formed with RNA does not activate degradation by RNase H as an terminating event, but instead acts by hybridization arrest which can be reversed due to a helical melting activity located on the ribosome. Phosphorothioates are highly resistant to most nucleases. However, phosphorothioates typically exhibit non-antisense modes of action, particularly the inhibition of various enzyme functions due to nonspecific binding. Enzyme inhibition by sequence-specific oligonucleotides undermines the very basis of antisense chemotherapy.

While known modifications to oligonucleotides have been shown to have some effect on improving their inhibition of translation, and while such materials have shown some inhibitory activity towards the production of proteins coded by the mRNA, activities which are sufficient for diagnostic or therapeutic use have not been demonstrated.

Oligonucleotides modified to exhibit resistance to nucleases, to activate the RNase H terminating event, and to hybridize with appropriate strength and fidelity to its targeted RNA (or DNA) are still greatly desired for antisense oligonucleotide purposes.

M. Ikehara et al., *European Journal of Biochemistry* 139:447–450(1984) report the synthesis of a mixed octamer containing one 2'-deoxy-2'-fluoroguanosine residue or one 2'-deoxy-2'-fluoroadenine residue. W. Guschlbauer and K. Jankowski, *Nucleic Acids Res.* Vol. 8, p. 1421 (1980) have shown that the contribution of the N form (3'-endo, 2'-exo) increases with the electronegativeness of the 2'-substituent. Thus, 2'-deoxy-2'-fluorouridine contains 85% of the C3'-endo conformer. M. Ikehara et al., *Tetrahedron Letters* Vol. 42, p. 4073 (1979) have shown that a linear relationship between the electronegativeness of 2'-substituents and the % N conformation (3'-endo-2'-exo) of a series of 2'-deoxyadenosines. M. Ikehara et al., *Nucleic Acids Research* Vol. 5, p. 1877 (1978) have chemically transformed 2'-deoxy-2'-fluoro-adenosine to its 5'-diphosphate. This was subsequently enzymatically polymerized to provide poly(2'-deoxy-2'-fluoroadenylic acid).

Furthermore, evidence was presented which indicates that 2'-substituted 2'-deoxyadenosines polynucleotides resemble double stranded RNA rather than DNA. M. Ikehara et al., *Nucleic Acids Res.* Vol. 5, p. 3315 (1978) show that a 2'-fluorine substituent in poly A, poly I, and poly C duplexed to their U, C, or I complement are significantly more stable than the ribo or deoxy poly duplexes as determined by standard melting assays. M. Ikehara et al., *Nucleic Acids Res.* 4:4249 (1978) show that a 2'-chloro or bromo substituients in poly(2'-deoxyadenylic acid) provides nuclease resistance. F. Eckstein et al., *Biochemistry* Vol. 11, p. 4336 (1972) show that poly(2'-chloro-2'-deoxyuridylic acid) and poly(2'-chloro-2'-deoxycytidylic acid) are resistant to various nucleases. H. Inoue et al., *Nucleic Acids Research* Vol. 15, p.6131 (1987) describe the synthesis of mixed oligonucleotide sequences containing 2'-OMe at every nucleotide unit. The mixed 2'-OMe substituted sequences hybridized to their ribooligonucleotide complement (RNA) as strongly as the ribo-ribo duplex (RNA-RNA) which is significantly stronger than the same sequence ribo- deoxyribo heteroduplex ($T_m$s, 49.0 and 50.1 versus 33.0 degrees for nonamers). S. Shibahara et al., *Nucleic Acids Research* Vol. 17, p. 239 (1987) describe the synthesis of mixed oligonucleotides sequences containing 2'-OMe at every nucleotide unit. The mixed 2'-OMe substituted sequences were designed to inhibit HIV replication.

It is thought that the composite of the hydroxyl group's steric effect, its hydrogen bonding capabilities, and its electronegativeness versus the properties of the hydrogen atom is responsible for the gross structural difference between RNA and DNA. Thermal melting studies indicate that the order of duplex stability (hybridization) of 2'-methoxy oligonucleotides is in the order of RNA-RNA, RNA-DNA, DNA-DNA. The 2'-deoxy-2'-halo, azido, amino, methoxy homopolymers of several natural occurring nucleosides have been prepared by polymerase processes. The required 2'-modified nucleosides monomers have not been incorporated into oligonucleotides via nucleic acids synthesizer machines. Thus, mixed sequence (sequence-specific) oligonucleotides containing 2'-modifications at each sugar are not known except for 2'-deoxy-2'-methoxy analogs.

Other synthetic terminating events, as compared to hybridization arrest and RNase H cleavage, have been studied in an attempt to increase the potency of oligonucleotides for use in antisense diagnostics and therapeutics. Thus, an area of research has developed in which a second domain to the oligonucleotide, generally referred to as a pendant group, has been introduced.

The pendant group is not involved with the specific Watson-Crick hybridization of the oligonucleotide analog with the mRNA but is carried along by the oligonucleotide analog to serve as a reactive functionality. The pendant group is intended to interact with the mRNA in some manner more effectively to inhibit translation of the mRNA into protein. Such pendant groups have also been attached to molecules targeted to either single or double stranded DNA.

The type of pendant group known as an intercalating agent has been disclosed by Cazenave, N. Loreau, N. T. Thuong, J. J. Toulme and C. Helene in *Nucleic Acid Research*, vol. 15, pp. 4717–4736 (1987) and J. F. Constant, P. Laugaa, B. P. Roques & J. Lhomme, in *Biochemistry*, vol. 27, pp. 3997–4003 (1988). The disclosed purpose of such intercalating agents is to add binding stability to the hybrid formed between the oligonucleotide analog and the target nucleic acid by binding to the duplex formed between them.

It has also been disclosed to provide a pendant group to oligonucleotide analogs which is capable of cross-linking. Thus, a pendant agent such as psoralin has been disclosed by A. T. Yeung, B. K. Jones and C. T. Chu in *Biochemistry*, vol. 27, pp. 2304–3210 (1988). It is believed that after hybridization of the oligonucleotide analog to the target mRNA, the psoralin is photoactivated to cross-link with the mRNA forming a covalent bond between the oligonucleotide analog and the mRNA thereby permanently inactivating the mRNA molecule and precluding the further formation of protein coded by that particular portion of RNA.

It has also been proposed to employ an alkylating agent as a pendant group for oligonucleotide analogs for use in antisense approaches to diagnostics and therapeutics as disclosed by R. B. Meyer in the *Journal of American Chemical Society*, Vol. 111, pp 8517–8519 (1989) and D. G. Knorre an V. V. Vlassov, *Progress in Nucleic Acid Research and Molecular Biology*, Vol.32, pp.291–320 (1985).

The object of employing alkylating agents and pendant groups in oligonucleotide analogs in antisense approaches is to cause the alkylating agent to react irreversibly with the target mRNA. Such irreversible binding between the antisense oligonucleotide and the mRNA is generally covalent and leads to permanent inactivation of the mRNA with a concomitant halt in protein production from the portion of mRNA thus inactivated.

A further strategy which has been proposed is to use chemical reagents which, under selected conditions, can generate a radical species for reaction with the target nucleic acid to cause cleavage or otherwise to inactivate it. Proposed pendant groups of this category include coordination complexes containing a metal ion with associated ligands. A metal ion can change oxidation state to generate reactive oxygen-containing radical ions or other radical species. P. L. Doan, L. Perrouault, M. Chassignol, N. T. Thuong, & C. Helene, in *Nucleic Acids Research,* Vol. 15, pp. 8643–8659 (1987) have disclosed iron/EDTA and iron/porphrin species for this purpose. Copper/phenanthroline complexes have been disclosed by D. S. Sigman, in *Accounts of Chemical Research,* Vol. 19, pp. 180–186 (1986). G. B. Dreyer and P. B. Dervan, in *Proceedings of the National Academy of Sciences, U.S.A.,* Vol. 82, pp.968–972 (1985) have investigated the EDTA/Fe moiety to cleave nucleic acids.

Prior approaches using cross-linking agents, alkylating agents, and radical generating species as pendant groups on oligonucleotides for antisense diagnostics and therapeutics have several significant shortcomings. The sites of attachment of the pendant groups to oligonucleotides play an important, yet imperfectly known, part in the effectiveness of oligonucleotides for therapeutics and diagnostics. Prior workers have described most pendant groups as being attached to a phosphorus atom which, as noted above, affords oligonucleotides with inferior hybridization properties. Prior attempts have been relatively insensitive, that is the reactive pendant groups have not been effectively delivered to sites on the messenger RNA molecules for alkylation or cleavage in an effective proportion. Moreover, even if the reactivity of such materials were perfect, i.e. if each reactive functionality were to actually react with a messenger RNA molecule, the effect would be no better than stoichiometric. That is, only one mRNA molecule would be inactivated for each molecule of oligonucleotide. It is also likely that the non-specific interactions of the modified oligonucleotides with molecules other then the target RNA, for example with other molecules that may be alkylated or which may react with radical species, as well as self-destruction, not only diminishes the diagnostic or therapeutic effect of the antisense treatment but also leads to undesired toxic reactions in the cell or in vitro. This is especially acute with the radical species which are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agent and radical generating-types of antisense oligonucleotides is a significant drawback to their employment.

Accordingly, there remains a great need for antisense oligonucleotide formulations which are capable of improved specificity and effectiveness both in binding and in mRNA modulation or inactivation without the imposition of undesirable side effects.

OBJECTS OF THE INVENTION

It is a principal object of this invention to provide oligonucleotides and oligonucleotide analogs for use in antisense oligonucleotide diagnostics and therapeutics.

It is a further object of the invention to provide nuclease resistant, sugar modified oligonucleotides or oligonucleotide analogs for use in antisense oligonucleotide diagnostics, research reagents, and therapeutics.

It is a further object of this invention to provide such oligonucleotides and oligonucleotide analogs which are effective in modulating the activity of a DNA or an RNA.

A further object of this invention is to provide such oligonucleotides and oligonucleotide analogs which are less likely to invoke undesired or toxic side reactions.

A further object is to provide research and diagnostic methods and materials for assaying bodily states in animals, especially diseased states.

A further object is to provide means for modifying nucleic acids for effecting substitutions on selective portions thereof.

Yet another object is to provide therapeutic and research methods and materials for the treatment of diseases through modulation of the activity of DNA and RNA.

Still another object is to provide means for the selective cleavage of RNA.

These and other objects will become apparent to persons of ordinary skill in the art from a review of the present specification and attendant claims.

SUMMARY OF THE INVENTION

In accordance with the present invention, compositions for modulating the activity of DNA and RNA are provided. These compositions comprise a targeting portion specifically hybridizable with a preselected nucleotide sequence of RNA. The composition further provides a reactive portion capable of catalyzing, alkylating, or otherwise effecting the cleavage of RNA, especially of its phosphodiester bonds. The compositions may also include a tether, a means for connecting the targeting and reactive portions together to form the composition. In accordance with preferred embodiments, the compositions are adapted for placement of the reactive portion into the minor groove site of the hybrid structure formed from the hybridization of the RNA and the composition.

The targeting portion of the compositions of this invention preferably comprises an oligonucleotide analog comprising from about 3 to about 50 base units with 8 to 40 subunits being preferred and 12 to 25 being still more preferred. Oligonucleotides or oligonucleotide analogs having about 15 base units are preferable for the practice of certain embodiments of the present invention. In accordance with other preferred embodiments, the targeting portion is an analog of an oligonucleotide wherein at least some of the phosphodiester bonds of the oligonucleotide have been substituted with a structure which functions to enhance the ability of the compositions to penetrate into the intracellular region of cells where the RNA whose activity is to be modulated is located. It is preferred that such substitutions comprise phosphorothioate bonds or short chain alkyl or cycloalkyl structures. In accordance with other preferred embodiments, the phosphodiester bonds are substituted with structures which are, at once, substantially non-ionic and non-chiral.

In accordance with other preferred embodiments the reactive portion of the composition comprises a functionality capable of catalyzing the hydrolysis, cleavage, of phosphodiester bonds in RNA. Such functionalities may either be basic, acidic, or amphoteric. Heteroatomic species can be formulated to be either basic or acidic or, indeed, to be amphoteric for such purposes.

This invention also comprehends the employment of alkylating and free radical forming functionalities as the reactive portions of the subject compositions where said alkylating or free radical forming materials are delivered into the minor groove of the hybrid formed between the compositions of the invention and the RNA to be modulated.

In accordance with other embodiments of the invention, compositions are provided for modulating the activity of an RNA comprising certain heterocyclic structures having at least one RNA cleaving moiety or other moiety capable of interacting with an RNA appended thereto. These compositions are adapted for placement of the reactive, RNA cleaving moiety or other reactive moiety into the minor groove site of the hybrid structure formed from the RNA and the composition through careful selection of the sites of attachment of the RNA cleaving moieties. Such compositions may include sugar or sugar analog portions and novel nucleoside base portions. Accordingly, novel nucleosides and nucleoside analogs are provided. Such nucleosides and nucleoside analogs may be incorporated into oligonucleotides and oligonucleotide analogs which are useful in the practice of the invention.

The invention also is directed to methods for modulating the activity of an RNA comprising contacting an organism having the RNA with a composition formulated in accordance with the foregoing considerations. It is preferred that the RNA which is to be modulated be preselected to comprise preferably messenger RNA which codes for a protein whose formation is to be modulated. The invention may also be applied to pre-messenger RNA and, indeed, to RNA generically and to double stranded DNA. The targeting portion of the composition to be employed is, thus, selected to be complementary to the preselected portion of RNA, that is, to be an antisense oligonucleotide for that portion.

This invention is also directed to methods for treating an organism having a disease characterized by the undesired production of a protein comprising contacting the organism with a composition in accordance with the foregoing considerations, preferably one which is designed to specifically bind with messenger RNA which codes for the protein whose production is to be inhibited.

The invention is also directed to the utilization of groups appended to oligonucleotides which do not include a reactive function. Such pendant groups may lead to enhanced oligonucleotide uptake, enhanced resistance of oligonucleotide to degradation by nucleases, and stronger binding of the oligonucleotides to targeted RNA. Such oligonucleotide can disrupt RNA by hybridization arrest and/or by activation of RNase H as well as by cleavage of the RNA phosphorodiester bonds or other destruction thereof by other reactive functionalities.

The invention is also directed to functionalities which serve to attach reporter groups such as biotin and various fluorophores to sequence-specific oligonucleotides for diagnostic purposes. More than one non-reactive functionality may be attached to each oligonucleotide, two or more non-reactive functionalities may be attached to a single nucleoside unit, and a combination of non-reactive functionalities and reactive functionalities may be attached to a single nucleoside unit or a single oligonucleotide. Non-reactive functionalities and reactive functionalities attached to sequence-specific oligonucleotides are preferably designed to reside in the minor groove or on the minor groove side of the heteroduplex.

In accordance with other preferred embodiments, the present invention, compositions which are resistant to nuclease degradation and which modulate the activity of DNA and RNA are provided. These compositions are comprised of sugar modified oligonucleotides or oligonucleotide analogs, the targeting portions of which are specifically hybridizable with preselected nucleotide sequences of single-stranded or double-stranded DNA or RNA. The sugar modified oligonucleotides recognize and form double strands with single-stranded DNA and RNA or triple strands with double-stranded DNA and RNA.

The nuclease resistant oligonucleotides of this invention consist of a single strand of nucleic acid bases linked together through linking groups. The target portion of the nuclease resistant oligonucleotide may range in length from about 5 to about 50 nucleic acid bases. However, in accordance with the preferred embodiment of this invention, a target sequence of about 15 bases in length is optimal.

The nucleic acid bases may be pyrimidines such as thymine, uracil or cytosine, or purines such as guanine or adenine, or both, arranged in a specific sequence. Additionally, they may be any of the novel bases of the invention. The sugar moiety of such bases may be of the deoxyribose or ribose type. The groups linking the bases together may be the usual sugar phosphate nucleic acid backbone, but may also be modified as a phosphorothioate, methylphosphonate, or phosphate alkylated moiety to further enhance the sugar modified oligonucleotide properties, along with removal of a 5'-methylene group and/or carbocyclic sugar.

In accordance with one embodiment of this invention, the targeting portion is an analog of an oligonucleotide wherein at least one of the 2'-deoxy ribofuranosyl moieties of the nucleoside unit is modified. A hydrogen or a hydroxyl, halo, azido, amino, methoxy or alkyl group may be added. For example, H, OH, lower alkyl, substituted lower alkyl, F, Cl, Br, CN, $CF_3$, $OCF_3$, OCN, 0-alkyl, S-alkyl, SOME, $SO_2Me$, $ONO_2$, $NO_2$, $N_3$, $NH_3$, $NH_2$, NH-alkyl, $OCH_2CH=CH_2$, $OCH=CH_2$, $OCH_2C\equiv CH$, $-OC\equiv CH$, aralkyl, heteroaralkyl, heterocycloalkyl, aminoalkylamino, heterocycloalkylamino, polyalkylamino, substituted silyl, a RNA cleaving moiety or a group for improving the pharmacodynamic properties of an oligonucleotide or a group for improving the pharmacokinetic properties of an oligonucleotide where alkyl is a straight or branched chain of C1 to C12 may be used, with unsaturation within the carbon chain, such as allyloxy being particularly preferred.

The resulting novel oligonucleotides or oligonucleotide analogs are resistant to nuclease degradation and exhibit hybridization properties of higher quality relative to wild type (DNA-DNA and RNA-DNA) duplexes and the phosphorus modified oligonucleotide antisense duplexes containing phosphorothioates, methylphosphonates, phophoramidates and phosphorotriesters.

The invention further is directed to diagnostic methods for detecting the presence or absence of abnormal RNA molecules or abnormal or inappropriate expression of normal RNA molecules in organisms or cells. It is also directed to methods for the selective cleaving of RNA such as for research and diagnostics and to the RNA thus formed. Such selective cleaving is accomplished by interacting RNA with compositions of the invention which have reactive portions capable of effecting such cleavage and targeting portions designed to enforce selectivity.

The compositions useful for modulating the activity of an RNA or detecting its presence in accordance with this invention generally comprise three portions. The first portion, the targeting portion, is a portion which is specifically hybridizable with a preselected nucleotide sequence of the RNA to be modulated. It is generally desirable to select a sequence of RNA which codes for or which is involved in the production of proteins whose synthesis is ultimately to be modulated or inhibited in entirety. The targeting portion of the composition is an oligonucleotide analog. It is designed and prepared conveniently, through solid state synthesis of known methodology, to be complementary to or at least to be specifically hybridizable with the preselected nucleotide sequence of the RNA. Nucleic acid synthesizers are commercially available and their use is generally understood by persons of ordinary skill in the art to be capable of generating nearly any oligonucleotide of reasonable length which may be desired.

The invention is also directed to methods for modulating the production of a protein by an organism comprising contacting the organism with a composition formulated in accordance with the foregoing considerations. It is preferred that the RNA or DNA portion which is to be modulated be preselected to comprise that portion of DNA or RNA which codes for the protein whose formation is to be modulated. The targeting portion of the composition to be employed is, thus, selected to be complementary to the preselected portion of DNA or RNA, that is to be an antisense oligonucleotide for that portion.

This invention is also directed to methods of treating an organism having a disease characterized by the undesired production of a protein. This method comprises contacting the organism with a composition in accordance with the foregoing considerations. The composition is preferably one which is designed to specifically bind with messenger RNA which codes for the protein whose production is to be inhibited.

The invention further is directed to diagnostic methods for detecting the presence or absence of abnormal RNA molecules or abnormal or inappropriate expression of normal RNA molecules in organisms or cells.

The invention is also directed to methods for the selective binding of RNA for research and diagnostic purposes. Such selective, strong binding is accomplished by interacting such RNA or DNA with compositions of the invention which are resistant to degradative nucleases and hybridize stronger and with greater fidelity than any other known oligonucleotide or oligonucleotide analog.

In accordance with a further embodiment of the invention, novel processes are provided for the synthesis of novel nucleoside analogs that are substituted in the 2' position and which are useful for incorporation into oligonucleotides and analogs of the invention. Such process provides for introduction of a 2'substituent in the absence of blocking of either the 3' or 5'hydroxyl groups of a ribofuranosyl nucleoside. Such processes utilize treatment with sodium hydride followed by use of an alkyl halide or with uracil, stannous chloride. No protecting groups on the nucleoside bases are necessary except for the exo-cyclic amino group of guanosine. The reactions are conducted at or near room temperature. These conditions are contrasted to prior known process that require strong alkylating agents, as for instance diazomethane. Such strong alkylating agents necessitate the complete protection of all reactive sites on the nucleoside bases and the 3' and 5' sugar hydroxyls.

In accordance with an even further embodiment of the invention, a novel process is provided for the synthesis of novel 3-deaza nucleosides and oligonucleotides that incorporate these nucleosides. In this process compounds such as 5-cyanomethyl-1-(2'-deoxy-3',5'-di-O-p-toluoyl-D-erythro-pentofuranosyl)imidazole-4-carboxylate or 5-cyano-methyl-1-(2'-deoxy-D-erythro-pento furanosyl) imidazole-4-carboxylate are prepared. The 5-cyano-methyl compounds are prepared from the corresponding 5-cyanomethyl compound utilizing sodium hydride and an appropriate alkyl halide. The carboxalates are deblocked and converted to the corresponding carboxamides. The 5' position of the compounds are then protected and the compounds derivatized at the 3' position with an appropriate phorphoramidite or other activated phosphate group suitable for use on a DNA synthesizer. An oligonucleotide is constructed on the synthesizer. Such oligonucleotide incorporates one or more of the 5-cyano-methyl imidazole compounds in its sequence. The imidazole compound cyclizes to the corresponding 3-deaza purine or 3-substituted-3-deaza purine concurrently with cleavage of the oligonucleotide from the synthesizer support upon treatment with excess concentrated ammonium hydroxide.

The modified nucleotides (modified monomers) possessing the required functionality in the sugar portion and/or the heterocyclic portion may be used to prepare desired novel, oligonucleotides and analogs of this invention. The structure and synthesis of the modified nucleotides have not been known previously and are herewithin described for the first time. The sites of functionality in the sugars and heterocycles are novel, and have been preferably designed such that the functionalities will reside in or on the minor groove formed by the heteroduplex between the modified oligonucleotide and the targeted RNA. The minor side or minor groove of the duplexes formed between such modified oligonucleotides and the targeted RNA has been found to be the greatly preferred site for functional group activity.

One group of compositions useful for modulating the activity of an RNA or DNA molecule in accordance with this invention generally comprise a sugar modified oligonucleotide containing a target sequence which is specifically hybridizable with a preselected nucleotide sequence of single stranded or double stranded DNA or RNA molecule and which is nuclease resistant.

It is generally desirable to select a sequence of DNA or RNA for or which is involved in the production of proteins whose synthesis is ultimately to be modulated or inhibited in entirety. The targeting portion of the composition is generally an oligonucleotide analog. It is synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired.

In the context of this invention, the term "oligonucleotide" refers to a plurality of joined nucleotide units formed in a specific sequence from naturally occurring bases and pentofuranosyl groups joined through sugar groups by native phosphodiester bonds. These nucleotide units may be nucleic acid bases such as guanine, adenine, cytosine, thymine or uracil. The sugar group may be deoxyribose or ribose. This term refers to both naturally occurring or synthetic species formed from naturally occurring subunits.

"Oligonucleotide analog" or "modified oligonucleotides" as these terms are used in connection with this invention, refer to moieties which function similarly to natural oligonucleotides but which have non-naturally occurring portions. Oligonucleotide analogs or modified oligonucleotides may have altered sugar moieties, altered bases, both altered sugars and bases or altered inter-sugar linkages, for example phosphorothioates and other sulfur containing species which are known for use in the art. The oligonucleotide analogs of the invention may increase nuclease resistance of the oligonucleotide composition and thus facilitate anti-sense therapeutic, diagnostic use or research reagent use of the compositions of this invention.

It is greatly preferred in the present invention to employ oligonucleotide analogs or modified oligonucleotides rather than the oligonucleotides themselves. In this context, oligonucleotide analog refers to a structure which is generally similar to native oligonucleotides, but which has been modified in one or more significant ways.

It is generally preferred for use in some embodiments of this invention that some positions of the nucleotide base be substituted in order to increase the nuclease resistance of the composition while maintaining the integrity of the oligonucleotide binding capabilities.

It is preferred in some embodiments of the present invention to employ further modified oligonucleotides. In this context, modified oligonucleotide analogs refers to a structure which is generally similar to native oligonucleotides, but which have been modified in one or more significant ways.

In order to enhance penetration into the intracellular spaces of cells where the messenger RNA or DNA, which are the targets of the overall composition reside, RNA or DNA (which are the targets of the overall composition) reside, preferred embodiments of the invention provide modifications of the oligonucleotides. Such modifications may provide oligonucleotides that are substantially less ionic than native forms. Such modifications facilitate penetration of oligonucleotides into the intracellular spaces. Any of the existing or yet to be discovered methods for accomplishing this goal may be employed in accordance with the practice of the present invention. At present, it has been found preferable to employ substitutions for the phosphorodiester bond, which substitutions are not only relatively less ionic than the naturally occurring bonds but are also substantially nonchiral.

As will be appreciated, the phosphorus atom in the phosphorodiester linkage is "prochiral". Modifications at the phosphorus, such as is done in methyl phosphonates and phosphorothioates type oligonucleotides, result in essentially chiral structures. Chirality results in the existence of two isomers at each chiral center which may interact differently with cellular molecules. Such an unresolved mixture of isomers may inhibit the transport of the resulting compositions into the intracellular spaces or decrease the affinity and specificity of hybridization to the specific target RNA or DNA. Thus, it is preferred in some embodiments of this invention to employ substantially non-ionic, substantially non-chiral entities in lieu of some or all of the phosphorodiester bonds. For this purpose, short chain alkyl or cycloalkyl structures especially $C_2$–$C_4$ structures are preferred. As is set forth in U.S. Pat. No. 5,138,045 the modification of the sugar structure including the elimination of one of the oxygen functionalities may permit the introduction of such substantially non-chiral, non-ionic substituents in this position. The entirety of the disclosure of that application is incorporated herein by reference in order to disclose more fully such modifications.

In keeping with the goals of the invention are the standard backbone modifications such as substituting P for S, Me—P, MeO—P, $H_2N$—P, etc. These substitutions are thought in some cases to enhance the sugar modified oligonucleotide properties.

The targeting portions of the compositions of the present invention, are preferably oligonucleotide analogs having from about 3 to about 50 base units. It is more preferred that such analogs have from about 8 to about 40 base units and even more preferred that from about 12 to about 25 be employed. At present, it is believed that oligonucleotides or analogs having about 15 base units will likely be found to be best for the practice of certain embodiments of the present invention. It is desired that the targeting portion be adapted so as to be specifically hybridizable with the preselected nucleotide sequence of the RNA selected for modulation.

At present, the oligonucleotide analogs which are believed to be particularly suitable for the practice of one or more embodiments of the present invention will comprise one or more subunits having gross schematic structures as shown in Formula 1.

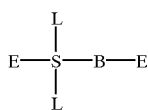

1 wherein B is any of the purine or pyrimidine bases, modified bases or base analogs including those which are known in naturally-occurring oligonucleotides or for use in modified oligonucleotides, or which exhibit similar functions; E is a RNA cleaving moiety, a group for improving the pharmacokinetic properties of said oligonucleotide, a group for improving the pharmacodynamics of said oligonucleotide, H, or OH and other small base substitutent groups; S is a sugar or sugar analog; and L is a sugar linking group. The sugar linking group L may be any of those structures either naturally occurring, described herein, or otherwise known which are capable of linking sugar moieties of oligonucleotides or sugar analogs, together to form the targeting portion of the compositions of this invention. It is preferred that these sugar linking functions either comprise a phosphodiester structure or a substantially non-ionic, substantially non-chiral structure as described herein-before, such as lower alkyl and cycloalkyl, especially $C_2$–$C_4$ alkyl. Note that when lower alkyl structures are employed, the 5' methylenes of one or more sugars may be eliminated. Preferrable, at least some of the phosphodiester bonds of said oligonucleotide are substituted phosphorothionate, methyl phosphonate, or alkyl phosphate.

As will be appreciated by persons of ordinary skill in the art, variations in the structures of the sugar moieties useful in the preparation of the subject compositions may be made without deviating from the spirit of the invention. Once again, it is not necessary that every sugar linking function be in a modified form A substantial number and even a predominance of such linking groups may exist in the native, phosphodiester form as long as the overall targeting portion of the compositions of the molecules exhibits an effective ability to penetrate into the intracellular spaces of cells of the organism in question or otherwise to contact the target RNA and to specifically bind therewith to form a hybrid capable of detecting and modulating the RNA activity. Of course, fully unmodified, native phosphodiester structures may be used as well.

It is not necessary to tether more than one, or perhaps two RNA cleaving functionalities, groups for improving the pharmacodynamics of oligonucleotides or groups for improving the pharmacokinetics of oligonucleotides, to oligonucleotides in accordance with this invention in order to provide the benefits of the invention. Thus, an RNA cleaving moiety or pharmacodynamic improving group or pharmacokinetic improving group will preferably be tethered to a relatively small proportion of the subunits, generally only one or two, comprising the oligonucleotide analog which is the targeting portion of the compositions of the invention. In other embodiments of the invention, however, all of the nucleotides in an oligonucleotide can be modified to include one or more RNA cleaving moiety groups, pharmacodynamic improving groups or pharmacokinetic improving groups.

It is believed desirable in accordance with certain preferred embodiments, to attach the RNA cleaving portion or pharmacodynamic improving group portion or pharmacokinetic improving group portion of the compositions of this invention to one of the nucleosides forming the subunits of the targeting portion. Such an attachment may be depicted in accordance with Formulas 2 through 7.

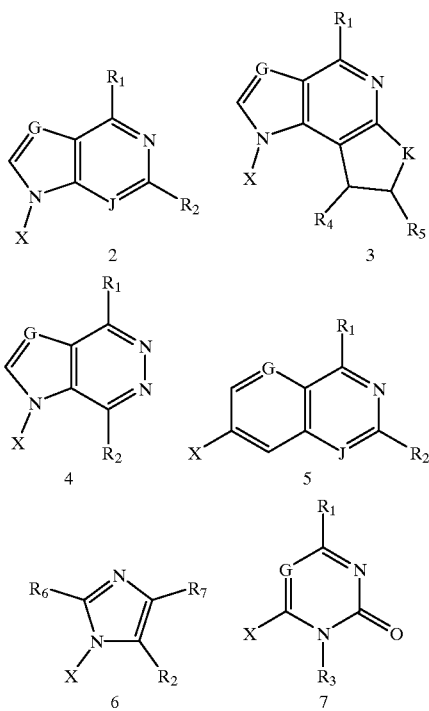

Where G and K are, independently, C or N;

J is N or $CR_3$;

$R_1$ is OH or $NH_2$;

$R_2$ and $R_3$ are H, $NH_2$, lower alkyl, substituted lower alkyl, lower alkenyl, aralkyl, alkylamino, aralkylamino, substituted alkylamino, heterocycloalkyl, heterocycloalkylamino, aminoalkylamino, hetrocycloalkylamino, polyalkylamino, a RNA cleaving moiety, a group for improving the pharmacokinetic properties of an oligonucleotide or a group for improving the pharmacodynamic properties of an oligonucleotide;

$R_4$ and $R_5$ are H, OH, $NH_2$, lower alkyl, substituted lower alkyl, substituted amino, a RNA cleaving moiety, a group for improving the pharmacokinetic properties of an oligonucleotide or a group for improving the pharmacodynamic properties of an oligo-nucleotide;

$R_6$ and $R_7$ are H, OH, $NH_2$, SH, halogen, $CONH_2$, $C(NH)NH_2$, C(O)O-alkyl, $CSNH_2$, CN, C(NH)NHOH, lower alkyl, substituted lower alkyl, substituted amino, a RNA cleaving moiety, a group for improving the pharmaco-kinetic properties of an oligonucleotide or a group for improving the pharmacodynamic properties of an oligonucleotide;

X is a sugar or a sugar analog moiety and where said sugar analog moeity is a sugar substituted with at least one substitutent comprising a RNA cleaving moiety, a group for improving the pharmacodynamic properties of an oligonucleotide, or a group for improving the pharmacokinetic properties of an oligonucleotide;

provided that when said composition is represented by Formula 2 and when G is N and J is N then X is said sugar analog moiety substituted with at least one group other than F and $OCH_3$;

further provided that if said oligonucleotide includes only one of said modified nucleotide and G=N and J=N and all of the sugar linking groups are unsubstituted phosphordiester linkages then X is not a sugar or a sugar analog moiety containing a 2'-$OCH_3$ or 2'-F;

further provided when said composition is represented by Formula 2 and G is N and J is $CR_3$ and $R_3$ is H then X is said sugar analog moiety;

further provided that when said composition is represented by Formula 4 and when G is N and X is said sugar, $R_2$ is not H;

further provided that when said composition is represented by Formula 6 and $R_6$ is H and $R_2$ is $NH_2$ and $R_7$ is $CONH_2$, $CSNH_2$, C(O)O-alkyl, $C(NH)NH_2$ or $C(NH)NHOH$ then X is said sugar analog moiety;

further provided that when said composition is represented by Formula 6 and $R_6$ is H, OH or SH and $R_7$ is C(O)O-alkyl or $C(NH)NH_2$ and $R_2$ is —$CH_2CN$ then X is said sugar analog moiety; and further provided that when said composition is represented by Formula 7 and $R_3$ is H and G is C then X is said sugar analog moiety.

It is believed that attachment of the RNA cleaving functionality to the 2' position of the furanosyl portion of a nucleoside forming part of the oligonucleotides of this invention is preferred in certain embodiments in order to permit the tether portion to deliver the reactive functionality of the compositions of the invention into the minor groove formed by the hybridization of the composition with the messenger RNA. Other sites of attachment on the "sugar" portion of the nucleosides forming the oligonucleotides of this invention, which are believed to be preferred for placing a reactive functionality of the invention into the minor groove upon hybridization of the composition with a messenger RNA are depicted in Formulas 8 and 9. These moieties may include sugar analogs which are not strictly within the conventional definition of sugars but which serve substantially similar functions.

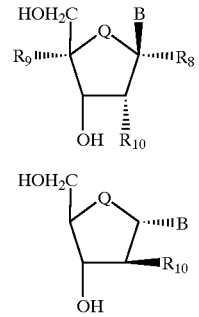

Where Q is 0 or $CHR_{11}$;

B is a point of attachment which can be a naturally occuring or synthetic variable base moiety;

$R_8$ and $R_9$ are H, lower alkyl, substituted lower alkyl, a RNA cleaving moiety, a group for improving the pharmacodynamic properties of an oligonucleotide or a group for improving the pharmacokinetic properties of an oligonucleotide;

$R_{10}$ is H, OH, lower alkyl, substituted lower alkyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2C=CH$, OC=CH aralkyl, heteroaralkyl, heterocycloalkyl, amino-alkylamino, heterocycloalkyl, polyalkylamino, substituted silyl, a RNA cleaving moiety, a group for improving the pharmacodynamic properties of an oligonucleotide or a group for improving the pharmacokinetic properties of an oligonucleotide; and $R_{11}$ is H, OH lower alkyl, substituted lower alkyl, a RNA cleaving moiety, a group for improving the pharmacokinetic properties of an oligonucleotide, or a group for improving the pharmacodynamic properties of an oligonucleotide.

It is preferred that $R_{10}$ be lower alkyl, substituted lower alkyl, CN, $CF_3$, $OCF_3$, OCN, O—$C_3$–$C_{12}$-alkyl, S-alkyl, SOMe, $SO_2Me$, $ONO_2$, $NO_2$, NH-alkyl, OCH=$CH_2$, $OCH_2C$≡CH, OC≡CH aralkyl, heteroaralkyl, heterocycloalkyl, polyalkylamino, substituted silyl, a RNA cleaving moiety or a group for improving the pharmacodynamic properties of an oligonucleotide or a group for improving the pharmaco-kinetic properties of an oligonucleotide.

Exemplary base moieties are those set forth in Formulas 2 through 7. The sugar, X, preferably is ribofuranosyl or 2'-deoxyribofuranosyl. A perferred sugar analog moiety is 2'-deoxy-2'- substituted ribo-furanosyl. Other sugar analog moieties are as above in Formulas 8 and 9. The base B of Formulas 8 and 9 are any of the natural pyrimidinyl-1- or purinly-9 bases including uracil, thymine, cytosine, adenine and guanine, 5-alkylcytosine such as 5-methylcytosine as well novel bases of the invention as depicted in Formulas 2 through 7.

Alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methylpentyl, 3-methylpentyl, 2-ethylhexyl, 2-propylpentyl. Alkenyl groups include but are not limited to unsaturated moieties derived from the above alkyl groups including but not limited to vinyl, allyl, crotyl, propargyl. Aryl groups include but are not limited to phenyl, tolyl, benzyl, napththyl, anthracly, phenanthryl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocyclo-alkylamines such as imidazol-1, 2 or 4-yl-propylamine. Substitutent groups for the above include but are not limited to other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones and sulfoxides. Other suitable substituent groups also include rhodamines, coumarins, acridones, pyrenes, stilbenes, oxazolo-pryidocarbazoles, anthraquinones, phenanthridines, phenazines, azidobenzenes, psoralens, porphyrins and cholesterols.

The sites that functionality may be attached to in the nucleosidic units which in turn may be converted to modified oligonucleotide is critical in the design of compositions for sequence-specific destruction or modulation of targeted RNA. The functionality must not interfere with Watson-Crick base pair hydrogen bonding rules as this is the sequence-specific recognition/binding factor essential for selection of the desired RNA to be disrupted.

Furthermore, approaches to perfect complementation between the modified oligonucleotides and targeted RNA will result in the most stable heteroduplexes. This is desired because the heteroduplex must have a sufficient half life to allow the reactive or non-reactive functionalities of this invention to initiate the cleavage or otherwise disruption of RNA function.

The half life of the perfectly formed duplex will be greatly effected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA disruption.

For RNA inactiviation, a further important factor concerning the placement of the tethered functionality is that it must be in appropriate proximity to receptive substrate located in the targeted RNA, especially the most sensitive "trigger" point, the 2'-hydroxyl group. A variety of structural studies such as X-ray diffraction, chemical reaction, and molecular modeling studies suggests that the 2'-hydroxyl group of RNA in a duplex or heteroduplex resides in the minor groove. Therefore, functionality placed on sequence-specific oligonucleotides (via modified nucleosides) should preferably reside in the minor groove formed between the oligonucleotide and the targeted RNA, not interfere with duplex formation and stability, and initiate cleavage or disruption of the RNA.

It has now been found that certain positions on the nucleosides of double stranded nucleic acids are exposed in the minor groove and may be substituted without affecting Watson-Crick base-pairing or duplex stability. Reactive or non-reactive functionalities placed in these positions in accordance with this invention can best initiate cleavage and destruction of targeted RNA or interfere with its activity.

Reactive functionalities or pendant groups of oligonucleotides previously described in the literature have been almost exclusively placed on a phosphorus atom, the 5-position of thymine, and the 7-position of purines. A phosphorus atom attachment site can allow a reactive group to access both the major and minor grooves. However, internal phosphorus modification results in greatly reduced heteroduplex stability. Attachments at the 3' and/or 5° ends are limiting in that only one or two functional groups can be accommodated in the oligonucleotide. Functionality placed in the 5-position or 7-position of heterocycles (bases) pyrimidine and purine respectively will reside in the major groove of the duplex and will not be in proximity to the RNA 2'-hydroxyl substrate. Further such placement can interfer with Watson-Crick binding.

Pendant groups that do not possess reactive functionality but serve to enhance the pharmacodynamic and pharmacokinetic properties of the oligonucleotides are also preferred for use in accordance with certain embodiments of this invention. Pharmacodymanic property improvement means, in this context, improved oligonucleotide uptake, enhanced oligonucleotide resistance to degradation, and/or strengthened sequence-specific hybridization with RNA. Pharmacokinetic property improvement means, in this context, improved oligonucleotide uptake, distribution, metabolism or excretion. Such pendant groups do not initiate chemical reactions. They preferrably include alkyl chains, polyamines, ethylene glycols, polyamides, aminoalkyl chains, amphipathic moieties, points for reporter group attachment, and intercalators attached to any of the preferred sites for attachment.

It is believed that attaching RNA cleaving moieties in accordance with the foregoing considerations will permit those moieties to lie in the minor groove of the hybrid formed from the composition of the present invention and the messenger RNA for which modulation is desired. It is possible that other positions for attachment of the RNA cleaving moieties having a similar effect may be found, especially when further modifications of the purine or pyrimidine structure is undertaken as may be done by persons of ordinary skill in the art without deviating from the spirit of the present invention. Once again, it is to be understood that preferably one, or at most a few RNA cleaving moieties are generally to be employed. Thus, artisans in the field will have great latitude in selecting means of attachment of the RNA cleaving moieties, the pharmacodynamic improving group or the pharmocokinetic improving group in accordance with this invention.

The RNA cleaving moieties of the compositions of the present invention are designed in such a fashion that they can be effective in performing their proximate task, leading to the desired modulation of RNA activity. It is believed to be useful to employ heteroatomic substitutions in the RNA cleaving moieties of these molecules, especially amides and polyamides, and indeed some may be preferred in order to ensure even tighter binding between the target mRNA and the compositions of the invention.

Oligonucleotide analogs particularly suited for the practice of one or more embodiments of the present invention comprise 2'-sugar modified oligonucleotides wherein one or more of the 2'-deoxy ribofuranosyl moieties of the nucleoside unit is modified with a hydrogen or hydroxyl, halo, azido, amino, methoxy or alkyl group. For example, the substitutions which may occur include H, OH, lower alkyl, substituted lower alkyl, F, Cl, Br, CN, $CF_3$, $OCF_3$, OCN, O-alkyl, S-alkyl, SOME, $SO_2Me$, $ONO_2$, $NO_2$, $N_3$, $NH_2$, NH-alkyl, OCH $CH_2$=CH, $_2OCH$=$CH_2$, $OCH_2C$≡CH OC≡CH OCCH, aralkyl, heteroaralkyl, hetero-cycloalkyl, aminoalkylamino, heterocycloalkylamino, poly-alkylamino, substituted silyl, a RNA cleaving moiety or a group for improving the pharmacodynamic properties of an oligonucleotide or a group for improving the pharmaco-kinetic properties of an oligonucleotide where alkyl is a straight or branched chain of $C_1$ to $C_{12}$ with unsaturation within the carbon chain such as allyloxy.

These modified bases are linked together and to the rest of the oligonucleotide or oligonucleotide analog through a sugar linking group. The linking group may be any of those structures described herein which are capable of linking sugar moieties of oligonucleotides together to form the targeting portion of the compositions of this invention. It is preferred that these sugar linking groups comprise the phosphodiester structure or a derivative of such. Derivatives of the phosphodiester structure may include substitution of a sulphur, methyl, methyl oxide, or amine group for an oxygen. The sugar phosphate nucleic acid backbone may be modified as a phosphorothioate, methylphosphonate, or phosphate alkylated moiety. The phosphodiester linkage may also be replaced by a carbon or ether linkage as discussed above.

In order to attach tethered functionality to the exo-cyclic 2-position of 2'-deoxyadenosines, 2'-deoxyguanosines, and other purines and purine analogs, the following exemplary procedure can be utilized. 2,6-Dichloropurine (Aldrich Chemical Co.) is deoxyribosylated with 3,5-di-O-(4-methylbenzoyl)-α-D-erythro-pentofuranosyl chloride in accordance with the procedure set forth in *Synthetic Procedures in Nucleic Acid Chemistry*, Vol.1, p. 521, (1968) and subsequently aminated with methanolic ammonia according to the procedure of the Journal of *American Chemical Society*, Vol. 106, pg. 6379 (1984). The resulting 2-chloro-2-deoxyadenosine is converted into a series of 2-substituted 2-deoxyadenosines by nucleophilic displacement of the 2-chloro group with selected nucleophilic reactive functionalities. In this manner, a variety of substituted species such as amines, oxygens, sulfurs, and seleniums can be attached directly to the 2-position carbon of the bicyclic ring. Reactive functionalities attached to the 2-position of 2'-deoxyadenosine via a carbon atom can be obtained from 5-amino-1-(2-deoxy-β-D-erythro-pentofuranosyl) imidazole 4-carboxamidine and substituted aldehydes according to the published procedure of the *Journal of American Chemical Society*, Vol. 90 p. 4962, (1974) or from palladium-catalyzed cross coupling reactions as set forth in *Nucleosides and Nucleotides*, Vol. 8 p. 699, (1989) with 2-iodo-2'-deoxyadenosine. See U.S. Pat. No. 4,719,295. The 2-reactive functionality 2'-deoxyadenosines can be deaminated with adenosine deaminase or nitrous acid to afford deoxyguanosine counterparts. As per selected examples below 2-substituted-2-deoxyguanosines and -2-adenosines can be converted to the 5'-di-methoxy-trityl-3'-cyanoethylphosphoramidites (N6-benzoyl for adenine types and N2-isobutryl for guanine types). These are routinely inserted into oligonucleotides via automated, solid phase DNA synthesizers according to well-known procedures.

Reactive functionalities emanating from the 3-position of 2'-deoxyguanosine can be obtained by a multi-step synthesis starting with the alkylation of the methylene moiety of methyl 5-(cyanomethyl)-1-(2-deoxy-3,5-di-O-p-toluoyl-β-D-erythropento-furanosyl) imidazole-4-carboxylate with halogenated reactive functionalities. The starting imidazole material can be synthesized according to a known procedure. *Journal of Medicinal Chemistry*, Vol. 27 p. 1389 (1984). The alkylated imidazoles are treated with methanolic ammonia to remove the toluoyl groups and to provide imidazole carboxamides. These are inserted into oligonucleotides as 5'-DMT-3'-cyanoethyl phosphoramidites through routine solid state synthetic techniques.

Following synthesis, the prepared oligonucleotides, which are in blocked form, are removed from the solid support upon which they are elaborated such as by ammonium hydroxide treatment. Further basic treatment deblocks and cyclizes the imidazole carboxamide into a 3-deaza-3-(reactive functionality)-guanine residue within the desired oligonucleotide sequence. Alternately, cleavage from the support with concentrate ammonium hydroxide directly cyclizes the imidazole carboxamide to the 3-deaza-guanine.

Alkylation of the imidazole active methylene with α-halo-α-acetaldehyde dimethylketal or α-halo-methyl-[reactive functionality] ketone with subsequent amination provides imidazole carboxamides. These can be converted to 5'-DMT-3+-cyanoethylphosphoramidites and inserted into sequence specific oligonucleotides. Basic treatment as above removes the oligonucletides from the solid support and cyclizes the imidazole moiety to a 3-deaza-3-[reactive functionality]-guanine. Further cyclization between the resulting N-2-exocyclic amine group and the aldehydic or ketonic carbonyl provides tricyclic heterocycle with reactive functionality, (pyrrolo[2,3-β]-imidazo [2,3-δ]pyridin-2-one (5H)-7-(or 8)-[reactive functionality]).

Direct deoxyribosylation of 6-isobutryl pyrrolo [2,3-β] imidazo [2,3-δ] pyridine 7-(or 8)-[reactive functionality] provides the 1-(2'-deoxy-β-D-erythro-pentofuransyl) derivative after basic deblocking of the toluoyl groups. The tricyclic heterocycle can be obtained from the alkylation of the tetrahydropyranyl derivative of methyl 5-cyanomethylimidazole 4-carboxylate in accordance with the procedure of the *Journal of Medicinal Chemistry*, Vol. 21, p. 1212 (1978), with α-halo-α-[reactive functionality]-acetaldehyde dimethylketals or α-halomethyl-[reactive functionality] ketones with subsequent amination. Acid treatment removes the tetrahydropyranyl blocking group and reducing conditions provides the 7,8-di-hydro 7-(or 8)-[reactive functionality] tricyclic heterocycle. The dihydropyrrole ring nitrogen can be protected with an isobutryl group. The 5'-DMT-3' -phosphoramidite-6-isobutryl nucleoside can be inserted into sequence-specific oligonucleotides via standard automated synthesis. Oligonucleotides prepared in this manner contain a pyrrolo[2.3-b]imidazo[2,3-d]pyridin-4-one(5H)-7-(or 8)-[reactive functionality], the 7,8-dihydro ring replacing a normal guanine residue.

Tether functionalities attached to the 3-position of 3-deaza-adenine modified oligonucleotides can be obtained such as by a multistep synthesis involving the attachment of reactive functionalities to the methylene moiety of the tetrahydropyranyl derivitive of dimethyl 5-carboxymethylimidazole-4-carboxylates. See *The Chemistry of Heterocyclic Compounds,* A. Weissberger, Ed., Imidazole and Derivatives, Part 1, Interscience, N.Y. (1953). Reactive functionalities having suitable leaving groups such as halogens, sulfonates, trichloroacemidates or conjugated double bond systems are employed. The modified imidazoles can be aminated with ammonium/heat forming the 3-deaza-3-(reactive functionality)-1-(or 3)-tetrahydropyranylxanthanines. These can be chlorinated with phosphoryl chloride to afford the 2,6-dichloro-3-deazapurines substituted in the 3-position. These compounds can be selectively aminated with ammonia, subjected to catalytic hydrogenolysis to remove the chlorine atom, and then protected with a conventional diphenylcarbamoyl group. Deoxyribosylation of these compounds under basic conditions with 3,5-di-O-toluoyl-α--D-erythro-pentofuranosyl chloride followed by selective deblocking of the sugar blocking groups provides 4-(di-phenylcarbamoyl)-1-(2-deoxy-β-D-erythro-pentofuranosyl)-7-[reactive functionality] imidazo [4,5-d] pyridines. These can be converted in conventional fashion to their 5'-DMT-3'-cyanoethylphosphoramidites and incorporated into oligonucleotides.

In order to attach tethered functionality in the 2'-position of ribo-oligonucleotides several exemplary synthetic procedures were devised.

Synthesis 1. Nucleophilic Displacement of 2'-Leaving Group in Arabino Purine Nucleosides.

Nucleophilic displacement of a leaving group in the 2'-up position (2'-deoxy-2'-(leaving group)arabino sugar) of adenine or guanine or their analog nucleosides can be so employed. General synthetic procedures of this type have been described by M. Ikehara et al., *Tetrahedron* Vol. 34 pp. 1133–1138 (1978); ibid., Vol. 31, pp. 1369–1372 (1975); *Chemistry and Pharmaceutical Bulletin,* Vol. 26, pp. 2449–2453 (1978); ibid., Vol. 26, pp. 240–244 (1978); M. Ikehara *Accounts of Chemical Research,* Vol. 2, pp. 47–53 (1969); and R. Ranganathan *Tetrahedron Letters,* Vol. 15, pp. 1291–1294 (1977). Thus β-D-arabinofuranosyl derivatives of guanine, adenine, cytosine, and thymine (Aldrich Chemical Co.) can be protected as the N2-isobutryl, N6-benzoyl, and N4-benzoyl, respectively, by known procedures. Simultaneous protection of the 3',5'-hydroxyls of the arabinofuranosyl nucleosides can be accomplished with 1,3-dichloro-1,1,3,3-tetraisopropyldisiloxane according to the known procedure set forth in *Nucleic Acid Chemistry, Improved and New Synthetic Procedures, Methods, and Techniques,* Part 3, page 229 (1986). The 2'-hydroxy group is activated towards nucleophilic displacement by treatment with trichloroacetonitrile and sodium hydride, *Tetrahedron Letters.,* Vol. 23, pp. 409–412 (1982), or trifluoromethylsulfonic acid anhydride and sodium hydride. These leaving groups can be displaced with inversion by substituted hetero-atoms such as nitrogen, sulfur, oxygen, or selenium to provide tethered reactive functionality in the 2'-position of the 3',5'-silyl blocked nucleosides. These nucleosides can then be deblocked such as by fluoride ion and converted to their 5'-DMT-3'-cyanoethylphosphoramidites for insertion into oligonucleotides.

Synthesis 2. Nucleophilic Displacement of 2,2'-Anhydro Pyrimidines.

Nucleosides thymine, uracil, cytosine or their analogs are converted to 2'-substituted nucleosides by the intermediacy of 2,2'-cycloanhydro nucleoside as described by J. J. Fox, et al., *Journal of Organic Chemistry,* Vol. 29, pp. 558–564 (1964).

Synthesis 3. 2'-Coupling Reactions.

Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H as per the procedure of Inoue, et al., *Nucleic Acids Research* Vol. 15, pp. 6131–6148 (1987).

Synthesis 4. 2-Deoxy-2-substituted Ribosylations.

2-Substituted-2-deoxyribosylation of the appropriately protected nucleic acid bases and nucleic acids base analogs has been reported by E. T. Jarvi, et al., *Nucleosides & Nucleotides* Vol. 8, pp. 1111–1114 (1989) and L. W. Hertel, et al., *Journal of Organic Chemistry* Vol. 53, pp. 2406–2409 (1988).

Synthesis 5. Enzymatic Synthesis of 2'-Deoxy-2'-Substituted Nucleosides.

The 2-Deoxy-2-substituted glycosyl transfer from one nucleoside to another with the aid of pyrimidine and purine ribo or deoxyribo phosphorolyses has been described by J. R. Rideout and T. A. Krenitsky, U.S. Pat. No. 4,381,344 (1983).

Synthesis 6. Conversion of 2'-Substituents Into New Substituents.

2'-Substituted-2'-deoxynucleosides are converted into new substituents via standard chemical manipulations. For example, S. Chladek et al., *Journal of Carbohydrates, Nucleosides & Nucleotides* Vol. 7, pp. 63–75 (1980) describes the conversion of 2'-deoxy-2'-azidoadenosine, prepared from arabinofuranosyladenine, into 2'-deoxy-2'-aminoadenosine.

Synthesis 7. Free Radical Reactions.

Conversions of halogen substituted nucleosides into 2'-deoxy-2'-substituted nucleosides via free radical reactions has been described by K. E. B. Parkes and K. Taylor, *Tetrahedron Letters* Vol. 29, pp. 2995–2996 (1988).

Synthesis 8. Conversion of Ribonucleosides to 2'-Deoxy-2'-Substituted Nucleoside.

Appropriately 3',5'-sugar and base protected purine and pyrimidine nucleosides having a unprotected 2'-hydroxyl group are converted to 2'-deoxy-2'-substituted nucleosides by the process of oxidation to the 2'-keto group, reaction with nucleophilic reagents, and finally 2'-deoxygenation. Procedures of this type have been described by F. De las Heras, et al., *Tetrahedron Letters* Vol. 29, pp. 941–944 (1988).

Functionality in the 1'-position of a 2'-deoxyribofuranosyl moiety can be obtained from the nucleoside antibiotic, psicofuranine, which differs from adenosine by having a hydroxyl methyl group in the 1'-position. The 3',5'-hydroxyls can be protected by 1,3-dichloro-1,1,3,3-tetraisopropyldisiloxane, followed by protection of the 1'-hydroxymethyl with a triphenylmethyl group. The 2'-hydroxy group can be deoxygenated by formation of the thiocarbonate and subsequent treatment with tri-n-butyl hydride according to known procedures. See,*J. Amer. Chem. Soc.,* Vol. 105, pp. 4059–4065 (1983). The N6-amino group can be benzoylated, the trityl group removed with acid, and the resulting primary hydroxy group converted to the trichloroacetamidate with sodium hydride and trichloroacetonitrile. Displacement reactions with various tether/reactive functionality can be readily accomplished in the next step. The disilyl blocking group can be removed with fluoride ion and the resulting 2'-deoxy nucleoside converted to the 5'-DMT-3'-phosphoramidite for insertion into oligonucleotides via known procedures.

Reactive functionality in the 4'-position can be obtained from 2'-deoxynucleotides (Sigma Chemical Company) by selectivity protecting the 5'-hydroxyl with the t-butyldimethyl silyl group and the 3'-hydroxyl with the tetrahydropyranyl group. The silyl group is removed with fluoride ion. The Pfitzner-Moffatt oxidation procedure,*Journal of American Chemical Society,* Vol. 85 p. 3027 (1963), can be used to provide the 5'-aldehydes which are then treated with formaldehyde affording the 4'-hydroxymethyl derivatives. *Tetrahedron Letters,* 435 (1977). These deoxynucleosides, as their 5'-trityls, can be converted to the 4'-trichloroacetamides with trichloroacetonitrile and sodium hydride. Reactive functionality are then placed in the 4'-position via nucleophilic displacements of the acetamidates. Acid treatment removes the blocking groups in the 5' and 3'-positions. These can be subsequently prepared as the 5'-DMT-3'-cyanoethylphosphoramidite and inserted into modified oligonucleotides via a automated, solid phase DNA synthesizers.

The synthesis of abbreviated guanosine nucleosides (monocyclics) substituted with reactive functionality such as 2'-deoxy-2-imidazolone-4-carboxamide 5-reactive functionality can be prepared from the reaction of ethyl 2-bromomethyl-2-imdazolone (1H,3H)-4-carboxylate with reactive functionality nucleophiles such as histamine, hydroxyethylimidazolyl, and mercaptoethylimidazolyl. Other heteroatomic nucleophiles, neutral or anionic, with attached reactive functionality may be employed as well. These compounds are protected as the 2-o-diphenylcarbamoyl derivatives with diphenylcarbamoyl chloride and base and 2'-deoxyribosylated with 3,5-di-o-(4-methylbenzoyl)-α-D-erythro-pentofuranosyl chloride. The 3',5'-dihydroxys of the sugar are selectively deblocked with base and reprotected as the 5'-DMT-3'-cyanoethylphosphoramidite. These imidazole nucleosides can be inserted into oligonucleotides according to known procedures. The strong basic conditions required to remove the acyl blocking groups on the cytosine, adenine, guanine, and imidazole bases convert the 4-imidazole carboxylate to the 4-carboxamide moiety.

Reactive functionality in the 5-position of 4-aminoimidazol-2-one modified oligonucleotides can be prepared by the deoxyribosylation of 2,5-dibromo-4-nitroimidazole, *Journal of Chemical Society* Vol. 121, p. 947 (1922), with 3,5-O-(p-methyl-benzoyl)-α-D-erythropentofuranosy chloride under basic conditions. Selective displacement of the 5-bromo group with nucleophilic reactive functionality afforded a variety of bromonitrodeoxynucleotides. Displacement of the 2-bromo group and subsequent reduction of the 4-nitro group provided 4-amino-1-(2-deoxy-β-D-erythro-pentofuranosy)imidazol-2-one(3H) which can be inserted into oligonucleotides via their 5'-DMT-3'-cyanoethylphosphoramidites.

Reactive functionality placed in the 3-position of 2-aza-3-deaza-2'-deoxyadenosine can be prepared from the deoxyribosylation of 4,7-dichloroimidazo[4,5-d]pyridazine, *J. Org. Chem.,* Vol. 23 p. 1534 (1958) with 3,5-di-O-(methylbenzoyl)-α-D-erythropentofuranosyl chloride under basic conditions. This is aminated with liquid ammonia to provide 4-amino-7-chloro-1-(2-deoxy-βD-erythro-pento furanosyl)imidazo[4,5-d]pyridazine. Reactive functionality are then inserted in the 7-position by nucleophilic displacement of the chlorine atom. Examples are heteroatoms such as nitrogen, oxygen, sulfur, selenium, etc., attached to the reactive functionality placed on the 7-carbon position. Protection of 4-amino-1-(2-deoxy-β-D-erythropentofuranosyl)-7-chloroimdazo-[4,5-d] pyridazine with t-butyldimethylsilyl groups followed by displacement of the chlorine atom with triphenylphosphorane reagents affords carbon-linked reactive functionality. The 7-position tethered reactive functionality 4-amino-1-(2-deoxy-β-D-erythropentofuranosyl-7-chloroimidazo[4,5-d]pyridazines are then inserted, via 5'-DMT-3'-phosphoramidites, into oligonucleotides.

In order to attach reactive functionality in the 2'-position of σ-arabinofuranosyloligonucleotides, silylated hetero cycles can be glycosylated with 1-O-acetyl-2,3,5-tri-O-benzoyl-D-arabinofuranose (Pfanstiehl Laboratories, Inc.) with Lewis acid catalysis. The benzoyl groups of the sugar of the resulting α-nucleoside are selectively removed with methanolic ammonia; the 3',5'-hydroxyls are then reprotected with 1,1,3,3-tetraisopropyldisiloxane. Reactive functionality is attached to the 2'-hydroxyl group via the Mitsunobu reaction. Synthesis 1 (1981). Deprotection with fluoride ion then affords the 2'-[tethered reactive functionality]-1-(α-D-arabinofuranosyl) nucleosides, which can be inserted into oligonucleotides via their 5'-DMT-3'-cyanoethylphosphoramidites.

Functionality may be attached to the 6' -position of the natural occurring nucleosides or base analogs thereof by direct nucleophilic attack of protected heterocycles on carbocyclic 3,5-di-O-benzyl-2-deoxy-α-1,6-epoxy-D-erythropentofuranose as set forth by K. Biggadike, et al., *J. Chem. Soc., Chem. Commun.,* 1083 (1987). Reactions of this type will afford carbocyclic 2'-deoxynucleosides with a hydroxyl group located at the 6'-position on the a face of the cyclopentane ring. Functionality can now be attached to the unprotected hydroxyl group by direct coupling (i.e., Mitsunobu conditions, triphenylphosphine/DEAD) or double displacement reactions. Debenzylation of compound of this type, followed by formation of the 5'-DMT and the 3'-β-cyanoethoxy diisopropyl-phosphoramidite by standard procedures provides monomers which can be inserted into oligonucleotides by solid phase, automated DNA synthesizers.

Pyrimidine C-nucleoside type compounds which have the deoxyribofuranosyl moiety located at the 4-position have the ring nitrogen atom in the 3-position available to attach functionality. These type nucleosides may be synthesized by a displacement, via a 4-carbanion of the protected pyrimidine, of the chlorine atom of 3,5-di-O-toluoyl-2-deoxy-α-erythropentofuranosyl chloride. G. D. Daves and C. C. Cheng, *Progress in Medicinal Chemistry,* Vol. 14, pp. 304–349 (1978). Appropriate functionality can be placed in the 3-position of the protected pyrimidine by commonly known procedures. Selective removal of the toluoyl groups and subsequent DMT and phosphitylation will provide desired monomers for insertion into oligonucleotides.

Quinazoline deoxyribosides with functionality located in the 8-position may be obtained by palladium mediated coupling of furanoid glycals with 7-tributylstannylated heterocycles as set forth by R. O. Outten and G. D. Daves, Jr. in the *Journal of Organic Chemistry,* Vol. 52, p. 5064 (1987).

Without desiring to be bound by any particular theory of operation, it is believed that the reactive RNA cleaving functionalities, described in this invention work by mechanisms involving either:

1. phosphodiester bond cleavage via acid/base catalysis;
2. backbone sugar cleavage;
3. base alkylation cleavage; or
4. sugar alkylation, ie. 2'-hydroxyl, cross-linking.

One important aspect of this invention is the position and orientation of an appropriate reactive functionality minor groove or side formed between the targeting portion of this invention and the target RNA. A summary of this is provided in Table 1, and each reactive functionality is described according to the suggested mechanism of action.

TABLE 1

| EXAMPLE NUMBER | REACTION | MECHANISM | PREFERRED FUNCTIONALITY | PREFERRED LOCATION |
|---|---|---|---|---|
| 1 | Phosphodiester bond cleavage | 2' proton abstraction on ribose sugar | Organic base | Minor groove |
| 2 | Phosphodiester bond cleavage | 2' proton abstraction on ribose sugar | Coordination complex | Minor groove |
| 3 | Phosphodiester bond cleavage | 5' proton donation on ribose sugar | Organic acid | Either |
| 4 | Phosphodiester bond cleavage | Electrophilic activation of phosphate | Coordination complex with net positive charge | Either |
| 5 | Oxidative cleavage of ribose sugar | Oxygen radical generation & hydrogen abstraction from ribose | Organic radical generating moiety | Minor groove |
| 6 | Oxidative cleavage of ribose sugar | Oxygen radical generation & hydrogen abstraction from ribose | Coordination complex | Minor groove |
| 7 | Electrophilic attack on bases | Base removal | Alkylating agent | Minor groove |
| 8 | Electrophilic attack on 2'-hydroxyl group of RNA | Covalent cross-link | Alkylating agent | Minor groove |

Phosphodiester bond cleavage can be accomplished by strategically positioning either proton accepting, proton donating, or electron accepting functional groups, represented by X,Y, and Z respectively in Scheme 1 adjacent to such phosphodiester bonds.

SCHEME 1

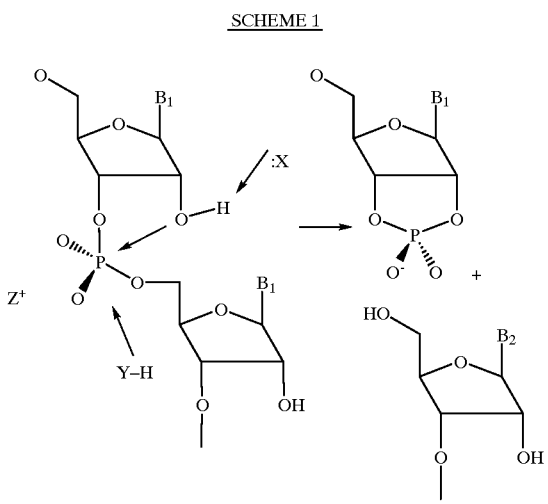

Where $B_1$ and $B_2$ are base units. In some applications, one of the chemical groups is sufficient to catalyze RNA cleavage. However, in other applications of the invention, the combination of two or even three groups may be preferred. Artisans in the field will have great latitude in selecting the specific reactive functionalities X,Y, and/or Z. There is also great latitude in the election to use one or more reactive functionalities in the same molecule.

Examples of proton accepting functionalities which can form the phosphodiester bond cleaving reactive moiety in accordance with this invention include heteroatomic bases which are capable of base-catalysis of the phosphodiester bond. Ammoniacal species generally, such as alkyl and arylamines and alkyl and arylhydrazines, are preferred. Heterocyclic nitrogenous compositions, especially imidazoles, pyridines, azines, oxazoles, thiazoles, and the like are more preferred. Of these species, the 1-, 2-, and 5-imidazoles are most preferred. Each of these compositions may be widely substituted in order to vary the electronegativity of the various nitrogen atoms available for base catalysis. Alkyl and aryl amidium species are also most preferred. Carboxylic acid and their derivatives of the above ammoniacal species are most preferred.

Another type of species which may be useful as the proton accepting function in the compositions and methods of the present invention are coordination complexes. These are represented as Example 2 of Table 1. Coordination complexes are useful in this regard by having a metal ion with ligands designed so that not all of the coordination sites on the metal are occupied by the ligands, thus leaving one or more empty sites. In solution, the empty sites are occupied by water molecules leading to —OH moieties being coordinated to the metal. The —OH group can function as a base to abstract the 2' proton and effect phosphodiester bond cleavage. The selection of ligands for coordination with the metal ions should follow three important considerations. First, they should be capable of holding the metal near the target RNA and "steer" the hydroxyl group on the coordination complex (which can be represented as HO-ML) near to the 2' proton which is to be abstracted. The ligands are designed to interact favorably with the duplex formed between the compositions of the invention and the target RNA.

A second important function of the ligands is to regulate the pKa of the hydrolyzed metal. The coordination complex, HO-ML, can function to catalyze the cleavage of the target RNA not only by providing a hydroxyl group in the proper orientation for proton abstraction, but at the proper pKa. The proper pKa depends upon the pH which exists during the practice of the methods of the invention. The proper pKa to be maintained is preferably such that the hydroxyl group is sufficiently ionized to allow for proton abstraction, but not so low that the hydroxyl group has no tendency to abstract the proton. The ligands are preferably selected in accordance with this invention as to adjust the pKa of the hydrolyzed metal complex to achieve these ends.

The third important function of the ligands is to regulate redox reactions. In the case of metal ions that have two or more accessible oxidation states, the ligands stabilize one oxidation state in preference to others and prevent or retard the generation of diffusible, toxic, usually oxygen-containing, radicals.

Other coordination complexes, including some which are intended to generate diffusible oxygen-containing radicals, can be used in accordance with other embodiments of this invention, but these are believed to cleave the target RNA by a different mechanism described hereinafter.

The metal ions preferred for use in this invention include $Ca^{+2}$, $Sc^{+3}$, $Cr^{+3}$, $Mn^{+2}$, $Fe^{+3/+2}$, $Co^{+2/+1}$, $Zn^{+2}$, $Al^{+3}$, $Ga^{+3}$, $Rh^{+3}$, $Mg^{+2}$. Ligands include multidentate carboxylates, aminos, hydroxamic acids, catecholates, heterocyclic amines and peptides. Ligands of these types include, but are not limited to, EDTA, NTA, bipyridyl, phenanthroline, desferrioxamine, enterobactin (and its analogs), gly gly his and gly gly gly.

These reactive functionalities are attached to the balance of the molecule comprising the compositions of the invention in any convenient way, usually through an amide function. Persons of ordinary skill in the art will have no difficulty in selecting appropriate means for the attachment of the reactive functionalities to the targeting portions of the compositions of these invention through convenient tether means.

In accordance with other embodiments of the invention, proton donating, acidic media may be employed as reactive functionalities in order to effect acid catalysis of the hydrolysis of the phosphodiester bonds. Such functionalities are depicted as group Y of Scheme 1 and particular embodiments are presented in Example 3 of Table 1. Any of a large number of acids are believed to be effective in donating protons for the acid catalyzed hydrolysis of phosphodiester bonds in accordance with this invention. Such acid functions include carboxylic acids and heterocyclic acids.

Among the class of heterocyclic acidic functionalities tetrazoles and triazoles are preferred. It is known that several of the nitrogen atoms in the triazoles and tetrazoles possess substantial acidity. It is believed that they may be used for catalysis of such hydrolysis reactions. The acidic functionalities are attached to the targeting portion of the compositions, as are all of the reactive species in accordance with this invention.

It is believed that the hydrolysis of phosphodiester bonds in nucleotides proceeds through a pentacoordinate structure on the phosphorus atom having trigonal bipyrimidal geometry and a charge of –2. The presence of an electropositive species which can stabilize this transition state is believed to assist, catalytically, in the cleavage reaction. Such species may be considered to be an electropositive moiety and is denominated as group Z in Scheme 1. Examples of such functionalities are presented in Example 4 in Table 1. These reactive functionalities may comprise a coordination complex having two empty sites The two empty sites are believed to coordinate with and stabilize the phosphorus transition state. Among the reactive functionalities which may be useful for this purpose are those containing metal ions such as: $Ca^{+2}$, $Sc^{+3}$, $Cr^{+3}$, $Mn^{+2}$, $Fe^{+3/+2}$, $Co^{+2/+1}$, $Zn^{+2}$, $Al^{+3}$, $Ga^{+3}$, $Rh^{+3}$, $Mg^{+2}$. Ligands which are suitable for the formation of such coordination complexes include multidentate carboxylates, aminos, hydroxamic acids catecholates, heterocyclic amines, and peptides.

Radical forming moieties, especially those which form oxygen radicals, may also be employed as the reactive functionalities of the compositions of this invention. When radical generating species are used as the reactive portions of the compositions of the present invention, it is believed to be necessary that they be delivered into the minor groove of the complex formed between the compositions and the target RNA. Minor groove delivery is believed to be essential to their effective operation in high yield without adverse, and potentially toxic side effects. It is known that prior employment of radical generating species has been met by migration of toxic compounds either comprising or related to the radicals formed, with toxicity and damage to other intracellular species resulting. It is believed that minor groove delivery of these species obviates or at least substantially diminishes these negative effects. A large number of organic radical generating species such as the quinones, coumarins, and other agents which are capable of producing active oxygen may be employed.

Coordination complexes may also be employed as radical-generating agents in the minor groove. It is known that certain metals which have more than one accessible oxidation state, when complexed by appropriate ligands and in the presence of reducing agents and oxygen, will generate oxygen radical species capable of cleaving oligonucleic acid targets. As with the organic radical generating species, it is necessary to deliver the coordination complex into the minor groove of the hybrid formed between the compositions and the target RNA.

Coordination complexes useful in generating radical species include complexes of iron, copper, and molybdenum with ligands such as carboxylic acids, amines, hetero-cyclic nitrogen containing species such as phenanthrolines, dipyridyl, imidazole, or peptidyl ligands such as gly gly his, gly gly his lys, and gly gly gly gly, and hydroxamic acids. These ligands may be mixed to generate more effective combinations within the scope of this invention.

A further group of moieties which may serve as reactive portions of the compositions of the present invention are alkylating agents. Several classes of alkylating agents are known to persons of ordinary skill in the art including the N-mustard types which are generally $\beta,\beta$-haloethylamines. Other alkylating agents such as alpha-haloketones, sulfonyl halides, aziridines, allylic halides, epoxides, alkyl/aryl halides, and light activatible alkylating agents such as psoralines may also be employed. Michael reaction accepting compositions may also find utility in the practice of this invention.

A 2'-hydroxyl group of the targeted RNA, exposed in the minor groove or side, serves as a nucleophilic center for bond formation with tethered electrophilic functionality that also resides in the minor groove of the heteroduplex. Classes of electrophiles for attachment appropriately to nucleotides are listed above. Targeted RNA is inactivated by formation of covalent links between a modified oligonucleotide and the RNA 2'-hydroxyl group.

It has now been discovered from structure activity relationships studies that a significant increase in binding ($T_m$)s of certain 2'-sugar modified oligo-nucleotides to its RNA target (complement) is correlated with an increased "A" type conformation of the hetero-duplex. Furthermore, absolute fidelity of the modified oligonucleotides is maintained. The increased binding of our 2'-sugar modified sequence-specific oligonucleotides provides superior potency and specificity compared to phosphorus modified antisense oligonucleotides such as methyl phosphonates, phosphorothioates, phosphate triesters and phosphoramidites as known in the literature.

The only structural difference between DNA and RNA duplexes is an hydrogen atom in the 2'-position of the DNA ribofuranosyl moieties versus a hydroxyl group in the 2'-position of the RNA ribofuranosyl moieties (assuming that the presence or absence of a methyl group in the uracil ring system has no effect). However, gross conformational differences exist between DNA and RNA duplexes.

It is known from x-ray diffraction analysis of nucleic acid fibers, Arnott and Hukins, *Biochemical and Biophysical Research Communication*, Vol. 47, pp. 1504–1510 (1970), and analysis of crystals of double-stranded nucleic acids that DNA takes a "B" form structure and that RNA only takes the much more rigid "A" form structure. The difference between the sugar puckering (C2' endo for "B"-form DNA and C3' endo for "A"-form RNA) of the nucleoside monomeric units of DNA and RNA is the major conformational difference between double-stranded nucleic acids.

The primary contributor to the pentofuranosyl moiety conformation is the nature of the substituent in the 2'-position. Thus, the population of the C3'-endo form increases with respect to the C2'-endo as the electronegativity of the 2'-substituent increases. For example, among 2'-deoxy-2'-halo-adenine nucleosides, the 2'-fluoro derivative exhibits the largest population (65%) of C3'-endo, and the 2'-iodo shows the lowest (7%). Those of the adenosine (2'-OH) and deoxyadenosine (2'-H) are 36% and 19%, respectively. Furthermore, the effect of the 2'-fluoro group of adenine dinucleotides (2'-deoxy-2'fluoroadenosine-2'-deoxy-2'-fluoroadenosine or uridine) is further correlated to the stabilization of the stacked conformations more than ribo or deoxyribo modified dimers. Research indicates that the dinucleosides phosphates have a stacked conformation with a geometry similar to that of A-A but with a greater extent of base-base overlapping than A-A. It was assumed that the highly polar nature of the C2'-F bond and the extreme preference for C3'-endo puckering may stabilize the stacked conformation in an "A" structure.

Data from UV hypochromicity, circular dichroism, and 'H NMR also indicate that the degree of stacking decreases as the electronegativeness of halogen decreases. Furthermore, a sterical bulkiness in the 2'-position is better accommodated in an "A" form duplex than a "B" form duplex.

Thus, a 2'-substituent on the 3'-nucleotidyl unit of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

The 2'-iodo substituted nucleosides possess the lowest C3'-endo population (7%) of the halogen series. Thus, on steric effects alone, one would predict an 2'-iodo or similar groups would contribute stacking destabilizing properties and thus reduced binding ($T_m$)s for antisense oligonucleotides. However, the lower electronegativeness and high hydrophobic attractive forces of the iodine atom and similar groups complicates the ability to predict stacking stabilities and binding strengths.

Studies with the 2'-OMe modification of 2'-deoxy guanosine, cytidine, and uridine dinucleoside phosphates exhibit enhanced stacking effects with respect to the corresponding unmethylated species (2'-OH). In this case, the hydrophobic attractive forces of the methyl group tend to overcome the destablilizing effects of its sterical bulkiness (hindrance).

2'-Fluoro-2'-deoxyadenosine has been determined to have an unusually high population of 3'-endo puckering among nucleosides. Adenosine, 2'-deoxyadenosine, and other derivatives typically have population below 40% in the 3'-endo conformer. It is known that a nucleoside residue in well-stacked oligonucleotides favors 3'-endo ribofuranose puckering.

Melting temperatures (complementary binding) are increased with the 2'-substituted adenosine diphosphates. It is not clear whether the 3'-endo preference of the conformation or the presence of the substituent is responsible for the increased binding. However, as noted, greater overlap of adjacent bases (stacking) can be achieved with the 3'-endo conformations.

The present novel approach to obtaining stronger binding is to prepare antisense RNA mimics to bind to the targeted RNA. Therefore, a random structure-activity relationship approach was undertaken to discover nuclease resistant antisense oligonucleotides that maintained appropriate hybridization properties.

A series of 2'-deoxy-2'-modified nucleosides of adenine, guanine, cytosine, thymidine and certain analogs of these bases have been prepared and have been inserted as the modified nucleosides into sequence-specific oligonucleotides via solid phase nucleic acid synthesis. The novel antisense oligonucleotides were assayed for their ability to resist degradation by nucleases and to possess hybridization properties comparable to the unmodified parent oligonucleotide. Initially, small electronegative atoms or groups were selected because these type are not likely to sterically interfere with required Watson-Crick base pair hydrogen bonding (hybridization). However, electronic changes due to the electronegativeness of the atom or group in the 2'-position may profoundly effect the sugar conformation. During our structure activity relationship studies we discovered that the sugar modified oligonucleotides hybridized to the targeted RNA stronger than the unmodified (2'-deoxyribosyl type).

In further embodiment of this invention, a linking moiety has been devised to allow the direct attachment of a modified unit to the terminal position of the 3'-end of the modified oligonucleotides. Thus, an ester, or more preferably a bromomethylketo group, is attached to the 3'-hydroxyl of a modified 2'-modified nucleoside having its 5'-hydroxyl protected with a dimethoxytriphenylmethyl group and the heterocycle benzoylate of the cytosine series. If the required targeting sequence has a terminal 3'-thymine or cytosine base, the desired modified thymine or cytosine base containing the bromomethylketo linker is utilized as the first monomer to attach to the control pore glass (CPG) solid support which contains a normal nucleoside attached via its 3'-hydroxyl group. The base sensitive ester linkage attaching the 2'-modified nucleoside to the nucleoside attached to the CPG is cleaved under the usual concentrated ammonium hydroxide conditions that are utilized to remove the oligonucleotide from the CPG support. This will allow the modified oligonucleotide to have a 2'-modified unit at its terminal, 3'-end.

Cleavage of oligonucleotides by nucleolytic enzymes require the formation of an enzyme-substrate complex, or in particular a nuclease-oligonucleotide complex. The nuclease enzymes will generally require specific binding sites located on the oligonucleotides for appropriate attachment. If the oligonucleotide binding sites are removed or hindered such that the nucleases will not attach to the oligonucleotides, the nuclease resistant oligonucleotides result. In the case of restriction endonucleases that cleave sequence-specific palindromic double-stranded DNA, certain binding sites such as the ring nitrogen in the 3- and 7-positions have been identified as required binding sites. Removal of one or more of these sites or hindering the nuclease approach to these particular positions within the recognition sequence has provided various levels of resistance to the specific nucleases.

The oligonucleotides or oligonucleotide analogs of this invention can be used in diagnostics, therapeutics, and as research reagents and kits. For therapeutic use the oligonucleotide is administered to an animal suffering from a disease affected by some protein. It is preferred to administer to patients suspected of suffering from such a disease with amounts of oligonucleotide which are effective to reduce the symptemology of that disease. It is within the scope of a person's skill in the art to determine optimum dosages and treatment schedules for such treatment regimens.

It is generally preferred to apply the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

The following procedures and examples illustrate the practice of this invention. These procedures and examples are not to be construed as limiting the invention.

Once nucleotides of the invention have been prepared, they can then subsequently be incorporated into oligonucleotides of the invention.

Oligonucleotides of the invention are synthesized by the standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries, M. Caruthers, *Oligonucleotides. Antisense Inhibitors of Gene Expression.*, pp. 7–24, J. S. Cohen, ed. (CRC Press, Inc. Boca Raton, Fla., 1989), are used in with these synthesizers to provide the desired oligonucleotides. The Beaucage reagent, *Journal of American Chemical Society*, Vol. 112, pp. 1253–1255 (1990) or elemental sulfur, S. Beaucage et al., *Tetrahedron Letters*, Vol. 22, pp. 1859–1862 (1981), is used with phosphoramidite or hydrogen phosphonate chemistries to provide substituted phosphorothioate oligonucleotides.

In preparing certain of the compounds of the invention fugitive masking groups have been used. Such masking groups allow for ease of synthesis of the compounds. The masking groups are subsequently converted to the desired functionality. Such conversion preferably occurs during a standard deblocking step for a later reaction. As an example of use of this procedure is the use of phthalimide group for the introduction of an amino functionality. Alkyl phthalimides are attached at the proper position in a compound of interest, as for example a nucleoside, via a suitable intermediate such as an N-(haloalkyl)phthalimide. Upon completion of the synthesis of the compound of interest it is then used as a structural nucleotide for oligonucleotide synthesis utilizing standard oligonucleotide synthetic techniques on a nucleotide synthesizer. After the desired oligonucleotide is completed, it is cleaved from the synthesizer support and in doing so the cleaving reagent also converts the alkylphthalimide to the desired alkylamine. The above procedure can be expanded to attach longer chain polyamino functionalities to the oligonucleotides of the invention. Nucleotides or oligonucleotides having a first alkylamino functionality are treated with a further N-(haloalkyl) phthalimide. The extended functionality is then treated to yield the terminal amine group. This can be repeated to further extend the polyamino functionality as desired. Alternately, the extended polyamino functionality is first synthesized and reacted with the first alkylamino functionality to form the polyamino functionality.

Procedure 1—Hybridization Analysis

A. Evaluation of the thermodynamics of hybridization of modified oligonucleotides.

The ability of the modified oligonucleotides of the invention to hybridize to their complementary RNA or DNA sequences was determined by thermal melting analysis. The RNA complement was synthesized from T7 RNA polymerase and a template-promoter of DNA synthesized with an Applied Biosystems, Inc. 380B nucleic acid synthesizer. The RNA species was purified by ion exchange using FPLC (LKB Pharmacia, Inc.). Natural antisense oligonucleotides or those containing the modifications at specific locations were added to either the RNA or DNA complement at stoichiometric concentrations and the absorbance (260 nm) hyperchromicity upon duplex to random coil transition was monitored using a Gilford Response II spectropho-tometer. These measurements were performed in a buffer of 10 mM Na-phosphate, pH 7.4, 0.1 mM EDTA, and NaCl to yield an ionic strength of 10 either 0.1 M or 1.0 M. Data was analyzed by a graphic representation of $1/T_m$ vs $\ln[Ct]$, where $[Ct]$ was the total oligonucleotide concentration. From this analysis the thermodynamic parameters were determined. Based upon the information gained concerning the stability of the duplex of hetero-duplex formed, the placement of modified pyrimidine into oligonucleotides were assessed for their effects on helix stability. Modifications that drastically alter the stability of the hybrid exhibit reductions in the free energy (delta G) and decisions concerning their usefulness as antisense oligonucleotides were made.

B. Fidelity of hybridization of modified antisense oligonucleotides

The ability of the modified antisense oligonucleotides of the invention to hybridize with absolute specificity to the targeted mRNA was shown by Northern blot analysis of purified target mRNA in the presence of total cellular RNA. Target mRNA was synthesized from a vector containing the cDNA for the target mRNA located downstream from a T7 RNA polymerase promoter. Synthesized mRNA was electrophoresed in an agarose gel and transferred to a suitable support membrane (i.e. nitrocellulose). The support membrane was blocked and probed using [$^{32}$P]-labeled antisense oligonucleotides. The stringency was determined by replicate blots and washing in either elevated temperatures or decreased ionic strength of the wash buffer. Autoradiography was performed to assess the presence of heteroduplex formation and the autoradiogram quantitated by laser densitometry (LKB Pharmacia, Inc.). The specificity of hybrid formation was determined by isolation of total cellular RNA by standard techniques and its analysis by agarose electrophoresis, membrane transfer and probing with the labeled modified oligonucleotides. Stringency was predetermined for the unmodified antisense oligonucleotides and the conditions used such that only the specifically targeted mRNA was capable of forming a heteroduplex with the 2'-modified oligonucleotide.

Procedure 2—Nuclease Resistance

A. Evaluation of the resistance of modified oligonucleotides to serum and cytoplasmic nucleases.

Natural phosphorothioate, and modified oligonucleotides of the invention were assessed for their resistance to serum nucleases by incubation of the oligonucleotides in media containing various concentrations of fetal calf serum or adult human serum. Labeled oligonucleotides were incubated for various times, treated with protease K and then analyzed by gel electrophoresis on 20% polyacrylamine-urea denaturing gels and subsequent autoradiography. Autoradiograms were quantitated by laser densitometry. Based upon the location of the modifications and the known length of the oligonucleotide it was possible to determine the effect on nuclease degradation by the particular modification. For the cytoplasmic nucleases, a HL60 cell line was used. A post-mitochondrial supernatant was prepared by differential centrifugation and the labeled oligonucleotides were incubated in this supernatant for various times. Following the incubation, oligonucleotides were assessed for degradation as outlined above for serum nucleolytic degradation. Autoradiography results were quantitated for comparison of the unmodified, the phosphorothioates, and the modified oligonucleotides.

B. Evaluation of the resistance of modified oligonucleotides to specific endo- and exo-nucleases.

Evaluation of the resistance of natural and 2'-modified oligonucleotides to specific nucleases (ie, endonucleases, 3',5'-exo-, and 5',3'-exonucleases) was done to determine the exact effect of the modifications on degradation. Modified oligonucleotides were incubated in defined reaction buffers specific for various selected nucleases. Following treatment of the products with proteinase K, urea was added and analysis on 20% polyacrylamide gels containing urea was done. Gel products were visualized by staining using Stains All (Sigma Chemical Co.). Laser densitometry was used to quantitate the extend of degradation. The effects of the modifications were determined for specific nucleases and compared with the results obtained from the serum and cytoplasmic systems.

Procedure 3—5-Lipoxygenase Anaylsis, Therapeutics and Assays

A. Therapeutics

For therapeutic use, an animal suspected of having a disease characterized by excessive or abnormal supply of 5-lipoxygenase is treated by administering oligonucleotide in accordance with this invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide compounds of this invention are also useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition as described in the following Examples at concentrations ranging as for instances from about 100 to about 500 ng per 10 Kg of total RNA in a buffer consisting, for example, of 50 mm phosphate, pH ranging from about 4–10 at a temperature from about 30 to about 50C. The cleaved 5-lipoxygenase RNA can be analyzed by agarose gel electrophoresis and hybridization with radiolabeled DNA probes or by other standard methods.

C. Diagnostics

The compounds of this invention will also be useful in diagnostic applications, particularly for the determination of the expression of specific mRNA species in various tissues or the expression of abnormal or mutant RNA species. In this example, the oligonucleotide compound targets a hypothetical abnormal mRNA by being designed complementary to the abnormal sequence, but would not hybridize to or cleave the normal mRNA.

Tissue samples can be homogenized, and RNA optionally extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which was cleaved by the invention compound, would not be bound to the support and therefore would be separated from the normal mRNA.

Several preferred embodiments of this invention are exemplified in accordance with the following examples. The target mRNA species for modulation relates to 5-lipoxygenase. Persons of ordinary skill in the art will appreciate that the present invention is no so limited, however, and that it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferrably use the human promyleocytic leukemia cell line HL60. These cells can be induced to differentiate into either a monocytic-like cell or neutrophil-like cell by various known agents. Treatment of the cells with 1.3% dimethyl sulfoxide, DMSO, is known to promote differentiation of the cells into neutrophils. It has now been found that basal HL60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of antisense oligonucleotides which interfere with 5-lipoxygenase synthesis in these cells.

A second test system for antisense oligonucleotides makes use of the fact that 5-lipoxygenase is a "suicide" enzyme in that it inactivates itself upon reacting with substrate. Treatment of differentiated HL60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Antisense oligonucleotides directed against 5-lipoxygenase can be tested for activity in two HL60 model systems using the following quantitative assays. The assays are described from the most direct measurement of inhibition of 5-lipoxygenase protein synthesis in intact cells to more downstream events such as measurement of 5-lipoxygenase activity in intact cells.

The most direct effect which antisense oligonucleotides exert on intact cells which can be easily be quantitated is specific inhibition of 5-lipoxygenase protein synthesis. To perform this technique, cells can be labelled with $^{35}$S-methionine (50 $\mu$Ci/mL) for 2 hours at 37° C. to label newly-synthesized protein. Cells are extracted to solubilize total cellular proteins and 5-lipoxygenase is immunoprecipitated with 5-lipoxygenase antibody followed by elution from protein A Sepharose beads. The immunoprecipated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of effective antisense oligonucleotide for 48 hours would reduce immunoprecipitated 5-lipoxygenase to 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL60 cells for 72 hours with an effective antisense oligonucleotide at 1 $\mu$M, 10 $\mu$M, and 30 $\mu$M would be as follows. Control cells oxidize 200 pmol arachidonic acid/5 min/106 cells. Cells treated with 1 $\mu$M, 10 $\mu$M, and 30 $\mu$M of an effective oligonucleotide would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris.HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 $\mu$L in the microtiter wells for 90 min. The antibodies were prepared by immunizing rabbits with purified human recombinant 5-lipoxygenase. The wells were washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer antisense oligonucleotide at 1 $\mu$M, 10 $\mu$M, and 30 $\mu$M would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL60 cells 48 hours following addition of DMSO to differentiate the cells into a neutrophil-like cell. Cells ($2 \times 10^5$ cells/mL) will be treated with increasing concentrations of antisense oligonucleotides for 48–72 hours in the presence of 1.3% DMSO. The cells are washed and resuspended at a concentration of $2 \times 10^6$ cell/mL in Dulbecco's phosphate buffered saline containing 1% delipidated bovine serum albumin. Cells are stimulated with 10 $\mu$M calcium ionophore A23187 for 15 min and the quantity of LTB4 produced from $5 \times 10^5$ cell determined by radioimmunoassay as described by the manufacturer.

Using this assay the following results would likely be obtained with a 15-mer antisense oligonucleotide (GCAAGGTCACTGAAG) SEQ ID NO: 1 directed to the 5-LO mRNA. Cells will be treated for 72 hours with either 1 $\mu$M, 10 $\mu$M or 30 $\mu$M oligonucleotide in the presence of 1.3% DMSO. The quantity of $LTB_4$ produced from $5 \times 10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the rat can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a rat ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Antisense oligonucleotides will be applied topically to both ears 12 to 24 hours prior to administration of arachidonic acid to allow optimal activity of the compounds.

An expected result using a 15-mer antisense oligonucleotide directed against rat 5-lipoxygenase corresponding to nucleotides 80–97 is given below. Both ears are pretreated for 24 hours with either 0.1 $\mu$mol, 0.3 $\mu$mol, or 1.0 $\mu$mol antisense oligonucleotide prior to challenge with arachidonic acid. Values are expressed as the mean for three animals per concentration. Inhibition of polymorphonuclear cell infiltration for 0.1 $\mu$mol, 0.3 $\mu$mol, and 1 $\mu$mol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

EXAMPLES

Example 1

2'-0-(nonyl) adenosine (1)

To a solution of 10 g of adenosine in 400 ml of dimethyl formamide is added 2.25 g of 60% sodium hydride (oil). After one hour, 8.5 ml of 1-bromo-nonane is added. The reaction is stirred for 16 hours. Ice is added and the solution evaporated in vacuo. Water and ethyl acetate are added. The organic phase is separated, dried, and evaporated in vacuo to give a white solid, which is recrystallized from ethanol to yield 4.8 g of the title compound, M.P. 143–144° C. analysis for: $C_{19}H_{31}N_5O_4$. Calculated: C, 57.99; H, 7.94; N, 1779. Found: C, 58.13; H, 7.93; N, 17.83.

Example 2

2'-0-(nonyl)-$N^6$-enzoyladenosine (2)

2'-0-(nonyl)adenosine (1) is treated with benzoyl chloride in a manner similar to the procedure of B. L. Gaffney and R. A. Jones, *Tetrahedron Lett.,* Vol. 23, p. 2257 (1982). After chromatography on silica gel (ethyl acetate-methanol), the title compound was obtained. Analysis for: $C_{26}H_{35}N_5O_5$. Calculated: C, 62.75; H, 7.09; N, 17.07. Found: C, 62.73; H, 14.07; N, 13.87.

Example 3

2'-0-(nonyl)-5'-0-dimethoxytrityl-$N^6$-benzoyladenosine (3)

To a solution of 4.0 g of 2'-0-(nonyl) $N^6$-benzoyladenosine (2) in 250 ml of pyridine is added 3.3 g of 4,4'-dimethoxy-trityl chloride. The reaction is stirred for 16 hours. The reaction is added to ice/water/ethyl acetate, the organic layer is separated, dried, and concentrated in vacuo to a gum. 5.8 g of the title compound was obtained after chromatography on silica gel (ethyl acetate-methanol triethylamine). Analysis for: $C_{47}H_{53}N_5O_7$. Calculated: C, 70.56; H, 6.68; N, 8.75. Found: C, 70.26; H, 6.70; N, 8.71.

Example 4

$N^6$-benzoyl-5'-0-dimethoxytrityl-2'-0-(nonyl) adenosine-3'-0,N,N-diisopropyl-$\beta$-cyanoethyl phosphoramidite (4)

2'-0-(nonyl)-5'-0-dimethoxytrityl-N-benzoyladenosine (3) is treated with ($\beta$-cyanoethoxy)chloro(N,N-diisopropyl) aminephosphane in a manner similar to the procedure of F. Seela and A. Kehne, *Biochemistry,* Vol. 26, p. 2233 (1987). After chromatography on silica gel (E=OAC/hexane), the title compound was obtained as a white foam.

Example 5

2'-0-(pentyl) adenosine (5)

The title compound is prepared as per example 1, using 1-bromopentane instead of 1-bromononane, M.P.

-108–109° C. Analysis for: $C_{15}H_{24}N_5O_4$. Calculated: C, 53.24; H, 7.15; N, 20.69. Found: C, 53.37; H, 6.86; N, 20.51.

Example 6

2'-0-(pentyl)-$N^6$-benzoyladenosine (6)

Benozylation of 2'-0-(pentyl) adenosine, as per example 2, gives the title compound. Analysis for: $C_{22}H_{29}N_5O_5$. Calculated: C, 59.58; H, 6.59; N, 15.79. Found: C, 59.34; H, 6.27; N, 15.53.

Example 7

2'-0-(pentyl)-5'-0-dimethoxytrityl-$N^6$-benzoyladenosine (7)

The title compound is prepared from 2'-0-(pentyl)-$N^6$-benzoyladenosine (6) as per example 3. Analysis for: $C_{43}H_{46}N_5O_7$. Calculated: C, 69.34; H, 6.22; N, 9.40. Found: C, 68.97; H, 6.07; N, 9.12.

Example 8

$N^6$-benzoyl-5'-0-dimethoxytrityl-2'-0-(pentyl) adenosine-3-0,N,N-diisopropyl-β-cyanoethyl phosphoramidite (8)

The title compound is prepared from 2'-0-(pentyl)-5'-0-dimethoxytrityl-$N^6$-benzoyladenosine (7) as per example 4.

Example 9

2'-0-(benzyl) adenosine (9)

The title compound is prepared as per example 1, using benzylbromide instead of 1-bromononane. After chromatography on silica gel (E=OAC-meoh) gives a white solid. M.P. -87–88° C. Analysis for: $C_{17}H_{19}N_5O_4$.25m $H_2O$. Calculated: C, 56.42; H, 5.43; N, 19.35. Found: C, 56.46; H, 5.23; N, 19.50.

Example 10

2'-0-(benzyl)-$N^6$-benzoyladenosine (10)

Benzoylation of 2'-0-(benzyl)adenosine (9), as per example 2, gives the title compound. Analysis for: $C_{24}H_{23}N_5O_5$. 25m H2O. Calculated: C, 61.86; H, 5.08; N, 15.03. Found C, 61.89; H, 5.01; N, 14.88.

Example 11

2'-0-(benzyl)-5'-0-dimethoxyltrityl-$N^6$-benzoyladenosine (11)

The title compound is prepared from 2'-0-(benzyl)-N-benzoyladenosine (10) as per example 3. Analysis for: $C_{45}H_{41}N_5O_7$. Calculated: C, 70.76; H, 5.41; N, 9.17. Found: C, 70.84; H, 5.35; N, 8.90.

Example 12

$N^6$-benzoyl-5'-0-dimethoxytrityl-2'-0-(benzyl) adenosine-3'-0,N,N-diisopropyl-β-cyanoethyl phosphoramidite (12)

The title compound is prepared from 2'-0-(benzyl)5'-0-dimethoxytrityl-$N^6$-benzoyladenosine (11) as per example 4. The compound is a white foam.
$^{31}$P-NMR(CDCN) S 151.08, 151.25

Example 13

2'-0-(butyl) adenosine (13)

The title compound is prepared as per example 1 using 1-bromobutane instead of 1-bromononane. After chroma tography on silica gel (E=OAC-MEoH), a white solid was obtained.
1 H-NMR (DMSO-$d_6$): 5.97 (d, 1H, C, H).

Example 14

2'-0-(butyl)-$N^6$-benzoyladenosine (14)

Benzoylation of 2'-0-(butyl)adenosine (13), as per example 2, gives the title compound as a white foam.
1 H-NMR(DMSO-$d_6$): 6.11 (d,1H,C,H).

Example 15

2'-0-(butyl)-5'-0-dimethoxytrityl-$N^6$-benzoyl-adenosine (15)

The title compound is prepared from 2'-0-(butyl)-$N^6$-benzoyladenosine (14) as per example 3. After chromatography of silica gel (E=OAC-Hexane-TRA) a yellow foam was obtained. Analysis for: $C_{42}H_{43}N_5O_7$. Calculated: C, 69.12; H, 5.94; N, 9.59. Found: C, 69.21; H, 5.99; N, 9.43.

Example 16

$N^6$-benzoyl-5'-0-dimethoxytrityl-2'-0-(butyl) adenosine-3'-0,N,N-diisopropyl-β-cyanoethyl phosphoramidite (16)

The title compound is prepared from 2'-0-(butyl)-5'-0-dimethoxytrityl-$N^6$-benzoyladenosine (15) as per example 4. The compound is a white foam.

Example 17

2'-0-(propyl)adenosine (17)

The title compound is prepared as per example 1 using 1-bromopropane instead of 1-bromononane, M.P. 127–128° C. Analysis for: $C_{13}H_{19}N_5O_4$. Calculated: C, 50.48; H, 6.19; N, 22.64. Found: C, 50.58; H, 6.21; N, 22.56.

Example 18

2'-0-(propyl)-$N^6$-benzoyladenosine (18)

Benzoylation of 2'-0-(propyl)adenosine (17), as per example 2, gave the title compound. Analysis for: $C_{20}H_{23}N_5O_5$. Calculated: C, 58.10; H, 5.61; N, 16.94. Found C, 58.12; H, 5.58; N, 16.79.

Example 19

2'-0-(propyl)-5'-0-dimethoxytrityl-$N^6$-benzoyladenosine (19)

The title compound is prepared from 2'-0-(propyl)-$N^6$benzoyladenosine (18) as per example 3.
1 H-NMR (DMSO-$d_6$): 6.13(d, 1H, C, H)

Example 20

$N^6$-benzoyl-5'-0-dimethoxytrityl-2'-0-(propyl) adenosine-3'-O,N,N-diisopropyl-β-cyanoethyl phosphoramidite (20)

The title compound is prepared from 2'-0-(propyl)-5'-0-dimethoxytrityl-$N^6$-benzoyladenosine (19) as per example 4. The compound is a white foam.

Example 21

2'-0-(allyl)adenosine (21)

The title compound is prepared as per example 1 using allylbromide instead of 1-bromononane. The compound is a white solid, after chromatography on silica gel (E=OAC-methanol).

$^1$HNMR (DMSO-$d_6$): S 6.03 (d, 1H, C, H).

Example 22

2'-0-(allyl)-N$^6$-benzoyladenosine (22)

Benzoylation of 2'-0-(allyl)adenosine (21), as per example 2, gave the title compound as a white foam.

$^1$H NMR (DMSO-$d_6$): S 6.17 (d, 1H, C, H)

Example 23

2'-0-(allyl)-5'-0-dimethoxytrityl-N$^6$-benzoyl-adenosine (23)

The title compound is prepared from 2'-0-(allyl)-N$^6$-benzoyladenosine (22) as per example 3. Analysis for: $C_{41}H_{39}N_5O_7$. Calculated: C, 68.99; H, 5.51: N, 9.81. Found: C, 68.68; H, 5.43; N, 9.70.

Example 24

N$^6$-benzoyl-5'-0-dimethoxytrityl-2'-0-(allyl) adenosine-3'-0,N,N-diisopropyl-β-cyanoethyl phosphoramidite (24)

The title compound is prepared from 2'-0-(allyl)-5'-0-dimethoxytrityl-N$^6$-benzoyladenosine (23) as per example 4. The compound is a white foam.

$^{32}$P NMR (CD$_3$CN) S 151.11,151.32.

Example 25

2'-0-(propylphthalimide)adenosine (25)

The title compound is prepared as per example 1, using N-(3-bromopropyl)phthalimide. Chromatography on silica gel gives a white solid, M.P. 123–124° C. Analysis for: $C_{21}H_{22}N_6O_6$. Calculated: C, 55.03; H, 4.88; N, 18.49. Found: C, 55.38; H, 4.85; N, 18.46.

Example 26

2'-0-(propylphthalmide)-N$^6$-benzoyladenosine (26)

Benzoylation of 2'-0-(propylphthalimide)adenosine (25), as per example 2, gives the title compound. Analysis for: $C_{28}H_{26}N_6O_7$. Calculated: C, 60.21; H, 4.69; N, 15.05. Found: C, 59.94; H, 4.66; N, 14.76.

Example 27

2'-0-(propylphthalimide)-5'-0-dimethoxytrityl-N-benzoyladenosine (27)

The title compound is prepared from 2'-0-(propylphthalimide)-N$^6$-benzoyladenosine (26) as per example 3. Analysis for: $C_{49}H_{44}N_6O_9$. Calculated: C, 68.36; H, 5.15; N, 9.76. Found: C, 68.16; H, 5.03; N, 9.43.

Example 28

N$_6$-benzoyl-5'-0-dimethoxytrityl-2'-(propyl) adenosine-3'-0,N,N-diisopropyl-β-cyanoethylphosphoramidite (28)

The title compound is prepared from 2'-0-(propylphthalimide)-5'-0-dimethoxytrityl-N$^6$-benzoyladenosine (27) as per example 4. A white foam was obtained.

Example 29

2'-0-(butylphthalimide)adenosine (29)

The title compound is prepared as per example 1, using n-(4-bromobutyl)phthalimide instead of 1-bromononane. Chromatography on silica gel (E=OAC-MeOH) gives a white solid. M.P. 199–200° C. Analysis for: $C_{22}H_{24}N_6O_6$. Calculated: C, 56.42; H, 5.16; N, 17.94. Found: C, 56.31; H, 5.04; N, 17.95.

Example 30

2'-0-(butylphthalimide-N$^6$-benzoyladenosine) (30)

Benzoylation of 2'-0-(butylphthalimide)adenosine (29) as per example 2, gives the title compound. Analysis for: $C_{29}H_2N_6O_7$. Calculated: C, 60.83; H, 4.93; N, 14.68. Found: C, 60.48; N, 14.41.

Example 31

2'-0-(butylphthalimide)-5'-0-dimethoxytrityl-N-benzoyladenosine (31)

The title compound is prepared from 2'-0-(butylphthalimide)-N$^6$-benzoyladenosine (30) as per example 3. Analysis for: $C_{50}H_{46}N_6O_9$. Calculated: C, 68.64; H, 5.29; N, 9.60. Found: C, 68.47; H, 5.12; N, 9.37.

Example 32

N$^6$-benzoyl-5'-0-dimethoxytrityl-2'-0-(butylphthalimide)adenosine-3'-O,N,N-diisopropyl-β-cyanoethylphosphoramidine (32)

The title compound was prepared from compound (31) as per example 4.

$^{31}$P NMR (CD$_3$CN) S 150.88, 151.22.

Example 33

2'-0-(pentyphthalimide)adenosine (33)

The title compound is prepared as per example 1, usinig N-(5-bromopentyl)phthalimide instead of 1-bromo-nonane. M.P. 159–160° C. Analysis for: C, 57.26; H, 5.43; N, 17.42. Found: C, 57.03; H, 5.46; N, 17.33.

Example 34

2'-0-(pentyphthalimide)-N$^6$-benzoyladenosine (34)

Benzoylation of 2'-0-(penthylphthalimide)adenosine (33) as per example 2 gives the title compound. $^1$H NMR (DMSO-$d_6$): 6.10 (d, 1H, $C_1$, H). Analysis for: $C_{30}H_{30}N_6O_7$. Calculated: C, 61.43; H, 5.16; N, 14.33. Found: C, 61.51; H, 4.97; N, 14.10.

Example 35

2'-0-(pentylphthalimide)-5' -dimethoxytrityl-N$^6$-benzoyladenosine (35)

The title compound is prepared from 2'-0-(pentylphthalimide)-N$^6$-benzoyladenosine (34) as per example 3. After chromatography on silica gel (ethylacetate, hexane, triethylamine), the title compound was obtained. Analysis for: $C_{51}H_{48}N_6O_9$. Calculated: C, 68.91; H, 5.44; N, 9.45. Found: C, 68.65; H, 5.45; N, 9.61.

Example 36

N$^6$-benzoyl-5'-0-dimethoxytrityl-2'-0-(pentylphthalimide) adenosine-3'-0,N,N-diisopropyl-β-cyanoethylphosphor-amidite (36)

The title compound is prepared from 2'-0-(pentylphthalimide)-5'-0-dimethoxytrityl-N$^6$-benzoyladenosine (35) as per example 4. The compound is a white foam.

Example 37

2'-0-(ethyl)adenosine (37)

The title compound is prepared as per example 1 using ethyl bromide instead of 1-bromononane. The compound is a white solid. '1H NMR (DMSO-$d_6$): S 6.00 (d,$_1$H, $C_1$, H)

Example 38

2'-0-(ethyl)-N-benzoyladenosine (38)

Benzoylation of 2-0-(ethyl)adenosine (37), as per example 2, gives the title compound. The compound is a white foam.

Example 39

2'-0-(ethyl)-5'-0-dimethoxytrityl-$N^6$-benzoyladenosine (39)

The title compound is prepared from 2'-0-(ethyl)-$N^6$-benzoyladenosine (38) as per example 3. The compound is a white foam.

Example 40

$N^6$-benzoyl-5'-0-dimethoxytrityl-2'-0-(ethyl) adenosine-3'-O,N,N-diisopropyl-β-cyancethylphosphoramidite (40)

The title compound is prepared from 2'-0-(ethyl)-5'-0-dimethoxytrityl-$N^6$-benzoyladenosine (39) as per example 4. The compound is a white foam.

Example 41

2'-O-[imidizo-1-yl-(propyl)]adenosine (41)

The title compound can be prepared as per example 1 using 1-(3-bromopropyl)imidazole in place of 1-bromononane.

Example 42

2'-O-[imidizo-1-yl-(propyl)]-$N^6$-benzoyladenosine (42)

Benoylation of 2'-O-[imidizo-1-yl-(propyl)]adenosine (41) as per example 2 will give the title compound.

Example 43

2'-O-[imidizo-1-yl-(propyl)]-5'-O-dimethoxytrityl-$N^6$-benzoyladenosine (43)

The title compound can be prepared from 2'-O-[imidizo-1-yl-(propyl)]adenosine (42) as per example 3.

Example 44

$N^6$-benzoyl-5'-O-dimethoxytrityl-2'-O-[imidizo-1-yl-(propyl)]-adenosine-3'-O,N,N-diisopropyl-β-cyanoethyl phosphoramidite (44)

The title compound can be prepared from 2'-O-[imidizo-1-yl-(propyl)]-5'-O-dimethoxytrityl-$N^6$-benzoyladenosine (43) as per example 4.

Example 45

2'-O-(phenylpropyl) adenosine (45)

The title compound can be prepared as per example 1 using 3-bromopropylbenzene in place of 1-bromononane.

Example 46

2'-O-(phenylpropyl)-$N^6$-benzoyladenosine (46)

Benoylation of 2'-O-(phenylpropyl)adenosine (45) as per example 2 will give the title compound.

Example 47

2'-O-(phenylpropyl)-5'-O-dimethoxytrityl-$N^6$-benzoyl-adenosine (47)

The title compound can be prepared from 2'-O-(phenylpropyl) adenosine (46) as per example 3.

Example 48

$N^6$-benzoyl-5'-O-dimethoxytrityl-2'-O-(phenylpropyl)adenosine-3'-O,N,N-diisopropyl-β-cyanoethylphosphor-amidite (48)

The title compound can be prepared from 2'-O-(phenylpropyl)-5'-O-dimethoxytrityl-$N^6$-benzoyladenosine (47) as per example 4.

Example 49

2'-O-[naphth-1-yl-(propyl)]adenosine (49)

The title compound can be prepared as per example 1 using 1-(3-bromopropyl)naphthalene in place of 1-bromononane.

Example 50

2'-O-[naphth-1-yl-(propyl)]-$N^6$-benzoyl-adenosine (50)

Benoylation of 2'-O-[naphth-1-yl-(propyl)]adenosine (49) as per example 2 will give the title compound.

Example 51

2'-O-[naphth-1-yl-(propyl)]-5'-O-dimethoxytrityl-$N^6$-benzoyl-adenosine (51)

The title compound can be prepared from 2'-O-[naphth-1-yl-(propyl)]-$N^6$-benzoyladenosine (50) as per example 3.

Example 52

$N^6$-benzoyl-5'-O-dimethoxytrityl-2'-O-[naphth-1-yl-(propyl)]adenosine-3'-O,N,N-diisopropyl-β-cyanoethyl phosphoramidite (52)

The title compound can be prepared from 2'-O-[naphth-1-yl-(propyl)]-5'-O-dimethoxytrityl-$N^6$-benzoyladenosine (51) as per example 4.

Example 53

2'-O-[anthracen-2-yl-(propyl)]adenosine (53)

The title compound can be prepared as per example 1 using 2-(3-bromopropyl)anthracene in place of 1-bromononane.

Example 54

2'-O-[anthracen-2-yl-(propyl)]-$N^6$-benzoyl-adenosine (54)

Benoylation of 2'-O-[anthracen-2-yl-(propyl)]adenosine (53) as per example 2 will give the title compound.

Example 55

2'-O-[anthracen-2-yl-(propyl)]-5'-O-dimethoxytrityl-N$^6$-benzoyl-adenosine (55)

The title compound can be prepared from 2'-O-[anthracen-2-yl-(propyl)]-N$^6$-benzoyladenosine (54) as per example 3.

Example 56

N$^6$-benzoyl-5'-O-dimethoxytrityl-2'-O-[anthracen-2-yl-(propyl)]adenosine-3'-O,N,N-diisopropyl-β-cyanoethyl phosphoramidite (56)

The title compound can be prepared from 2'-O-[anthracen-2-yl-(propyl)]-5'-O-dimethoxytrityl-N$^6$-benzoyl-adenosine (55) as per example 4.

Example 57

2'-O-[bis(phthalimidobutyl)-(aminobutyl)]-N$^6$-benzoyl-adenosine (57)

Compound 30 is treated with TIPS reagent (tetraisopropyl-disilyldichloride) to block the 3',5'-hydroxyl groups with the TIPS blocking group. Treatment with ammonium hydroxide cleaves the phthalimide group yielding a 2'-O-amino butyl blocked adenosine. This compound can be further treated as per example 29 with n-(4-bromobutyl)phthalimide to yield the 2'-O-polyalkylamino blocked adenosine. Deblocking of the TIPS blocking group with tetrabutyl ammonium fluoride will yield the title compound. The title compound can be used as per examples 31 and 32 to form suitable blocked nucleotides suitable for incorporation into oligonucleotides.

Example 58

2'-O-[bis(aminobutyl)-(aminobutyl)]-N$^6$-benzoyladenosine (58)

Treatment of compound 57 with ammonium hydroxide cleaves the phthalimide group to yield the title compound. This compound can be further treated in the manner of example 57 to further elongate the polyalkylamino chain.

Example 59

N$^6$-Benzoyl-[2'-deoxy-2'-fluoro-5'-O-(4,4'-dimethoxy trityl)]adenosine-3'-O,N,N-diisopropyl-β-cyanoethyl phosphoramidite (59)

N$^6$-Benzoyl-9-(2'-fluoro-β-D-ribofuranosyl)adenine was prepared from 9-β-D-arabinofuranosyladenine in a five-step synthesis using a modification of a procedure reported by M. Ikehara at al., *Nucleosides and Nucleotides* Vol. 2, pp. 373–385 (1983). Thus, the N$^6$-benzoyl derivative was obtained in good yield utilizing the method of transient protection with chlorotrimethylsilane. R. A. Jones, *J. Am. Chem. Soc.* Vol. 104, pg. 1316 (1982). Selective protection of the 3' and 5'-hydroxyl groups of N$^6$-Benzoyl-9-β-D-arabinofuranosyladenine with tetrahydropyranyl (THP) was accomplished by modification of a literature procedure G. Butke, et al., in *Nucleic Acid Chemistry*, Part 3, pp. 149–152, Townsend, L. B. and Tipson, R. S. eds., (J. Wiley and Sons, New York 1986) to yield N$^6$-Benzoyl-9-[3',5'-di-O-tetrahydropyran-2-yl)-β-D-arabino furanosyl]adenine in good yield. Treatment of N$^6$-Benzoyl-9-[3',5'-di-O-tetrahydropyran-2-yl)-β-D- arabinofuranosyl]adenine with trifluoromethanesulfonic anhydride in dichloromethane gave the 2'-triflate derivative N$^6$-Benzoyl-9-[2'-O-trifluoromethylsulfonyl-3',5'-di-O-tetrahydropyran-2-yl)-β-D-arabinofuranosyl]adenine which was not isolated due to its lability. Displacement of the 2'-triflate group was effected by reaction with tetrabutyl ammonium fluoride in tetrahydrofuran to obtain a moderate yield of the 2'-fluoro derivative N$^6$-Benzoyl-9-[2'-fluoro-3',5'-di-O-tetra-hydropyran-2-yl)-β-D-arabinofuranosyl]adenine. Deprotection of the THP groups of N$^6$-Benzoyl-9-[2'-fluoro-3',5'-di-O-tetrahydropyran-2-yl)-β-D-arabinofuranosyl]adenine was accomplished by treatment with Dowex-50W in methanol to yield N$^6$-benzoyl-9-(2'-deoxy-2'-fluoro-β-D-ribofuranosyl) adenine in moderate yield. The $^1$H-NMR spectrum was in agreement with the literature values. M. Ikehara and H. Miki, *Chem. Pharm. Bull.,* Vol. 26, pp. 2449–2453 (1978). Standard methodologies such as those of foregoing examples 3 and 4 were employed to obtain the 5'-dimethoxytrityl-3'-phos-phoramidite intermediates N$^6$-Benzoyl-9-[2'-fluoro-5'-O-(4,4'-di-methoxytrityl)-β-D-ribofuranosyl]adenine and N$^6$-Benzoyl-[2'-deoxy-2'-fluoro-5'-O-(4,4'-dimethoxytrityl)]adenosine-3'-O-(N,N-diisopropyl-β-cyanoethyl phosphoramidite). K. K. Ogilvie, *Can J. Chem.* Vol. 67, pp. 831–839 (1989).

Example 60

N$^6$-Benzoyl-9-β-D-arabinofuranosyladenine (60)

9-β-D-arabinofuranosyladenine (1.07 g, 4.00 m.mol) was dissolved in anhydrous pyridine (20 mL) and anhydrous dimethyl formamide (20 ml) under an argon atmosphere. The solution was cooled to ice temperature and chlorotrimethyl-silane (3.88 ml, 30.6 m.mol) was added slowly to the reaction mixture via syringe. After stirring the reaction mixture at ice temperature for 30 minutes, benzoyl chloride (2.32 ml, 20 m.mol) was added slowly. The reaction mixture was allowed to warm to 20° C. and stirred for 2 hours. After cooling the reaction mixture to ice temperature, cold water (8 ml) was added and the mixture was stirred for 15 minutes. Concentrated ammonium hydroxide (8 ml) was slowly added to the reaction mixture to give a final concentration of 2M of ammonia. After stirring the cold reaction mixture for 30 minutes, the solvent was evaporated in vacuo (60 torr) at 20° C. followed by evaporation in vacuo (1 torr) at 40° C. to give an oil: This oil was triturated with diethyl ether (50 ml) to give a solid which was filtered and washed with diethyl ether three times. This crude solid was triturated in methanol (100 ml) at reflux temperature three times and the solvent was evaporated to yield N$^6$-Benzoyl-9-β-D-arabino-furanosyl adenine (60) as a solid (1.50 g, 100%).

Example 61

N$^6$-Benzoyl-9-[3',5'-di-O-tetrahydropyran-2-yl)-β-D-arabino-furanosyl]adenine (61)

N$^6$-Benzoyl-9-β-D-arabinofuranosyladenine (60) (2.62 g, 7.06 m.mol) was dissolved in anhydrous dimethylformamide (150 ml) under an argon atmosphere and p-toluenesulfonic acid monohydrate (1.32 g, 6.92 m.mol) was added. This solution was cooled to ice temperature and dihydropyran (1.26 ml, 13.8 m.mol) was added via syringe. The reaction mixture was allowed to warm to 20° C. Over a period of 5 hours a total of 10 equivalents of dihydropyran were added in 2 equivalent amounts in the fashion described. The reaction mixture was cooled to ice temperature and saturated aqueous sodium bicarbonate was added slowly to a pH of 8, then water was added to a volume of 750 ml. The aqueous mixture was extracted with methylene chloride four times (4×200 ml), and the organic phases were combined and dried over magnesium sulfate. The solids were filtered and the solvent was evaporated in vacuo (60 torr) at 30° C.

to give a small volume of liquid which was evaporated in vacuo (1 torr) at 40° C. to give an oil. This oil was coevaporated with p-xylene in vacuo at 40° to give an oil which was dissolved in methylene chloride (100 ml). Hexane (200 ml) was added to the solution and the lower-boiling solvent was evaporated in vacuo at 30° C. to leave a white solid suspended in hexane. This solid was filtered and washed with hexane three times (3×10 ml) then purified by column chromatography using silica and methylene chloride-methanol (93:7, v/v) as eluent. The first fraction yielded the title compound (61) as a white foam (3.19 g, 83%) and a second fraction gave a white foam (0.81 g) which was characterized as the 5'-mono-tetrahydropyranyl derivative of $N^6$-Benzoyl-9-β-D-arabino-furanosyl adenine.

Example 62

$N^6$-Benzoyl-9-[2'-O-trifluoromethylsulfonyl-3',5'-di-O-tetrahydro-pyran-2-yl)-β-D-arabinofuranosyl] adenine (62)

$N^6$-Benzoyl-9-[3',5'-di-O-tetrahydropyran-2-yl)-β-D-arabinofuranosyl]adenine (61) (2.65 g, 4.91 m.mol) was dissolved in anhydrous pyridine (20 ml) and the solvent was evaporated in vacuo (1 mm Hg) at 40° C. The resulting oil was dissolved in anhydrous methylene chloride (130 ml) under an argon atmosphere and anhydrous pyridine (3.34 ml, 41.3 m.mol) and N,N-dimethylamino-pyridine (1.95 g, 16.0 mmol) were added. The reaction mixture was cooled to ice temperature and trifluoromethanesulfonic anhydride (1.36 ml, 8.05 mmol) was added slowly via syringe. After stirring the reaction mixture at ice temperature for 1 h, it was poured into cold saturated aqueous sodium bicarbonate (140 ml). The mixture was shaken and the organic phase was separated and kept at ice temperature. The aqueous phase was extracted with methylene chloride two more times (2×140 ml). The organic extracts which were diligently kept cold were combined and dried over magnesium sulfate. The solvent was evaporated in vacuo (60 torr) at 20° C. then evaporated in vacuo (1 torr) at 20° C. to give $N^6$-Benzoyl-9-[2'-O-trifluoromethylsulfonyl-3',5'-di-O-tetrahydro-pyran-2-yl)-β-D-arabinofuranosyl]adenine (62) as a crude oil which was not purified further.

Example 63

$N^6$-Benzoyl-9-[2'-fluoro-3',5'-di-O-tetrahydropyran-2-yl)-β-D-arabinofuranosyl]adenine (63)

$N^6$-Benzoyl-9-[2'-O-trifluoromethylsulfonyl-3',5'-di-O-tetrahydropyran-2-yl)-β-D-arabinofuranosyl]adenine (62), (4.9 mmol) as a crude oil was dissolved in anhydrous tetrahydrofuran (120 ml) and this solution was cooled to ice temperature under an argon atmosphere. Tetrabutylammonium fluoride as the hydrate (12.8 g, 49.1 mmol) was dissolved in anhydrous tetrahydrofuran (50 ml) and half of this volume was slowly added via syringe to the cold reaction mixture. After stirring at ice temperature for 1 hour, the remainder of the reagent was added slowly. The reaction mixture was stirred at ice temperature for an additional 1 hour, then the solvent was evaporated in vacuo (60 torr) at 20° C. to give an oil. This oil was dissolved in methylene chloride (250 ml) and washed with brine three times. The organic phase was separated and dried over magnesium sulfate. The solids were filtered and the solvent was evaporated to give an oil. The crude product was purified by column chromatography using silica in a sintered-glass funnel (600 ml) and ethyl acetate was used as eluent. $N^6$-Benzoyl-9-[2'-fluoro-3',5'-di-O-tetrahydropyran-2-yl)-β-D-arabino-furanosyl]adenine (63) was obtained as an oil (2.03 g, 76%).

Example 64

$N^6$-Benzoyl-9-(2'-fluoro-β-D-ribofuranosyl) adenine (64)

$N^6$-Benzoyl-9-[2'-fluoro-3',5'-di-O-tetrahydropyran-2-yl)-β-D-arabinofuranosyl]adenine (63) (1.31 g, 2.42 mmol) was dis-solved in methanol (60 ml), and Dowex 50W× 2–100 (4 cm³, 2.4 m.eq) was added to the reaction mixture. The reaction mixture was stir-red at 20° C. for 1 hour then cooled to ice temperature. Triethyl-amine (5 ml) was then slowly added to the cold reaction mixture to a pH of 12. The resin was filtered and washed with 30% triethyl-amine in methanol until the wash no longer contained UV absorbing material. Toluene (50 ml) was added to the washes and the solvent was evaporated at 24° C. in vacuo (60 torr then 1 torr) to give a residue. This residue was partially dissolved in methylene chloride (30 ml) and the solvent was transferred to a separatory funnel. The remainder of the residue was dissolved in hot (60° C.) water and after cooling the solvent it was also added to the separatory funnel. The biphasic system was extracted, and the organic phase was separated and extracted three times with water (3×100 ml). The combined aqueous extracts were evaporated in vacuo (60 torr then 1 torr Hg) at 40° C. to give an oil which was evaporated with anhydrous pyridine (50 ml). This oil was further dried in vacuo (1 torr Hg) at 20° C. in the presence of phosphorous pentoxide overnight to give $N^6$-Benzoyl9-(2'-fluoro-β-D-ribo-furanosyl) adenine (64) as a yellow foam (1.08 g, 100%) which contained minor impurities.

Example 65

$N^6$-Benzoyl-9-[2'-fluoro-5'-O-(4,4'-dimethoxy-trityl)-β-D-ribofuranosyl]adenine (65)

$N^6$-Benzoyl-9-(2'-fluoro-β-D-ribofuranosyl)adenine (64) (1.08 g, 2.89 mmol) which contained minor impurities was dissolved in anhydrous pyridine (20 ml) under an argon atmosphere, and dry triethylamine (0.52 ml, 3.76 mmol) was added followed by addition of 4,4'-dimethoxytrityl chloride (1.13 g, 3.32 mmol). After 4 hours of stirring at 20° C. the reaction mixture was transferred to a separatory funnel and diethyl ether (40 ml) was added to give a white suspension. This mixture was washed with water three times (3×10 ml), the organic phase was separated and dried over magnesium sulfate. Triethylamine (1 ml) was added to the solution and the solvent was evaporated in vacuo (60 torr Hg) at 20° C. to give an oil which was evaporated with toluene (20 ml) containing triethylamine (1 ml). This crude product was purified by column chromatography using silica and ethyl acetatetriethylamine (99:1, v/v) followed by ethyl acetatemethanol-triethylamine (80:19:1) to give the product in two fractions. The fractions were evaporated in vacuo (60 torr then 1 torr Hg) at 20° C. to give a foam which was further dried in vacuo (1 torr Hg) at 20° C. in the presence of sodium hydroxide to give $N^6$-Benzoyl-9-[2'-fluoro-5'-O-(4,4'-dimeth-oxytrityl)-β-D-ribofuranosyl]adenine (65) as a foam (1.02 g, 52%).

Example 66

$N^6$-Benzoyl-[2'-deoxy-2'-fluoro-5'-O-(4,4'-dimethoxytrityl)]adenosine-3'-O,N,N-diisopropyl-β-cyanoethyl phosphoramidite (66)

$N^6$-Benzoyl-9-[2'-fluoro-5'-O-(4,4'-dimethoxytrityl)-β-D-ribofuranosyl]adenine (65) (1.26 g, 1.89 mmol) was dissolved in anhydrous dichloromethane (13 ml) under an argon atmosphere, diisopropylethylamine (0.82 ml, 4.66 mmol) was added, and the reaction mixture was cooled to ice temperature. Chloro(diisopropylamino)-β-cyanoethoxyphosphine (0.88 ml, 4.03 mmol) was added to the reaction mixture which was allowed to warm to 20° C. and stirred for 3 hours. Ethylacetate (80 ml) and triethylamine (1 ml) were added and this solution was washed with brine solution three times (3×25 ml). The organic phase was separated and dried over magnesium sulfate. After filtration of the solids the solvent was evaporated in vacuo at 20° C.

to give an oil which was purified by column chromatography using silica and hexane-ethyl acetate-triethylamine (50:49:1) as eluent. Evaporation of the fractions in vacuo at 20° C. gave a foam which was evaporated with anhydrous pyridine (20 ml) in vacuo (1 torr) at 26° C. and further dried in vacuo (1 torr Hg) at 20° C. in the presence of sodium hydroxide for 24 h to give $N^6$-Benzoyl-[2'-deoxy-2'-fluoro-5'-O-(4,4'-dimethoxytrityl)]adenosine-3'-O,N,N-diisopropyl-β-cyanoethyl phosphoramidite (66) as a foam (1.05 g, 63%).

Example 67

2'-Deoxy-2'-fluoro-5'-O-(4,4'-dimethoxytrityl)-uridine3'-O-(N,N-diisopropyl-β-cyanoethylphosphoramidite). (67)

The title compound is prepared via a modification of a literature procedure, J. Fox, et al., *J. Org. Chem.,* Vol. 29, pp. 558–564 (1964). Thus, 2,2'-cyclouridine (5.65 g, 25 mmol) is treated with a solution of 70% hydrogen fluoride/pyridine (65 mL) in anhydrous dioxane (500 mL) at 120° C. in a sealed steel vessel for twenty hours. The reaction mixture is cooled to ice temperature, poured into ice (400 mL), and the pH is adjusted to 7 by addition of solid $CaCO_3$. After the solvent is evaporated in vacuo (1 torr), the residue is dissolved in methanol, adsorbed onto silica gel, and purified by column chromatography using silica and ethyl acetate-methanol (v/v, 20:1) as eluent to give 2'-deoxy-2'-fluoro-uridine as a white solid (4.81 g, 79%). The 5'-DMT and 3'-cyanoethoxy-diisopropyl phosphoramidite derivatized nucleoside are obtained in accordance with the procedures of examples 65 and 66.

Example 68

2'-Deoxy-2'-fluoro-5'-O-(4,4'-dimethoxytrityl)-cytidine-3'-O-(N,N-diisopropyl-β-cyanoethylphosphoramidite). (68)

2'-deoxy-2'-fluorouridine (2.51 g, 10.3 mmol) is converted to corresponding cytidine analog via a literature procedure, C. B. Reese, et al., *J. Chem. Soc. Perkin Trans I,* pp. 1171–1176 (1982), by acetylation with acetic anhydride (3.1 mL, 32.7 mmol) in anhydrous pyridine (26 mL) at room temperature. The reaction is quenched with methanol, the solvent is evaporated in vacuo (1 torr) to give an oil which is coevaporated with ethanol and toluene. 3',5'-O-diacetyl-2'-deoxy-2'-fluorouridine is crystallized from ethanol to afford colorless crystals (2.38 g, 81%). N-4-(1,2,4-triazol-1-yl)-3',5'-O-diacetyl-2'-deoxy-2'-fluoro-uridine is obtained in a 70% yield (2.37 g) by reaction of 3',5'-O-diacetyl-2'-deoxy-2'-fluorouridine (2.75 g, 9.61 mmol) with 1,2,4-triazole (5.97 g, 86.5 mmol), phosphorus oxychloride (1.73 mL, 18.4 mmol), and triethylamine (11.5 mL, 82.7 mmol) in anhydrous acetonitrile at room temperature. After 90 min the reaction mixture is cooled to ice temperature and triethylamine (7.98 ml, 56.9 mmol) is added followed by addition of water (4.0 ml). The solvent is evaporated in vacuo (1 torr) to give an oil which is dissolved in methylene chloride and washed with saturated aqueous sodium bicar-bonate. The aqueous phase is extracted with methylene chloride twice (2×100 mL) and the organic extracts are dried with magnesium sulfate. Evaporation of the solvent afforded an oil from which the product N-4-(1,2,4-triazol-1-yl)-3',5'-O-diacetyl-2'-deoxy-2'-fluorouridine is obtained by crystallization from ethanol. 2'-deoxy-2'-fluorocytidine is afforded by treatment of protected triazol-1-yl derivative with concentrated ammonium hydroxide (4.26 mL, 81.2 mmol) in dioxane at room temperature for 6 hours. After evaporation of the solvent the oil is stirred in half-saturated (at ice temperature) ammonia in methanol for 16 hours. The solvent is evaporated and 2'-deoxy-2'-fluorocytidine is crystallized from ethylacetate-methanol (v/v, 75:25) to give colorless crystals (1.24 g, 75%). N-4-benzoyl-2'-deoxy-2'-fluorocytidine is prepared by selective benzoylation with benzoic anhydride in anhydrous dimethylformamide, V. Bhat, et al. *Nucleosides Nucleotides,* Vol. 8, pp. 179–183 (1989). The 5'-O-(4,4'-dimethoxytrityl)-3'-O-(N,N-diisopropyl-b-cyanoetylphosphoramidite) can be prepared in accordance with Examples 65 and 66.

Example 69

N-2-Phenoxyacetyl-2'-Deoxy-2'-fluoro-5'-O-(4,4'-dimethoxytrityl)-guanosine-3'-O-(N,N-diisopropyl-β-cyanoethylphosphoramidite). (69)

2'-Deoxy-2'-fluoroguanosine is prepared according to the procedure of M. Ikehara, et al., *Chemical and Pharmaceutical Bulletin* Vol. 29, pp. 1034–1038 and pp. 3281–3285 (1981). 9-β-D-arabinofuranosylguanine is utilized as starting material, M. J. Robins, *Tetrahedron,* Vol. 40, pp. 125–135 (1984). After 2'-deoxy- 2'-fluoroguanosine is obtained, it is protected as the N-2-phenoxyacetyl derivative, K. K. Ogilvie, *Nucleic Acids Research,* Vol. 17, pp. 3501–3517, can then be converted to the 5'-DMT-3'-phosphor-amidite as described in Examples 65 and 66.

Example 70

$N^6$-Benzoyl-[2'-deoxy-2'-cyano-5'-O-(4,4'-dimethoxytrityl)]adenosine-3'-O-(N,N-diisopropyl-β-cyanoethylphosphoramidite) (70)

2'-Deoxy-2'-cyanoadenosine is prepared by the free radical replacement of the 2'-iodo group of 2'-deoxy-2'-iodo-3', 5'-O- disiloxytetraisopropyl)-$N^6$-benzoyladenosine according to a similar procedure described by K. E. B. Parkes and K. Taylor, *Tetrahedron Letters,* Vol. 29, pp. 2995–2996 (1988). 2'-Deoxy-2'-iodoadenosine was prepared by R. Ranganathan as described in *Tetrahedron Letters* Vol. 15, pp. 1291–1294 (1977), and disilyated as described by W. T. Markiewicz and M. Wiewiorowski in *Nucleic Acid Chemistry,* Part 3, pp. 222–231, Townsend, L. B.; Tipson, R. S. eds. (J. Wiley and Sons, New York, 1986). This material is treated with hexamethylditin, AIBN, and t-butylisocyanate in toluene to provide protected 2'-deoxy-2'-cyanoadenosine. This material, after selective deprotection, is converted to its 5'-DMT-3'-phosphor-amidite as described in Examples 65 and 66.

Example 71

2'-Deoxy-2'-cyano-5'-O-(4,4'-dimethoxytrityl)-uridine-3'-O-(N,N-diisopropyl-β-cyanoethyl phosphoramidite). (71)

2'-Deoxy-2'-iodouridine (or 5-methyluridine), 3',5'-disilylated as described above, is converted to the 2'-iodo derivative by triphenylphosphonium methyl iodide treatment as described by K. E. B. Parkes and K. Taylor, *Tetrahedron Letters* Vol. 29, pp. 2995–2996 (1988). Application of free radical reaction conditions as described by K. E. B. Parkes and K. Taylor, *Tetrahedron Letters,* Vol. 29, pp. 2995–2996 (1988), provides the 2'-cyano group of the protected nucleoside. Deprotection of this material and subsequent conversion to the protected monomer as described in examples 65 and 66 above provides the requisite nucleic acid synthesizer material.

Example 72

2'-Deoxy-2'-cyano-5'-O-(4,4'-dimethoxytrityl)-cytidine-3'-O-(N,N-diisopropyl-β-cyanoethylphosphoramidite). (72)

2'-Deoxy-2'-iodocytidine is obtained via a conventional keto to amino conversion.

Example 73

2'-Deoxy-2'-cyano-5'-O-(4,4'-dimethoxytrityl)-guanosine-3'-O-(N,-N-diisopropyl-β-cyanoethylphosphoramidite). (73)

2'-Deoxy-2'-cyanoguanosine is obtained by the displacement of the triflate group in the 2'-up position (arabino sugar) of 3',5'-disilylated N2-isobutrylguanosine. Standard deprotection and subsequent reprotection such as through the methodologies of Examples 65 and 66 provides the title monomer.

Example 74

Preparation of 2'-Deoxy-2'-(trifluoromethyl) Modified Oligonucleotides.

The requisite 2'-deoxy-2'-trifluromethyribosides of nucleic acid bases A, G, U(T), and C are prepared by modifications of a literature procedure described by Q.-Y. Chen and S. W. Wu in the *Journal of Chemical Society Perkin Transactions,* pp. 2385–2387 (1989). Standard procedures, as described in Examples 65 and 66 are employed to prepare the 5'-DMT and 3'-phosphoramidites as listed below.

A. $N^6$-Benzoyl-[2'-deoxy-2'-trifluoromethyl-5'-O-(4,4'-dimethoxytrityl)]adenosine-3'-O-(N,N-diisopropyl-β-cyanoethylphosphoramidite).
B. 2'-Deoxy-2'-trifluoromethyl-5'-O-(4,4'-dimethoxy-trityl)-uridine-3'-O-(N,N-diisopropyl-β-cyano-ethylphosphoramidite).
C. 2'-Deoxy-2'-trifluoromethyl-5'-O-(4,4'-dimethoxy-trityl)-cytidine-3'-O-(N,N-diisopropyl-β-cyano-ethylphosphoramidite).
D. 2'-Deoxy-2'-trifluoromethyl-5'-O-(4,4'-dimethoxy-trityl)-guanosine-3'-O-(N,N-diisopropyl-β-cyano-ethylphosphoramidite).

Example 75

Preparation of 2'-Deoxy-2'-(trifluoromethoxy) Modified Oligonucleotides.

The requisite 2'-deoxy-2'-O-trifluromethyribosides of nucleic acid bases A, G, U(T), and C are prepared by modifications of literature procedures described by B. S. Sproat, et al., *Nucleic Acids Research,* Vol. 18, pp. 41–49 (1990) and H. Inoue, et al., *Nucleic Acids Research,* Vol. 15, pp. 6131–6148 (1987). Standard procedures, as described in Example 1A, are employed to prepare the 5'-DMT and 3'-phosphoramidites as listed below.

A. N6-Benzoyl-[2'-deoxy-2'-(trifluoromethoxy)-5'-O-(4,4'-dimethoxytrityl)]adenosine-3'-O-(N,N-diisopropyl-β-cyanoethylphosphoramidite).
B. 2'-Deoxy-2'-(trifluoromethoxy)-5'-O-(4,4'-dimethoxytrityl)-uridine-3'-O-(N,N-diisopropyl-β-cyano-ethylphosphoramidite).
C. 2'-Deoxy-2'-(trifluoromethoxy)-5'-O-(4,4'-dimethoxytrityl)-cytidine-3'-O-(N,N-diisopropyl-β-cyanoethylphosphoramidite).
D. 2'-Deoxy-2'-(trifluoromethoxy)-5'-O-(4,4'-dimethoxytrityl)-guanosine-3'-O-(N,N-diisopropyl-β-cyano-ethylphosphoramidite).

Example 76

Preparation of 2'-Deoxy-2'-(1-proproxy) Modified G, U (T) and C Oligonucleotides.

The requisite 2'-deoxy-2'-O-propyl ribosides of nucleic acid bases G, U(T), and C are prepared by routine modification of examples 17 and 18. Also see, B. S. Sproat, et al., *Nucleic Acids Research,* Vol. 18, pp. 41–49 (1990) and H. Inoue, et al., *Nucleic Acids Research* Vol. 15, pp. 6131–6148 (1987). The procedures, as described in Examples 65 and 66 or examples 19 and 20 are employed to prepare the 5'-DMT and 3'-phosphoramidites as listed below.

A. 2'-Deoxy-2'-(1-proproxy)-5'-O-(4,4'-dimethoxy-trityl)-uridine-3'-O-(N,N-diisopropyl-β-cyano-ethylphosphoramidite).
B. 2'-Deoxy-2'-(1-proproxy)-5'-O-(4,4'-dimethoxy-trityl)-cytidine-3'-O-(N,N-diisopropyl-β-cyanoethylphosphoramidite).
C. 2'-Deoxy-2'-(1-proproxy)-5'-O-(4,4'-dimethoxy-trityl)-guanosine-3'-O-(N,N-diisopropyl-β-cyanoethylphosphoramidite).

Example 77

Preparation of 2'-Deoxy-2'-(vinyloxy) Modified Oligonucleotides

The requisite 2'-deoxy-2'-O-vinyl ribosides of nucleic acid bases A, G, U(T), and C are prepared by modifications of the procedures of example 1. In this case 1,2-dibromoethane is coupled to the 2'-hydroxyl and subsequent dehydrobromination affords the desired blocked 2'-vinyl nucleoside. Standard procedures, as described in Examples 65 and 66 are employed to prepare the 5'-DMT and 3'-phosphoramidites as listed below.

A. $N^6$-Benzoyl-[2'-deoxy-2'-(vinyloxy)-5'-O-(4,4'-dimethoxy-trityl)]adenosine-3'-O-(N,N-diisopropyl-β-cyanoethylphosphoramidite).
B. 2'-Deoxy-2'-(vinyloxy)-5'-O-(4,4'-dimethoxy-trityl)-uridine-3'-O,N,N-diisopropyl-β-cyanoethyl phosphoramidite.
C. 2'-Deoxy-2'-(vinyloxy)-5'-O-(4,4'-dimethoxy-trityl)-cytidine-3'-O-(N,N-diisopropyl-β-cyanoethylphosphoramidite).
D. 2'-Deoxy-2'-(vinyloxy)-5'-O-(4,4'-dimethoxy-trityl)-guanosine-3'-O-(N,N-diisopropyl-β-cyanoethylphosphoramidite).

Example 78

Preparation of 2'-Deoxy-2'-(allyloxy) Modified G, U(T), and C Oligonucleotides

The requisite 2'-deoxy-2'-O-allyl ribosides of nucleic acid bases G, U(T), and C are prepared by modifications of the procedures of example 21. Also see B. S. Sproat, et al., *Nucleic Acids Research* Vol. 18, pp. 41–49 (1990) and H. Inoue, et al., *Nucleic Acids Research* Vol. 15, pp. 6131–6148 (1987). The procedures, described in Examples 65 and 66 or 23 and 24 are employed to prepare the 5'-DMT and 3'-phosphoramidites as listed below.

A. $N^6$-Benzoyl-[2'-deoxy-2'-(allyloxy)-5'-O-(4,4'-dimethoxytrityl)]adenosine-3'-O-(N,N-diisopropyl-β-cyanoethylphosphoramidite).
B. 2'-Deoxy-2'-(allyloxy)-5'-O-(4,4'-dimethoxy-trityl)-uridine-3'-O-(N,N-diisopropyl-β-cyanoethylphosphoramidite).
C. 2'-Deoxy-2'-(allyloxy)-5'-O-(4,4'-dimethoxy-trityl)-cytidine-3'-O-(N,N-diisopropyl-β-cyanoethylphosphoramidite).
D. 2'-Deoxy-2'-(allyloxy)-5'-O-(4,4'-dimethoxy-trityl)-guanosine-3'-O-(N,N-diisopropyl-β-cyanoethylphosphoramidite).

Example 79

Chemical conversion of an thymine or cytosine (pyrimidine type base) to its β-D-2'-deoxy-2'-substituted erythropentofuranosyl nucleoside; 2'-substituted ribosylation).

The thymine or cytosine type analogs are trimethylsilylated under standard conditions such as hexamethyldisilazane (HMDS) and an acid catalyst (ie. ammonium chloride) and then treated with 3,5-O-ditoluoyl-2-deoxy-2-substituted-α-D-erythropento-furanosyl chloride in the presence of Lewis acid catalysts (ie. stannic chloride, iodine, boron tetrafluoroborate, etc.). A specific procedure has recently been described by J. N. Freskos, *Nucleosides & Nucleotides* Vol. 8, pp. 1075–1076 (1989) in which copper (I) iodide is the catalyst employed.

Example 80

Chemical conversion of an adenine or guanine (purine type base) to its β-D-2'-deoxy-2'-substituted erythropentofuranosyl nucleoside; 2'-substituted ribosylation)

The protected purine type analogs are converted to their sodium salts via sodium hydride in acetonitrile and are then treated with 3,5-O-ditoluoyl-2-deoxy-2-substituted-α-D-erythropentofuranosyl chloride at ambient temperature. A specific procedure has recently been described by R. K. Robins et al., *Journal of American Chemical Society* Vol. 106, p. 6379 (1984).

Example 81

Conversion of 2'-deoxy-2-substituted thymidines to the corresponding 2'-deoxy-2'-substituted cytidines (chemical conversion of an pyrimidine type 4-keto group to an 4-amino group).

The 3',5'-sugar hydroxyls of the 2' modified nucleoside types are protected by acyl groups such as toluoyl, benzoyl, p-nitrobenzoyl, acetyl, isobutryl, trifluoroacetyl, etc. using standard conditions of the acid chlorides or anhydrides and pyridine/dimethyl-amino pyridine solvent and catalyst. The protected nucleoside is now chlorinated with thionyl chloride or phosphoryl chloride in pyridine or other appropriate basic solvents. The pyrimidine type 4-chloro groups are now displaced with ammonium in methanol. Deprotection of the sugar hydroxyls also takes place. The amino group is benzoylated by the standard two-step process of complete benzylation (sugar hydroxyls and amino group) and the acyls are selectively removed by aqueous sodium hydroxide solution. Alternatively, the in situ process of first treating the nucleoside with chlorotrimethylsilane and base to protect the sugar hydroxyls from subsequent acylation may be employed. K. K. Ogilvie, *Can J. Chem.* Vol. 67, pp. 831–839 (1989). Another conversion approach is to replace the pyrimidine type 4-chloro group with an 1,2,4-triazolo group which remains intact throughout the oligonucleotide synthesis on the DNA synthesizer and is displaced by ammonium during the ammonium hydroxide step which removes the oligonucleotide from the CPG support and deprotection of the heterocycles. Furthermore, in many cases the pyrimidine type 4-chloro group can utilized as just described and replaced at the end of the oligonucleotide synthesis.

Example 82

Methyl-5-(cyanomethyl)-1-(2'-deoxy-3,5-di-O-p-toluoyl-β-D-erythropentofuranosyl)imidazole-4-carboxylate (82-A) and 5-cyanomethyl-1-(2'-deoxy-β-D-erythro-pentofuranosyl) imidazole-4-carboxamide. (82-B)

A large scale synthesis of the methyl-5-(cyanomethyl)-1-(2'-deoxy-3,5-di-O-p-toluoyl-β-D-erythropentofuranosyl) imidazole-4-carboxylate (82-A), was undertaken according to the sodium-salt glycosylation procedure published by G. R. Revankar, et al. in *J. Med. Chem.* Vol. 27, pp. 1389–1396 (1984). In examples 83 to 85 below, the products of alkylation of this starting material are diastereomeric mixtures differing in configuration at the alkylated carbon. As such, these mixtures exhibit duplicate resonances for each proton in the 1H-NMR. The 5-cyanomethyl-1-(2'-deoxy-β-D-erythropentofuranosyl)imidazole-4-carboxamide (82-B), the product of reaction of 82A with liquid ammonia at 100° C., was prepared according to this same literature reference.

Example 83

Methyl 5-(cyano[nonyl]methyl)-1-(2'-deoxy-3,5-di-O-p-toluoyl-β-D-erythro-pentofuranosyl)imidazole-4-carboxylate (83).

A solution of 82-A (5.7 g, 11 mmol) in anhydrous acetonitrile (75 mL) was treated with sodium hydride (0.88 g, 60% in oil, washed with hexanes) at room temperature and under an atmosphere of argon. This suspension was stirred for 15 minutes and then treated with iodononane (7.5 mL, 37.4 mmol) using a syringe. The reaction mixture was stirred under these conditions for 6 hr; thin layer chromatography plates (ethyl acetate/hexanes, 3:2, v/v) showed the disappearance of starting material nucleoside and the appearance of two faster migrating products. The reaction was quenched with the addition of glacial acetic acid to pH 5 and then evaporated to dryness in vacuo to afford a yellow syrup. The syrup was dissolved in dichloromethane (150 mL) and the solution was washed with cold 0.1N HCl, water, and then dried over magnesium sulfate. Filtration of the desiccant and evaporation of the solvent afforded a yellow gum which was flash-chromatographed on silica gel (120 g) using ethyl acetate-hexanes (1:4 then 1:1). Fractions corresponding to the alkylated products were pooled and evaporated to yield 83 as a yellowish foam, 2.98 g (47%). 1H-NMR (Me$_2$SO-d6): δ, 8.18 and 8.15 (s,s; C-2 H, 1 H); 6.48 and 6.37 (t,t; H-1', 1 H); 1.18 and 0.90 (2 m, nonyl, 19 H).

Example 84

Methyl 5-(allyl[cyano]methyl)-1-(2'-deoxy-3,5-di-O-p-toluoyl-β-D-erythro-pentofuranosyl)imidazole-4-carboxylate (84)

A solution of 82-A (5.0 g, 9.7 mmol) in anhydrous acetonitrile (75 mL) was treated with sodium hydride (0.46 g, 11.6 mmol) and then allyl bromide (2.5 mL, 29 mmol) in the manner described for 83. The reaction was worked up and chromatographed on silica gel (75 g) using the aforementioned solvent system to afford 84 as a yellowish foam, 3.66 g (68%). 1H-NMR (Me$_2$SO-d6): δ, 8.15 and 8.13 (s,s; C-2 H, 1 H); 6.38 (m, H-1', 1 H); 5.75 and 5.08 (2 m, vinyl, 3 H).

Example 85

Methyl 5-(benzyl[cyano]methyl)-1-(2'-deoxy-3,5-di-O-p-toluoyl-β-D-erythro-pentofuranosyl)imidazole-4-carboxylate (85)

A solution of 82-A (5.0 g, 9.6 mmol) in anhydrous acetonitrile (75 mL) was treated with sodium hydride (0.46 g, 11 mmol) under argon and stirred at room temperature for 15 minutes. The mixture was cooled to 4° C. in an ice bath and a solution of benzyl bromide (1.26 mL, 10.6 mmol) in acetonitrile (15 mL) was added dropwise over 70 min. The ice bath was removed and the reaction further stirred at room temperature for 2.5 hr. Workup of the reaction and purification of the products on silica gel (100 g) afforded 85 as a white foam, 3.4 g (58%). 1H-NMR (Me$_2$SO-d6): δ, 8.10 and 8.05 (s,s; C-2 H, 1 H); 7.30–7.10 (m, phenyl, 5 H); 5.33 and 6.01 (t,t; H-1', 1 H).

Example 86

5-(Cyano[nonyl]methyl)-1-(2'-deoxy-β-D-erythropentofuranosyl)imidazole-4-carboxamide (86)

The nonyl-imidazole nucleoside 83 (2.98 g, 4.6 mmol) was dissolved in anhydrous methanol (5 mL) and transferred to a stainless steel bomb. The solution was cooled in a dry-ice/isopropanol bath and then treated with anhydrous liquid ammonia (45 mL). The bomb was sealed and then heated to 100° C. in an oil bath for 21 hr. TLC (ethyl acetate/methanol, 4:1, v/v) indicated a complete removal of the toluoyl protecting groups. Excess ammonia was evaporated at room temperature and the amber gum which resulted was flash chromatographed on silica gel (80 g) using ethyl acetate/methanol (95:5 then 9:1). Fractions corresponding to deblocked products were pooled and evaporated in vacuo to yield 86 as a white foam, 1.14 g (63%). 1H-NMR (Me$_2$SO-d6): δ, 8.09 and 8.05 (s,s; C-2 H, 1 H); 6.14 (t, H-1', 1H); 1.40–1.05 and 0.95 (2 m, nonyl, 19 H).

Example 87

5-(Allyl[cyano]methyl)-1-(2'-deoxy-β-D-erythropentofuranosyl)imidazole-4-carboxamide (87)

The allyl-imidazole nucleoside 84 (3.95 g, 7.08 mmol) was treated with liquid ammonia in a stainless steel bomb and heated to 100° C. for 8 hr. The products of this reaction were worked up and purified on silica gel (80 g) in a manner analogous to that for compound 86. The deblocked compound 87 was isolated as a white foam, 1.29 g (58%). 1H-NMR (Me$_2$SO-d6): δ, 8.09 and 8.07 (s,s; C-2 H, 1 H); 6.15 (t, H-1', 1 H); 5.75 and 5.10 (2 m, vinyl, 3 H).

Example 88

5-(Benzyl[cyano]methyl)-1-(2'-deoxy-β-D-erythropentofuranosyl)imidazole-4-carboxamide (88)

The benzyl-imidazole nucleoside 85 (3.0 g, 4.93 mmol) was treated with liquid ammonia in a stainless steel bomb and heated to 100° C. for 6 hr. The products of this reaction were worked up and purified on silica gel (80 g) in a manner analogous to that for compound 86. The deblocked compound 88 was isolated as a white foam, 1.03 g (59%). 1H-NMR (Me$_2$SO-d6): δ, 8.03 and 8.04 (s,s; C-2 H, 1 H); 7.25 (m, phenyl, 5 H); 6.17 and 6.07 (t,t; H-1', 1 H).

Example 89

5-(Cyanomethyl)-1-(2'-deoxy-5'-O-dimethoxytrityl-β-D-erythropentofuranosyl)imidazole-4-carboxamide (89)

The nucleoside 82-B (1.95 g, 7.3 mmol) was dried by coevaporation with pyridine (30 mL). The gum which resulted was dissolved in anhydrous pyridine under argon and then treated with dimethoxytrityl chloride (2.90 g, 12.4 mmol). The mixture was stirred at room temperature for 2 hr after which TLC (ethyl acetate:methanol, 19:1, v/v) indicated complete conversion of starting material. Tritylated products were visualized as orange spots using H$_2$SO$_4$ fumes. The reaction was quenched with the addition of methanol (2 mL) followed by stirring for 15 min. The mixture was evaporated in vacuo to afford a thick orange syrup which was coevaporated with toluene (3×25 mL). The syrup was flash chromatographed on silica gel (100 g) using a stepwise gradient of methanol in 1% Et$_3$N/CH$_2$Cl$_2$ (0 to 5% methanol). The appropriate fractions were pooled and evaporated to yield 89 as a white foam, 3.64 g (87%). 1H-NMR (Me$_2$SO-d6): δ, 7.96 (s, C-2 H, 1 H); 6.85–7.35 (m, DMT, 13 H); 6.13 (t, H-1', 1 H).

Example 90

5-(Cyano[nonyl]methyl)-1-(2'-deoxy-5'-O-dimethoxytrityl-β-D-erythropentofuranosyl) imidazole-4-carboxamide (90)

The nucleoside 86 (1.20 g, 3.1 mmol) was thoroughly dried by coevaporation with anhydrous pyridine (30 mL). The syrup which resulted was redissolved in anhydrous pyridine under argon and treated with dimethoxytrityl chloride (1.0 g, 3.1 mMol). The reaction mixture was stirred at room temperature for 3.5 hr, after which time TLC (ethyl acetate) indicated complete conversion of the starting material. The reaction mixture was treated with 2 mL of anhydrous methanol, stirred for 15 minutes and then evaporated in vacuo to afford a bright orange syrup. This syrup was coevaporated with toluene (2×50 mL) and then flash chromatographed on silica (80 g) using a stepwise gradient of methanol in dichloromethane/1% triethyl-amine (0 to 3% methanol). The appropriate fractions were pooled and evaporated in vacuo to yield the dimethoxy-tritylated compound 90 as a white foam, 1.46 g (69%). 1H-NMR (Me$_2$SO-d6): δ, 7.98 and 7.93 (s,s; C-2 H, 1 H); 7.30 and 6.92 (2 m, DMT, 13 H); 6.21 (t, H-1', 1 H); 1.20 and 0.92 (2 m, nonyl, 19 H).

Example 91

5-(Allyl[cyano]methyl)-1-(2'-deoxy-5'-O-dimethoxytrityl-β-D-erythropentofuranosyl) imidazole-4-carboxamide (91)

The nucleoside 87 (1.25 g, 4.08 mmol) was dried by coevaporation with pyridine and then redissolved in anhydrous pyridine (50 mL) and treated with dimethoxytrityl chloride (1.38 g, 4.08 mmol) under an atmosphere of argon. The reaction was stirred for 2.5 hr and then worked up and products isolated by flash chromatography on silica gel (90 g) in a manner analogous to compound 89. The appropriate fractions were pooled and evaporated in vacuo to yield dimethoxytritylated compound 91 as a white foam, 1.86 g (75%). 1H-NMR (Me$_2$SO-d6): δ, 7.98 and 7.95 (s,s; C-2 H, 1 H); 7.25 and 6.93 (2 m, DMT, 13 H); 6.21 (m, H-1', 1 H); 5.78 and 5.10 (2 m, vinyl, 3 H).

Example 92

5-(Benzyl[cyano]methyl)-1-(2'-deoxy-5'-O-dimethoxytrityl-β-D-erythropentofuranosyl) imidazole-4-carboxamide (92)

The nucleoside 88, 930 mg (2.6 mmol) was dried by coevaporation with pyridine and then redissolved in anhydrous pyridine (50 mL) and treated with dimethoxytrityl chloride (884 mg, 2.6 mmol) under an atmosphere of argon. The reaction was stirred for 4 hr and then worked up and the products isolated by flash chromatography on silica gel (80 g) in a manner analogous to compound 89. The appropriate fractions were pooled and evaporated in vacuo to yield 1.50 g of 92 as a pinkish foam, (87%). 1H-NMR (Me$_2$SO-d6): δ, 7.70 (s, C-2 H, 1 H); 7.40 and 6.70 (2 m; DMT, phenyl;18 H); 6.10 (t, H-1', 1 H).

Example 93

5-(Cyanomethyl)-1-(5'-O-dimethoxytrityl-3'-O-[2-cyanoethyl-N,N-diisopropyl]phosphoramidite-2'-deoxy-β-D-erythropentofuranosyl)imidazole-4-carboxamide (93)

The tritylated nucleoside 89 (1.82 g, 3.2 mmol) was dissolved in anhydrous tetrahydrofuran (50 mL) under argon and then treated with diisopropyl ethylamine (1 mL). The solution was cooled to 4° C. in an ice bath and then treated with 2-cyanoethyl-N,N-diisopropyl phosphorochloridate (1.2 g, 5.12 mmol) in one portion. The ice bath was removed and the reaction mixture was stirred at room temperature for 3 hr. At the end of this time, TLC ($CH_2Cl_2$/1% MeOH/1% $Et_3N$) indicated complete conversion of starting material. Reaction products were visualized using $H_2SO_4$ fumes. The reaction mixture was evaporated in vacuo to afford a thick syrup which was immediately redissolved in dichloromethane (100 mL) and washed with cold, saturated sodium bicarbonate (2×50 mL) and brine (50 mL). The organic layer was dried over magnesium sulfate, filtered and evaporated to yield a yellowish foam (2.8 g). This foam was flash chromatographed on silica gel (75 g) using a stepwise gradient of ethyl acetate/hexanes (1:4 to 1:1) containing 1% $Et_3N$. The appropriate fractions were pooled and evaporated to yield 93 as a white foam, 1.65 g (59%). An aliquot of this material was precipitated by dissolving the foam in a small volume of dichloromethane and adding it to a large proportion (1:50) of hexanes. 1H-NMR ($CD_3CN$): δ, 7.78 and 7.72 (s,s; C-2 H, 1H); 7.25 and 6.95 (m, DMT, 13 H); 6.12 (t, H-1', 1H). 31P-NMR ($CD_3CN$): δ, 150.02, 149.98.

Example 94

5-(Cyano[nonyl]methyl)-1-(5'-O-dimethoxytrityl-3'-O-[2-cyanoethyl-N,N-diisopropyl]phosphoramidite-2'-deoxy-β-D-erythropentofuranosyl)imidazole-4-carboxamide (94)

The tritylated nucleoside 90, 1.46 g (2.1 mmol) was dissolved in anhydrous tetrahydrofuran (50 mL) under argon and then treated with diisopropyl ethylamine (1.5 mL). This mixture was cooled to 4° C. in an ice bath and then treated with 2-cyanoethyl-N,N-diisopropylamino phosphorochloridite (488 mg, 2.1 mmol) in one portion. The ice bath was removed and the reaction was further stirred at room temperature for a total of 3 hr. Additional phosphorochloridite (48 mg) was added at the end of the first and second hours of reaction. At the end of this time, TLC ($CH_2Cl_2$/3% MeOH/1% $Et_3N$) indicated complete conversion of starting material. The reaction mixture was worked up as described for 93 and the products purified on silica gel (80 g) using a stepwise gradient of ethyl acetate/hexanes (2:3 to 3:2) containing 1% $Et_3N$. The appropriate fractions were pooled and evaporated to afford 94 as a colorless foam, 1.37 g (73%). An aliquot of this material was precipitated using a procedure described for compound 93. 1H-NMR ($CD_3CN$): δ, 7.75 (s, C-2 H); 7.25 and 6.85 (2 m, DMT, 13 H), 6.25 and 6.20 (2 m, H-1', 1 H). $^{31}$P-NMR ($CD_3CN$): δ, 150.1, 150.0 and 149.9.

Example 95

5-(Ally[cyano]methyl)-1-(5'-O-dimethoxytrityl-3'-O-[2-cyanoethyl-N,N-diisopropyl]phosphoramidite-2'-deoxy-β-D-erythro-pentofuranosyl)imidazole-4-carboxamide (95)

The tritylated nucleoside 91, 1.86 g (3.1 mmol) was dissolved in anhydrous THF (50 mL) and then treated with diisopropyl ethylamine (1.5 mL) and 2-cyanoethyl N,N-diisopropylamino phosphochloridite (705 mg, 3.1 mmol) in a manner analogous to compound 94. The mixture was stirred at room temperature for a total of 3 hr. Additional phosphochloridite (140 mg) was added at the end of 2 hr reaction time. The reaction was worked up and the products isolated by flash chromatography on silica gel (80 g) using a stepwise gradient of ethyl acetate/hexanes (2:3 to 4:1, v/v). The appropriate fractions were pooled and evaporated to yield 2.18 g (88%) of 95 as a white solid foam. An aliquot of this material was precipitated using a procedure described for compound 93. 1H-NMR ($CD_3CN$): δ, 7.77 and 7.75 (s,s; C-2 H, 1 H); 7.45 and 6.85 (2 m, DMT, 13 H); 6.25 and 6.20 (t,t; H-1', 1 H). 31P-NMR ($CD_3CN$): δ, 150.05, 149.98 and 149.85.

Example 96

5-(Benzyl[cyano]methyl)-1-(5'-O-dimethoxytrityl-3'-O-[2-cyanoethyl-N,N-diisopropyl]phosphoramidite-2'-deoxy-β-D-erythro-pentofuranosyl)imidazole-4-carboxamide (96)

The tritylated nucleoside 92, 1.50 g (2.3 mmol) was dissolved in anhydrous THF (50 mL) and then treated with diisopropyl ethylamine (1.5 mL) and 2-cyanoethyl-N,N-diisopropylamino phosphochloridite (539 mg, 2.3 mmol) in a manner analogous to compound 93. The mixture was stirred at room temperature for a total of 3 hr. Additional phosphorochloridite (110 mg) was added at the end of 2 hr reaction time. The reaction was worked up and the products isolated by flash chromatography on silica gel (40 g) using a stepwise gradient of ethyl acetate/hexanes (1:4 to 3:2, v/v). The appropriate fractions were pooled and evaporated to yield 96, 1.03 g (55%) as a colorless foam. An aliquot of this material was precipitated using a procedure described for compound 93. 1H-NMR ($CD_3CN$): δ, 7.72 (s,s; C-2 H; 1 H); 7.30 and 6.80 (2 m; DMT, benzyl; 18 H); 6.10 (m, H-1', 1 H). $^{31}$P-NMR ($CD_3CN$): δ, 150.00, 149.90 and 149.85.

Example 97

Synthesis of Oligomers

Oligomers incorporating the nucleotides of examples 93, 94, 95 and 96 were made using standard phorphoramidite chemistries on an Applied Biosystems 380B synthesizer. Average coupling efficiencies were 94% using a method which left the 5'-dimethoxytrityl group of each oligonucleotide on. After cleavage from the solid support, the oligomers were treated with excess concentrated ammonium hydroxide and then heated in a sealed vessel at 55° C. for a minimum of 15 hr. This procedure removed all protecting groups from A, G and C bases and caused cyclization of the 5-cyano[alkyl]methyl imidazole to the 3-deaza-3-alkyl (or aryl) heterocycles. For each nucleotide, verification of this cyclization was made from the analysis of a 1H-NMR spectrum of a TG3C trimer containing a single 3-deaza-3-substituted 2'-deoxyguanosine base. Purification of these trityl-on oligomers was performed using a C-4 Waters Prepak cartridge (10 cm) using a gradient elution of acetonitrile in 50 mM triethyl ammonium acetate (pH 7.0) (4 to 48% over 60 min). The trityl group was removed by a treatment with 15% acetic acid and the oligomers were then precipitated from 70% ethanol.

Example 98

5-(Cyano[propylphthalimide]methyl)-1-(5'-O-dimethoxy-trityl-3'-O'[2-cyanoethyl-N,N-diisopropyl]phosphoramidite-2'-deoxy-β-D-erythro-pentofuranosyl-imidazole-4-carboxamide (98)

In a manner as per example 83 compound 82-A can be treated with N-(3-bromopropyl)phthalimide instead of iodononane. After work-up as per example 83 the product can be treated as per examples 89 and 93 to yield the title compound. In addition to ring closure upon cleavage from the oligonucleoside synthesizer solid support, the phthalimide is also cleaved to amino as per other above examples. Further the alkylamino product can be chain extended to a polyalkylamine as per examples 57 and 58.

Example 99

5-(Cyano[imidizo-1-yl(propyl)]methyl)-1-(5'-O-dimethoxy-trityl-3'-O'[2-cyanoethyl-N,N-diisopropyl]phosphoramidite-2'-deoxy-β-D-erythro-pentofuranosyl-imidazole-4-carboxamide (99)

In a manner as per example 83 compound 82-A can be treated with 1-(3-bromopropyl)imidazole instead of iodononane. After work-up as per example 83 the product can be treated as per examples 89 and 93 to yield the title compound.

Example 100

5-(Cyano[anthracen-2-yl(propyl)]methyl)-1-(5'-O-dimethoxy-trityl-3'-O'[2-cyanoethyl-N,N-diisopropyl]phosphoramidite-2'-deoxy-β-D-erythro-pentofuranosyl-imidazole-4-carboxamide (100)

In a manner as per example 83 compound 82-A can be treated with 2-(3-bromopropyl)anthracene instead of iodononane. After work-up as per example 83 the product can be treated as per examples 89 and 93 to yield the title compound.

Example 101

2-chloro-6-allyloxy-9-2'-deoxypurine (101)

To a stirred suspension of 2,6-dichloro-9-(2'deoxy-3',5'-di-o-toluyl)-purine (10.3 g, 19.04 mmol) in allyl alcohol (150 ml) was added sodium hydride (0.8 g, 20 mmol) in small portions over 10 minutes period at room temperature. After the addition of sodium hydride, the reaction mixture was placed in a preheated oil bath at 55° C. for 20 minutes with exclusion of moisture. The reaction mixtrue was cooled, filtered and washed with allyl alcohol (100 ml). To the filtrate IRC-50 (weakly acidic) H⊕ resin was added until the pH of the solution becomes 4–5. The resin was filtered, washed with methanol (100 ml) and the filtrate was evaporated to dryness. The residue was adsorbed on silica gel (10 g, 60–100 mesh) and evaporated to dryness. The dried silica gel was placed on top of silica column (5×25 cm, 100–250 mesh) packed in dichloro-methane. The column was eluted with $CH_2Cl_2 \rightarrow$ acetone. The fractions having the product was pooled together and evaporated to dryness to give 6 g (96%) of the title compound as foam.

Example 102

2-chloro-2'-deoxy inosine (102)

A mixutre of (101) (6 g, 18.4 mmol), pd/c (10%, 1 g) and triethyl amine (1.92 g, 19 mmol) in ethyl alcohol (200 ml) was hydrogenated at atmospheric pressure during 30 minutes periods at room temperature. The reaction mixture was filtered, washed with MeOH (50 ml) and the filtrate evaporated to dryness. The product (5.26 g, 100%) was found to be moisture sensitive and remains as an oil. The oil was used as such for further reaction without purification.

Example 103

$N_2$-[Imidazol-1-yl-(propyl)]-2'-deoxyguanosine (103)

A solution of the nucleoside 102 (10.31 g, 36 mmol) and 1-(3-amino-propyl) imidazol (9 g, 72 mmole) in 2-methoxyethanol (60 ml) was heated in a steel bomb at 120° C. (oil bath) for 24 hrs. The bomb was cooled to 0° C., opened carefully and the precipitated solid was filtered. The solid was washed with methanol (50 ml) and acetone (50 ml), and dried over sodium hydroxide to give 9 g (67%) of pure 103. A small amount was recrystallized from DMF for analytical purposes. mp 245–47°.

Example 104

$N_2$,3',5'-Tn-0-isobutyryl-$N_2$-[imidazol-1-yl (propyl)]-2'-deoxygunaosine (104)

To a well dried solution of the substrate 103 (1.5 g, 4 mmole) and triethylamine (1.62 g, 16 mmol) in dry pyridine (30 ml) and dry DMF (30 ml) was added isobutyryl chloride (1.69 g, 16 mmol) at room temperature. The reaction mixture was allowed to stir at room temperature for 12 hrs and evaporated to dryness. The residue was partitioned between dichloromethane and water (100 ml) and extracted with $CH_2Cl_2$ (2×200 ml). The organic extract was washed with brine (100 ml) and dried over anhydrons magnesium sulfate. The dried organic extract was evaporated to dryness and the residue was purified over flash chromatography using $CH_2Cl_2 \rightarrow$ MeOH as the eluent. The prue fractions were pooled and evaporated to dryness to give 1.8 g (77%) of the title compound as colorless crystals from $CH_2Cl_2$/MeOH. mp 210–12° C.

Example 105

6-0-[2-nitrophenyl, ethyl]-$N_2$,3',5'-Tn-0-isobutyryl-$N_2$-[imidazol-1-yl(propyl)]-2'-deoxyguanosine (105)

To a stirred solution of 104 (2.0 g, 3.42 mmol), triphenyl phosphine (2.58 g, 10.26 mmol) and p-nitrophenyl ethanol (1.72 g, 10.26 mmol) in dry dioxane was added dicthylazodicarboxylate (1.78 g, 10.26 mmol) at room temperature. The reaction mixture was stirred at room temperature for 12 h and evaporated to dryness. The residue was purified by flash chromatography over silica gel using $CH_2Cl_2 \rightarrow$ acetone as the eluent. The pure fractions were pooled together and evaporated to dryness to give 2.4 g (96%) of 6 as amorphous solid.

Example 106

6-0-[2-(4-nitrophenyl)-ethyl]-$N_2$-isobutyryl-$N_2$-[imidazol-1-yl-(propyl)-2'-deoxyguanosine (106)

A stirred solution of 105 (9 g, 12.26 mmol) in methanol (250 ml) was treated with ammonium hydroxide (30%, 150 ml) at room temperature. The reaction mixture was stirred at room temperature for 12 h and evaporated to dryness. The residue was purified by flash chromatography over silica gel using $CH_2Cl_2 \rightarrow$ acetone as the eluent. The pure fractions were pooled together and evaporated to dryness to give 2.4 g (96%) of 105 as amorphous solid.

Example 107

5'-0-(4,4'-dimethoxytrityl)-6-0-[2-(4-nitrophenyl) ethyl]-$N_2$-isobutyryl-$N_2$-[imidazol-1-yl(propyl)-2'deoxyguanosine (107)

The substrate 106 (5.94 g, 10 mmol) was dissolved in dry pyridine (75 ml) and evaporated to dryness. This was repeated three times to remove traces of moisture. To this well dried solution of the substrate in dry pyridine (100 ml) was added dry triethylamine (4.04 g, 40 mmol), N,N-dimethylamino pyridine (10.14 g, 30 mmol) at room temperature. The reaction mixture was stirred at room temperature for 12 hrs under argon atmosphere. Methanol (50 ml) was added and the stirring was continued for 15 minutes. The mixture was evaporated to dryness. The residue was purified by flash chromatography over silica gel using $CH_2Cl_2 \rightarrow$ acetone containing 1% triethylamine as the eluent. The pure fractions were pooled together and evaporated to dryness to give 7.2 g (80%) of (107) as colorless foam.

Example 108

3'-0-[N,N-dissopropylamino) (β-cyanoethoxy) phosphanyl]-5'-0-(4,4'-dimethoxytrityl)-6-0-[2-(4-nitrophenyl)ethyl]-$N_2$-isobutyryl-$N_2$-[imidazol-1-yl (propyl)-2'-deoxyguanosine (108)

The substrate 107 (2.5 g, 2.7 mmol) was dissolved in dry pyridine (30 ml) and evaporated to dryness. This was repeated three times to remove remaining traces of water and dried over solid sodium hydroxide overnight. This dried 107 was dissolved in dry dichloromethane (30 ml) and cooled to 0° C. under argon atmosphere. To this cold stirred solution was added N,N-diisopropylethylamine (0.72 g, 5.6 mmol) followed by (β-cyanoethoxy)chloro(N,N-diisopropylamino) phosphane (1.32 g, 5.6 mmol) dropwise over a period of 15 minutes. The reaction mixture was stirred at 0° C. for 1 hr and at room temperature for 2 hr. The reaction mixture was diluted with dichloromethane (100 ml) and washed with brine (50 ml). The organic extract was dried over anhydrous magnesium sulfate and evaporated to dryness. The residue was purified by flash chromatography over silica gel using hexane→acetone containing 1% triethylamine as the eluent. The main fractions were collected and evaporated to dryness. The residue was dissolved in dry dichloro-methane (10 ml) and added dropwise, into stirred solution of hexane (15-ml), during 30 minute period. After the addition, the stirring was continued for an additional 1 hr at room temperature under argon. The precipitated solid was filtered and dried over solid NaOH under vacuum overnight to give 2 g (65%) of the title compound as colorless powder.

Example 109

$N_2$-[imidazol-1-yl(propyl)]-2'-deoxyadenosine (109)

A suspension of 2-chloro-2'-deoxyadenosine (10.68 g, 37.4 mmole) and 1-(3-aminopropyl)imidazole (12.5 g, 100 mmole) in 2-methoxyethanol (80 ml) was heated at 125° C. for 45 hrs in a steel bomb. The bomb was cooled to 0° C., opened carefully and evaporated to dryness. The residue was co-evaporated several times with ethanol and toluene. The residue was dissolved in ethanol, which on cooling gave a precipitate. The precipitate was filtered and dried. The filtrate was evaporated to dryness and the residue was carried over to the next reaction without characterization.

Example 110

3',5'-O-(tetraisopropyldisiloxane-1-3-diyl)-$N_2$-[imidazole-1-yl(propyl)]-2'-deoxyadenosine (110)

The crude product (14.03 g) from example 109 was dissolved in dry DMF (100 ml) and dry pyridine (50 ml) and evaporated to dryness. This was repeated three times to remove all the water. The dried substrate was dissolved in dry DMF (75 ml) and dry pyridine (75 ml) and allowed to stir at room temperature under an argon atmosphere. To this stirred solution was added dry triethylamine (10.1 g, 100 mmol) and dichloro-1,1,3,3-tetra-isopropyldisiloxane (Tipsicl) (15.7 g, 50 mmol) during a 15 minute period. After the addition of Tipsicl, the reaction mixture was stirred at room temperature overnight. The reaction mixture was evaporated to dryness. The residue was mixed with toluene (100 ml) and evaporated again. The residue was purified by flash chromatography over silica gel using methylene chloride→methanol as the eluent. The pure fractions were pooled and evaporated to dryness to give 12.5 g (54%) of 110 as an amorphous powder.

Example 111

3',5'-O-(tetraisopropyldisiloxane-1,3-diyl)$N_2$,$N_6$-di-isobutyloyl-$N_2$-[imidazol-1-yl(propyl)]-2'-deoxyadenosine (111)

A solution of compound 110 (12.0 g, 19.42 mmol) was allowed to stir at room temperature with triethylamine (10.1 g, 100 mmol) under an argon atmosphere. To this stirred solution in pyridine (100 ml) was added isobutyryl chloride (6.36 g, 60 mmol) dropwise during a 15 minutes period. The reaction mixture was stirred under argon for 10 hrs and evaporated to dryness. The residue was partitioned between dichloromethane/water and extracted with dichloromethane (2×150 mo). The organic extract was washed with brine (50 ml) and dried over anhydrous magnesium sulfate. The organic extract was evaporated to dryness and the residue was purified by flash chromatography over silica gel using methylene chloride→acetone as the eluent to give pure 111 as a foam.

Example 112

$N_2$,$N_6$-di-isobutyryl-$N_2$-[imidazol-1-yl(propyl)]-2'-deoxyadenosine (112)

The title compound will be prepared by exposure of compound 111 with tetrabutylammonium fluoride (5 equiv.) in dry tetrahydrofuran at room temperature. The reaction mixture on evaporation and purification by silica column chromatography will yield 112.

Example 113

5'-O-(4,4'-dimethoxytrityl)-$N_2$,$N_6$-di-isobutyryl-$N_2$-[imidazol-1-yl(propyl)]-2'-deoxyadenosine (113)

Compound 113 is prepared from compound 112 as per example 107 above.

Example 114

3'-O-[(N, N-diisopropylamino) (β-cyanoethoxy) prosphanyl]-5'-O-(4,4'-dimethoxytrityl)-$N_2$,$N_6$-di-isobutyryl-$N_2$-[imidazol-1-yl(propyl)]-2'-deoxyadenosine (113)

The phosphoramidite monomer 113 is prepared from compound 112 as per the procedure of example 109. The crude product is purified by silica gel chromatography.

Example 115

$N_2$-nonyl-2'-deoxyguanosine (115)

The compound 115 is prepared from compound 102 (9.5 g, 22 mmol) and nonylamine (9.58 g, 67 mmole) as per example 103. The crude product was evaporated to dryness and the residue was co-evaporated with a mixture of ethanol and toluene (three times). The resulting residue was dissolved in ethanol and cooled to yield a small amount of product. It was filtered and the filtrate evaporated to dryness. The residue was used without characterization.

Example 116

3',5',$N_2$-triisobutyoyl-$N_2$-nonyl-2'-deoxyguanosine (116)

The title compound 116 was prepared as per the procedure of example 111 utilizing compound 115 (18 g, 32.9 mmol), TEA (30.3 g, 300 mmole), isobutyryl chloride (21.2 g, 200 mmole) and dry pyridine (150 ml). The crude product was purified by flash chromatography over silica gel using methylene chloride→ethyl acetate as the eluent. The pure product was obtained as a foam in 40% yield.

Example 117

$N^2$-isobutyryl-$N_2$-nonyl-2'-deoxyguanosine (117)

A stirred solution of compound 116 (5 g, 6.61 mmol) in methanol (100 ml) was treated with concentrated ammonium hydroxide (30%, 100 ml) at room temperature. After 8 hours, the reaction mixture was evaporated to dryness and the residue was purified by flash chromatography using methylene chloride→methanol as the eluent. The pure fractions were pooled together and evaporated to a residue. The residue was crystallized from methylene chloride/acetone to give 1.5 g (49%) of 117.

Example 118

5'-O-(4,4'-dimethoxytrityl)-$N_2$-isobutyryl-$N_2$-nonyl-2'-deoxyguanosine (118)

Compound 118 was prepared from compound 117 by following the procedure of example 107 utilizing compound 117 (2.2 g, 4.75 mmole), DMTCl (1.69 g, 5 mmole), dry TEA (1.01 g, 10 mmole) and dry pyridine (70 ml). The crude compound was purified using flash chromatography and methylene chloride/methanol/TEA as the eluent. 2 g (55%) of pure product was obtained as a foam.

Example 119

3'-O-[(N,N-diisopropylamino) (β-cyanoethoxy) prosphanyl]-5'-O-(4,4'-dimethoxytrityl)-$N_2$,$N_6$-diisobutyryl-$N_2$-nonyl-2'-deoxyadenosine (119)

The phosphoramidite monomer compound 119 is prepared from 118 as per the procedure of example 109. The crude product is purified by silica gel chromatography.

Example 120

3',5'-O-(tetraisopropyldisiloxane-1,3-diyl)-2-chloro-2'-deoxyadenosine (120)

Compound 120 was prepared from 2-chloro-2'-deoxyadenosine as per the procedure of example 110 utilizing 2-chloro-2'-deoxyadenosine (4.3 g, 15.09 mmol), 1,3-dichloro-1,1,3,3-tetraisopropyldisiloxane (4.74 g, 15.1 mmol), dry TEA (3.05 g, 30.2 mmol) and dry pyridine (100 ml). The pure product was purified by flash chromatography using methylene chloride→acetone as the eluent to give 7.3 g (92%) of pure 120 as an amorphous solid.

Example 121

3',5'-O-(tetraisopropyldisiloxane-1,3-diyl) -2-chloro-$N_6$-benzoyl-2'-deoxyadenosine (120)

A well dried solution of compound 120 (8 g, 15 mmol) in dry pyridine was allowed to react with triethylamine (4.55 g, 45 mmol) and benzoyl chloride (6.3 g, 45 mmol) at room temperature for 12 hrs under an argon atmosphere. The reaction mixture was evaporated to dryness and the residue partitioned between methylene chloride/water and extracted in methylene chloride (2×150 ml). The organic extract was washed with brine (60 ml), dried and evaporated to dryness. The residue on purification by silica column gave 8.2 g (86%) of 121 as a foam.

Example 122

$N_6$-benzoyl-2-chloro-2'-deoxyadenosine (122)

To a stirred solution of compound 121 (7.9 g, 12.5 mmol) in dry THF (100 ml) was added a 1 M solution of tetrabutylammonium fluoride in THF (50 ml), 5 mmol) slowly during a 15 minute period at room temperature. The reaction was stirred for an additional 6 hrs and evaporated to dryness. The residue on purification by silica gel chromatography using methylene chloride→acetone gave 3.88 g (80%) of pure 122.

Example 123

5'-O- (4,4'-dimethoxytrityl)-$N_6$-benzoyl-2-chloro-2'-deoxyadenosine (123)

Compound 123 was prepared from compound 122 as per the procedure of example 107 using compound 122 (2.5 g, 6.43 mmol), DMTCl (2.37 g, 7 mmol), dry TEA (0.71 g, 7 mmol) and dry pyridine (100 ml). The crude product was purified by flash chromatography using methylene chloride→ethyl acetate containing 18 TEA as the eluent to give 3 g (68%) of pure 123 as a foam.

Example 124

3'-O-[(N,N-diisopropylamino) (β-cyanoethoxy) prosphanyl]-5'-O-(4,4'-dimethoxytrityl)-$N_6$-benzoyl-2-chloro-2'-deoxyadenosine (124)

The phosphoramidite monomer 124 is prepared from compound 123 as per the procedure of example 109 using compound 123 (2.4 g, 3.47 mmol), N,N-diisopropyl ethylamine (1.22 ml, 7 mmol), 2-cyanoethyl-N,N-diisopropyl-chloro-phosphoramide (1.65 g, 7 mmol) and dry methylene chloride (30 ml). The crude product was purified by is flash chromatography using hexane→ethyl acetate containing TEA (1%) as the eluent. The pure fractions were pooled together and evaporated to dryness. The residue was dissolved in 10 ml of dry methylene chloride and added dropwise into a well stirred hexane (1500 ml) under argon atmosphere. After the addition, stirring was continued for an additional 1 hr and the precipitated solid was filtered, washed with hexane and dried over solid sodium hydroxide for 3 hrs. The dried powder showed no traces of impurity on $^{31}$P spectrum.

Example 125

$N_2$-[imidazol-4-yl(ethyl)]-2'-deoxyguanosine (125).

A mixture of 2-chloro-2'-deoxyinosine (6.0 g, 20.97 mmol) and histamine (4.4 g, 40 mmol) in 2-methoxyethanol (60 ml) was heated in a steel bomb at 110° C. for 12 hrs. The bomb was cooled to 0° C., opened carefully and the precipitated solid was filtered. The solid was washed with methanol and acetone and crystallized from DMF/water to give 6 g (79%) of pure 125. mp 220–222° C.

Example 126

3',5'-O-(tetraisopropyldisiloxane-1,3-diyl)-$N_2$-[imidazol-4-yl(ethyl)]-2'-deoxyguanosine (126)

To a stirred solution of compound 125 (2.4 g, 6.65 mmol) in dry DMF (50 ml) and dry pyridine (20 ml) was added triethylamine (4.04 g, 40 mmol) followed by 1,3-dichloro-1,1,3,3-tetraisoproplydisiloxane (4.18 g, 13.3 mmol) at room temperature. The reaction mixture was stirred at room temperature overnight and evaporated to dryness. The residue on purification silica gel chromatography using methylene chloride→methanol as the eluent gave 3.2 g (80%) of 126 as an amorphous solid.

Example 127

3',5'-O-(tetraisopropyldisiloxane-1,3-diyl)-6-O-diphenylcarbamoyl-$N_2$-[1-diphenylcarbamoylimidazol-4-yl(ethyl)]-2'-deoxyguanosine (127)

To a solution of compound 126 (12.34 g, 20 mmol) in dry pyridine (50 ml) and dry DMF (200 ml) was added N,N- diisopropylethylamine (7.74 g, 60 mmol) and diphenylcarbamoyl chloride (11.55 g, 50 mmol) at room temperature. The reaction mixture was stirred at room temperature for 12 hrs under an argon atmosphere. It was evaporated to dryness and the residue was dissolved in methylene chloride (400 ml). The organic extract was washed with water (100 ml) and brine (50 ml), dried and evaporated to dryness. The residue was purified by flash chromatography over silica gel using methylene chloride→acetone as the eluent. The pure fractions were pooled together and evaporated to dryness to give 15 g (75%) of 127 as a foam.

Example 128

6-O-diphenylcarbamoyl-$N_2$-[1-diphenylcarbamoylimidazol-4-yl-(ethyl)]-2'-deoxyguanosine (128)

Compound 128 can be prepared from compound 127 by deblocking the "TIP" group selectively with tetrabutylammonium fluoride/pyridine/THF at room temperature.

Example 129

5'-O-(4,4'-dimethoxytrityl)-6-O-diphenylcarbamoyl-$N_2$-[1-diphenylcarbamoylimidazol-4-yl-(ethyl)]-2'-deoxyguanosine (129)

Compound 129 can be prepared from compound 128 as per the procedure of example 107.

Example 130

3'-O-[(N,N-diisopropylamino) (β-cyanoethoxy) prosphanyl]-5'-O-(4,4'-dimethoxytrityl)-6-O-diphenylcarbamoyl-$N_2$-[1-diphenylcarbamoylimidazol-4-yl-(ethyl)]-2'-deoxyguanosine (130)

Compound 130 can be prepared from compound 129 as per the procedure of example 108.

Example 131

Procedure for the attachment of modified 5'-dimethoxytriphenylmethyl ribonucleosides of the invention to the 5'-hydroxyl of nucleosides bound to CPG support The modified nucleosides that will reside in the terminal 3'- position of certain antisense oligonucleotides are protected as their 5'-DMT (the cytosine and adenine exocyclic amino groups are benzoylated and the guanine amino is isobutrylated) and treated with trifluoroacetic acid/bromoacetic acid mixed anhydride in pyridine and dimethylaminopyridine at 50° C. for five hours. The solution is evaporated under reduced pressure to a thin syrup which is dissolved in ethyl acetate and passed through a column of silica gel. The homogenous fractions were collected and evaporated to dryness. A solution of 10 ml of acetonitrile, 10 micromols of the 3'-O-bromomethyl-ester modified pyrimidine nucleoside, and one ml of pyridine/dimethylaminopyridine (1:1) is syringed slowly (60 to 90 sec) through a one micromole column of CPG thymidine (Applied Biosystems, INC.) that had previously been treated with acid according to standard conditions to afford the free 5'-hydroxyl group. Other nucleoside bound CPG columns could be employed. The eluent is collected and syringed again through the column. This process is repeated three times. The CPG column is washed slowly with 10 ml of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5'ester linkage connecting the pyrimidine modified nucleoside to the thymidine that was initially bound to the CPG nucleoside. In this manner, any modified nucleoside or generally any nucleoside with modifications in the heterocycle and/or sugar can be attached at the very 3'-end of an oligonucleotide sequence.

Example 132

Procedure for the conversion of modified nucleoside-5'-DMT-3'-phosphoramidites into oligonucleotides The polyribonucleotide solid phase synthesis procedure of B. S. Sproat, et al., *Nucleic Acids Research* Vol. 17, pp. 3373–3386 (1989) is utilized to prepare the modified oligonucleotides.

Example 133

Preparation of Modified Phosphorothioates Oligonucleotides

Substituted 5'-DMT nucleoside 3'-phosphoramidites prepared as per the above described Examples are inserted into sequence-specific oligonucleotide phosphorothioates as described by S. Beaucage et al., *Journal of American Chemical Society* Vol. 112, pp. 1253–1255 (1990) and B. S. Sproat, et al., *Nucleic Acids Research* Vol. 17, pp. 3373–3386 (1989).

Example 134

Preparation of Modified Phosphate Methylated oligonucleotides

The protection, tosyl chloride mediated methanolysis, and mild deprotection described by L. H. Koole et al., in the *Journal of Organic Chemistry* Vol. 54, pp. 1657–1664 (1989), is applied to substituted oligonucleotides to afford phosphate-methylated substituted oligonucleotides.

Example 135

The ability of modified oligonucleotides of the invention to hybridize to their complementary RNA or DNA sequences is determined by thermal melting analysis. Natural antisense oligonucleotides or those containing modifications at specific locations were added to either the DNA or the RNA complement at stoichiometric concentrations. The helix to coil transition was monitored by measuring absorbance at 260 nm vs. temperature. Measurements were made in 100 mM Na+, 10 mM phosphate, pH 7 and 0.1 mM EDTA; oligonucleotide concentrations were 4 µM. The melting temperature or $T_m$ is the temperature at which half the molecules are in the duplex state and half are single stranded. Reported $T_m$'s are the temperature at which dAbsorbance/dTemperature is maximum. Thermodynamic parameters of duplex formation were obtained from a non-linear least squares fit for the absorbance vs. temperature curves to a two state model with linear sloping baselines.

Each modification was incorporated into several oligonucleotide sequences ranging in length from 15 to 21 residues. The sequences studied were various 15 to 21 mer of target organism including papiloma virus, herpes virus, 5-LO, HIV and other testing sequences.

Oligonucleotides containing from one to five modifications were tested in addition to fully modified sequences. For each modified oligonucleotide, the $T_m$ was compared to that of the unmodified DNA analog. In addition comparisons were made to oligonucleotides having their phosodiester linkages modified via phosphorothioate substitution.

In this example the thermodynamic stability of certain of the novel modified oligonucleotides of the invention were determined by melting studies. Certain of these studies as shown in Table 2 below reveal that up to five pendant groups specifically placed within oligonucleotide sequences of 15 to 21 bases in length generally resulted in only a modest effect on $T_m$s compared with the unmodified parent oligonucleotides. The effects on $T_m$s were dependent on location in the sequence in that modifications placed near the 3'-end had less destablizing effects than 5'-end placements.

TABLE 2

THERMODYNAMIC STABILITY

| Modification | $T_m$ (delta $T_m$, C) |
|---|---|
| Sequence studied A'CC GA'C G'AT C'AT GTC GTA' CGC (SEQ ID NO: 2) (21 mer, positions 1, 5, 8, 11 & 18 modified) | |
| natural | 67 |
| P = S (1–20) | 57 (–10) |
| 2'-O-nonyl | 51 (–16) |
| 2'-O-aminopropyl | 61 (–6) |
| 2'-O-fluoro | 67 (0) |
| 2'-O-allyl | 58 (–9) |
| Sequence studied CGA CTA TGC AAG TA'C (SEQ NO: 3) (15 mer, position 14 modified) | |
| natural | 53 |
| P = S (1–14) | 46 (–7) |
| 2'-O-nonyl | 54 (+1) |
| 2'-t-butyldimethylsilyl | 52 (–1) |
| 2'-O-aminopropyl | 53 (0) |
| 2'-O-aminobutyl | 53 (0) |
| RNA | 46 |
| 2'-O-allyl | 45 (–1) |
| 2'-O-benzyl | 45 (–1) |
| Sequence studied CGA CTA TGC AAA' A'A'C (SEQ NO: 4) (15 mer, positions 12, 13, 14 modified) | |
| natural | 52 |
| P = S (1–14) | 45 (–17) |
| 2'-O-nonyl | 49 (–3) |
| 2'-t-butyldimethylsilyl | 45 (–17) |
| 2'-O-aminopropyl | 54 (+2) |
| 2'-O-allyl | 51 (–1) |

Example 136

In this test specificity of hybridization was determined by comparing stability of a duplex containing an oligonucleotide modified at a single residue and its complement to the stability of a duplex containing the same singly modified oligonucleotide and a complementary sequence containing a not-complementary base opposite the modification. For example, specificity of an unmodified adenosine was determined by measuring the $T_m$ of the sequence [CTC GTA CCA TCC CCG TCC] CTC GTA CCA TCC CGG TCC (SEQ ID NO:5) (X strand) hybridized to the sequence GGA CCG GAA YGG TAC GAG (SEQ ID NO:6) (Y strand) where Y=A, C, G, T or none. The difference in $T_m$ for the matched duplex (Y=T) compared to the duplex containing a single mismatch or bulge (Y=A, C, G or none) is a measure of the specificity of the unmodified A-T pair. Similar experiments were performed with a modified adenosine replacing the A in position 9 of X strand. Comparison of the delta $T_m$'s (mismatch vs. match) for the modified sequence to those for the unmodified analog yields a measure of specificity of that modification.

In this test the specificity of the modified adenosines to Watson-Crick base pair with thymidine was determined by preparing as a Y stand, an 18 mer with a T (Watson-Crick complement), A, G, C (mismatch), or the deletion of the nucleotide at the 9 position (bulge loop) The X complement strand contains a 2'-modified adenosine at the 9th position. The data is shown in Table 3. As per Table 3, specificity of the modified adenosines were retained, i.e. their $T_m$'s were greater when paired with T rather than the mismatch situations of A, G, C or bulge loop.

TABLE 3

SPECIFICITY OF MODIFICATION
X STRAND 5'-CTC GTA CCA' TTC CGG TCC (SEQ ID NO:5)
Y STRAND 3'-GAG CAU GGY' AAG GCC AGG (SEQ ID NO: 7) (18 mer, 9-position modified)
Y = T (Watson-Crick COMPLEMENT)
Y = A, C OR G (MISMATCH)
Y = NONE (BULGE LOOP, "Bu")

| | $T_m$ (delta $T_m$, C) | | | | |
|---|---|---|---|---|---|
| Modification | A-T, | A-A, | A-G, | A-C, | A-Bu |
| natural | 63 | –9, | –6, | –14, | –12 |
| 2'-O-nonyl | 58 | –3, | –3, | –6, | –3 |
| 2'-t-butyldimethylsilyl | 58 | –4, | –4, | –2, | –4 |
| 2'-O-aminopropyl | 60 | –6, | –6, | –12, | –7 |
| 2'-fluoro | 61 | –10, | –7, | –14, | –10 |
| 2'-O-allyl | 60 | –8, | –6, | –13, | –10 |
| 2'-O-benzyl | 59 | –6, | –6, | –12, | –7 |
| 2'-O-methyl | 60 | –8, | –6, | –13, | –10 |
| 2'-chloro | 60 | –4, | –4, | –13, | –7 |
| | G-C, | G-A, | G-G, | G-T, | G-Bu |
| natural | 63 | –7, | –6, | –4, | –11 |
| 3-deazaguanosine | 59 | –2, | +1, | –1, | –7 |

Example 137

In this example resistance to nuclease degradation is measured. Aliquots of 10% fetal calf serum in DMEM media were incubated at 37° C. containing 50 $\mu$M oligonucleotide. At various times, 15 $\mu$l aliquots were removed and mixed with 15 $\mu$l 9 M urea in 1× TBE. Time points were frozen until analysis via 20% polyacrylamide/7M urea electrophoresis. Gels were stained with "Stains All" (Sigma Chem Co., St. Louis, Mo.) and following destaining, scanned using a LKB Laser Densitometer. Scans were analyzed by integration of bank peaks and calculations of % degraded from the full length oligonucleotide (n) to the loss of two base residues (n–2). Data was plotted as % degraded vs time and compared to curves generated for phosphodiester (PO) and phosphorothioate (PS) oligonucleotides.

For this example the data is shown in Table 4. As per this data the modified oligonucleotides of the invention are at least as resistant as unmodified sequences and in certain instances more resistant than phosphorothioate modified sequences.

TABLE 4

NUCLEASE RESISTANCE

| Modification | T ½ (hr) |
|---|---|
| Sequence studied CGA CTA TGC AAG TA'C (SEQ ID NO: 3) (15 mer, position 14 modified) | |
| natural | 1.2 |
| P = S (1–14) | 2.3 |
| 2'-O-nonyl | 5.8 |
| 2'-t-butyldimethylsilyl | 7 |
| 2'-O-aminopropyl | 7 |

TABLE 4-continued

NUCLEASE RESISTANCE

| Modification | T ½ (hr) |
|---|---|
| Sequence studied CGA CTA TGC AAA' A'A'C (SEQ ID NO:4) (15 mer, positions 12,13,14 modified) | |
| natural | 1.0 |
| P = S (1–14) | 20 |
| 2'-O-nonyl | >64 |
| 2'-t-butyldimethylsilyl | 8.0 |
| 2'-O-aminopropyl | 17.7 |
| 2'-O-allyl | 10 |
| Sequence studied CGA CAA TGC AAG' G'G'T (SEQ ID NO:8) (15 mer, positions 12,13,14 modified) | |
| natural | 2.5 |
| 3-deaza deoxy G | 1.0 |
| 3-deaza-3-nonyl deoxy G | 4.4 |
| 3-deaza-3-allyl deoxy G | 20+ |
| 3-deaza-3-benzyl deoxy G | 20 |

Example 138

In general the delta $T_m$ between the modified oligonucleotide and its unmodified analog is proportional to the number of modified residues. In a further test delta $T_m$ per modification were noted. Values of delta $T_m$ per modifications were averaged over all modified sequences studied and are listed in Table 5. Data is shown as average delta $T_m$ per modification compared to wild type DNA for both DNA targets and RNA targets. Further, specificity verse DNA targets is noted as an arbitrary score wherein 1 is specific and 4 is non-specific.

TABLE 5

BIOPHYSICAL EVALUATION OF OLIGONUCLEOTIDES

| Specificity Modification | Stability vs DNA Targets | Stability vs RNA Targets | Stability vs DNA Targets |
|---|---|---|---|
| Natural DNA | 0 | 0 | 1 |
| Natural RNA | +0.1 | +1.7 | 1 |
| phosphorothioate | −0.5 | −0.5 | 1+ |
| 2'-Chloro-2'-deoxy A | −3.2 | −5.2 | 3 |
| 3-deaza-2'-deoxy G | −3.3 | −2.9 | 5 |
| 2'-O-nonyl A | −2.5 | −2.2 | 4 |
| 2'-t-butyldimethyl-silyl A | −4.5 | | 3 |
| 2'-O-allyl A | −1.6 | −0.7 | 2 |
| 2'-O-benzyl A | −2.7 | −1.0 | 2 |
| 2'-O-propylamine | −0.9 | −0.3 | 3 |
| 2'-O-butylamine | −1.2 | −0.6 | |

Example 139

In further tests nucleases resistance was compared relative to that of phosphorothioate and phosphodiester. Using the protocols of example 137, the degradation curve for phosphodiester oligonucleotides were determined and rated as 5. For phosphodiester oligonucleotides degradation was about 50% at about 1 hour and complete at about 4 hours. Phosphorothioate oligonucleotides were rated as 1. For phosphorothioate oligonucleotides degradation was about 20% at about four hours and about 50% at about 20 hours. Oligonucleotides containing modifications were assigned values based upon visual comparison to the phosphodiester and phosphorothioate curves. These values are reported in Table 6.

TABLE 6

RELATIVE RESISTANCE TO FETAL CALF SERUM NUCELASES

| Modification | Position (#) | Relative Rate |
|---|---|---|
| Natural DNA | all | 5 |
| phosphorothioate | all | 1 |
| phosphodiester | all | 5 |
| 2'-Chloro-2'-deoxy A | | 5 |
| 2'-O-nonyl A | 3' (1) | 3 |
| | 3' (1) | 1 |
| 2't-butyldimethyl-sily A | 3' (3) | 1 |
| 2'-O-allyl A | 3' (1) | 3 |
| 2'-O-benzyl A | 3' (1) | 3 |
| 2'-O-propylamine | 3' (1) | 2 |
| 2'-O-Fluoro-2' deoxy A | 3' (3) | 5 |
| | internal | 5 |
| | all | 5 |
| 2'-O-methyl A | all | 1 |

Example 140

Utilizing the protocols of examples 135 and 138 oligonucleotides of the invention having novel nucleotides as prepared per certain of the above examples were tested for their DNA-DNA duplex stability or DNA-RNA duplex stability against DNA or RNA seqences. Hybridization analysis based upon the $T_m$, the delta $T_m$ and the delta $T_m$ per modification were determined. The results of these tests are shown in Table 6 below.

The test sequences represent various sequences chosen to demonstrate specific activity in known pathogens or test sequences. The JM-12 is a synthetic sequence that is self complementary. Since it is self complementary each modification is expressed twice, once for each occurrence in the complementary sequences. The HSV-21 is a 21 mer sequence from herpes virus. The G capped PAP is sequence from papiloma virus having a C nucleotide at the 3' end that is the linking nucleotide during synthesis. This is followed by three capping G nucleotides. This capping is specifically added to enhance the nuclease resistance of the sequence. The XY sequence is particularly useful for the determination of steric hindrance of the Watson-Crick binding between complementary strands. The 5LO is a 16 mer from the mRNA of human 5-lipoxygenose.

For these tests the "2 Chloro dA" nucleotide was prepared as per the synthetic chemical sequence terminating with example 124 above and the "2 propyl imidazoyl dG" nucleotide as per the synthetic chemical sequence terminating with Example 107 above.

TABLE 7

DUPLEX STABILITY

| positions of modification | $T_m$ | delta $T_m$ | delta $T_m$/mod |
|---|---|---|---|
| DNA-RNA DUPLEX STABILITY Complementary strand - YX: GGA CCG GAA GGT ACG AG (SEQ ID NO:9) Test nucleotide - 2 Chloro dA | | | |
| natural | 58.8 | — | — |
| 3 8 9 13 16 | 35.0 | −24 | −5.2 |

TABLE 7-continued

DUPLEX STABILITY

| positions of modification | $T_m$ | delta $T_m$ | delta $T_m$/mod |
|---|---|---|---|
| Complementary strand- HSV-21: ACC GAG GAT CAT GTC GTA CGC (SEQ ID NO: 10) Test nucleotide - 2 Chloro dA | | | |
| natural | 64.3 | — | — |
| 1 5 8 11 18 | 54.5 | −9.8 | −2.0 |
| Complementary strand - HSV-21 GCC GAG GTC CAT GTC GTA CGC (SEQ ID NO: 11) Test nucleotide - 2 proply imidazoyl dG | | | |
| natural | 69.1 | — | — |
| 13 | 69.0 | 0.4 | 0.4 |
| 4 13 20 | 70.3 | +1.3 | +0.2 |
| 1 4 6 7 13 16 20 | 70.4 | +1.3 | +0.2 |
| Complementary strand- HSV-21: ACC GAG GTC CAT GTC GTA CGC (SEQ ID NO: 12) Test nucleotide - 2'-fluor-2'-deoxy A | | | |
| DNA (terminal A C mismatch) | 67.5 | — | — |
| 1 5 11 18 (terminal A C mismatch) | 70.0 | +2.5 | +0.6 |
| Complementary strand- HSV-21: ACC GAG GAT CAT GTC GTA CGC (SEQ ID NO:10) Test nucleotide - 2'-fluoro-2'-deoxy A | | | |
| DNA | 63.1 | — | — |
| 1 5 8 11 18 | 67.7 | +4.5 | +0.9 |
| Complementary strand - PAP: CGA CTA TGC AAG TAC (SEQ ID NO: 3) Test nucleotide - 2'-fluor-2'-deoxy A | | | |
| natural | 45.1 | — | — |
| 3 6 10 11 14 | 53.0 | +7.9 | +1.6 |
| 3 5 6 7 10 11 13 14 | 58.9 | +13.8 | +1.7 |
| 1 3 4 5 6 7 9 10 13 14 | 65.2 | +20.1 | +1.8 |
| Complementary strand - PAP: CGA CTA TGC AAG TAC (SEQ ID NO: 3) Test nucleotide - 2'-fluor-2'-deoxy A | | | |
| all PS | 33.9 | — | — |
| all PS with 2'-fluor in 1 3 4 5 6 7 9 10 11 13 14 | 60.9 | +27.0 | +2.5 |
| Complementary strand - XY: GGA CCG GAA GGT ACG AG (SEQ ID NO: 9) Test nucleotide - 2'-fluor-2'-deoxy A | | | |
| natural | 56.9 | — | — |
| 3 8 9 13 17 | 65.9 | +9.0 | +1.8 |
| Complementary strand - XY: CTC GTA CCT TCC GGTC C (SEQ ID NO: 13) Test nucleotide - 2'-fluor-2'-deoxy A | | | |
| natural | 65.0 | — | — |
| 2 5 9 10 15 | 68.5 | +3.5 | +0.7 |
| 1 2 3 5 6 7 8 9 10 12 15 16 | 75.5 | +10.4 | +0.8 |
| Complementary strand - 5LO: TCC AGG TGT CCG CAT C (SEQ ID NO: 14) Test nucleotide - 2'-fluor-2'-deoxy A | | | |
| natural | 62.0 | — | — |
| 1 7 9 15 | 64.7 | +2.8 | +0.7 |
| DNA-DNA DUPLEX STABILITY Complementary strand- HSV-21: GCC GAG GTC CAT GTC GTA CGC (SEQ ID NO: 12) Test nucleotide - 2 proply imidazoyl dG | | | |
| natural | 69.7 | — | — |
| 13 | 72.3 | 2.6 | 2.6 |
| 4 13 20 | 75.8 | 6.1 | 2.0 |
| 1 4 6 7 13 16 20 | 83.3 | +13.6 | +1.9 |
| Complementary strand - JM-12: GCC TGA TCA GGC (SEQ ID NO: 15) Test nucleotide - 2 proply imidazoyl dG | | | |
| natural | 50.8 | — | — |
| 5 | 63.4 | +12.6 | +6.3 |
| Complementary strand - G capped PAP: CGA CTA TGC AAG GGC (SEQ ID NO: 16) Test nucleotide - 2 proply imidazoyl dG | | | |
| natural | 56.5 | — | — |
| 12 13 14 | 64.9 | +8.4 | +2.8 |
| Complementary strand - XY: CTC GTA CCA TTC CGG TCC (SEQ ID NO: 5) Test nucleotide - 2'-fluor-2'-deoxy A | | | |
| natural | 62.6 | — | — |
| 9 | 60.6 | −2.0 | −2.0 |
| Complementary strand - XY: GGA CCG GAA GGT ACG AG (SEQ ID NO: 9) Test nucleotide - 2'-fluor-2'-deoxy A | | | |
| natural | 60.6 | — | — |
| 3 8 9 13 16 | 61.0 | +0.4 | +0.1 |
| Complementary strand - XY: CTC GTA CCT TTC GGTC C (SEQ ID NO: 17) Test nucleotide - 2'-fluor-2'-deoxy A | | | |
| natural | 60.6 | — | — |
| 2 5 9 10 15 | 55.9 | −3.9 | −0.8 |
| Complementary strand - XY: CTC GTA CCT TTC GGT TCC (SEQ ID NO: 18) Test nucleotide - 2'-fluor-2'-deoxy A | | | |
| natural | 61.7 | — | — |
| 9 | 60.7 | −1.0 | −1.0 |
| Complementary strand- HSV-21: ACC GAG GTC CAT GTC GTA CGC (SEQ ID NO: 18) Test nucleotide - 2'-fluor-2'-deoxy A | | | |
| natural | 68.9 | — | — |
| 1 5 11 18 | 67.0 | −1.8 | −0.5 |
| Complementary strand- HSV-21: ACC GAG GAT CAT GTC GTA CGC (SEQ ID NO:10) Test nucleotide - 2'-fluor-2'-deoxy A | | | |
| natural | 66.1 | — | — |
| 1 5 8 11 18 | 66.4 | +0.3 | +0.1 |
| Complementary strand - PAP: CGA CTA TGC AAG TAC (SEQ ID NO:3) Test nucleotide - 2'-fluor-2'-deoxy A | | | |
| natural | 53.2 | — | — |
| 3 6 10 11 14 | 53.0 | −0.2 | 0.0 |
| Complementary strand - PAP: CGA CTA TGC AAG TAC (SEQ ID NO:3) Test nucleotide - 2'-fluor-2'-deoxy A | | | |
| natural | 52.3 | — | — |
| 5 7 13 | 52.1 | −0.2 | −0.1 |
| 3 5 6 7 10 11 13 14 | 55.4 | +3.2 | +0.5 |
| Complementary strand - A capped PAP: CGA CTA TGC AAG TAC (SEQ ID NO:3) Test nucleotide - 2'-fluor-2'-deoxy A | | | |
| natural | 50.4 | — | — |
| 12 13 14 | 43.6 | −6.8 | −2.3 |
| Complementary strand - A capped PAP: CGA CTA TGC AAG TAC (SEQ ID NO:3) Test nucleotide - 2'-fluor-2'-deoxy A | | | |
| all PS | 43.2 | — | — |
| all Ps with 2'-fluoro in 12 13 14 | 47.3 | +4.1 | +1.4 |
| Complementary strand- PAP-mod: CGA CTA TGC AAG TAC AAA T (SEQ ID NO:19) | | | |

TABLE 7-continued

DUPLEX STABILITY

| positions of modification | $T_m$ | delta $T_m$ | delta $T_m$/mod |
|---|---|---|---|
| Test nucleotide - 2'-fluor-2'-deoxy A | | | |
| natural | 56.5 | — | — |
| 3 6 10 11 14 16 17 18 | 56.0 | −0.5 | −0.1 |
| Complementary strand - 5LO: TCC AGG TGT CCG CAT C (SEQ ID NO:14) | | | |
| Test nucleotide - 2'-fluor-2'-deoxy A | | | |
| natural | 62.5 | — | — |
| 1 7 9 15 | 61.2 | −1.3 | −0.3 |

Example 141

Compositions for modulating the activity of messenger RNA coding for production of the protein 5-lipoxygenase are constructed as per this example and others that follow. The sequence CGUUCCAGUGACUUC (SEQ ID NO: 20) appears in the 5-lipoxygenase mRNA beginning at nucleotide 1065, defined by counting the initiation of translation "A" as zero. Other regions may also be selected which are likely to lead to effective antisense agents. For the above des-cribed region, a target antisense oligonucleotide (GCAAGGTCACTGAAG) (SEQ ID NO:1) directed to the 5-lipoxygenase mRNA may be constructed by standard solid state techniques leading to an effective composition in accordance with this invention. The 5LO sequence 5'-GAA GTC ACT GGA ACG-3' (SEQ ID NO:21) containing specific adenines replaced by 2-imidazolyl-ethyl amino-2-deoxyadenine can be prepared as per examples 109 to 114 from 2-chloro-2'-deoxyadenosine (5.72 g, 20 mmol), *Journal of the American Chemical Society* Vol. 106, p. 6379 (1984). Appropriate amounts of this material are dissolved in dry THF and employed in the automated, solid phase synthesis of the 5LO sequence 5'-GAA GTC ACT GGA ACG-3' (SEQ ID NO:21).

Modified sequences synthesized will be:
GaA GTC ACT GGA ACG (SEQ ID NO:21)
GAA GTC ACT GGA aCG (SEQ ID NO:21)
GaA GTC ACT GGA aCG (SEQ ID NO:21)
GAA GTC aCT GGA ACG (SEQ ID NO:21)
GAA GTC ACT GGa ACG (SEQ ID NO:21)
GaA GTC aCT GGA aCG (SEQ ID NO:21)
Gaa GTC ACT GGA ACG (SEQ ID NO:21)
GAA GTC ACT GGa aCG (SEQ ID NO:21) and
Gaa GTC aCT GGa aCG (SEQ ID NO:21)
Where a=2-(imidazol-4-yl-ethylamino)adenine

Example 142

Synthesis of the 5LO-sequence 5'-GAA GTC ACT GGA containing N2-imidazolylethylguanine (2-imida-zolylamino hypoxanthine) at specific guanine positions is performed as per examples 101 to 108 substituting 1-(2-aminoethy) imidazol for 1-(3-aminopropyl)-imidazol. Appropriate amounts of this material are dissolved in dry THF and employed in the automated, synthesis of the 5LO 5'-sequence 5'-GAA GTC ACT GGA ACG-3'(SEQ ID NO:21).

Modified sequences synthesized will be:
gAA GTC ACT GGA ACG (SEQ ID NO:21)
GAA GTC ACT GGA ACg (SEQ ID NO:21)
GAA gTC ACT GGA ACG (SEQ ID NO:21)
GAA GTC ACT gGA ACG (SEQ ID NO:21)
GAA GTC ACT GgA ACG (SEQ ID NO:21)
gAA GTC ACT GGA ACg (SEQ ID NO:21)
gAA gTC ACT GGA ACg (SEQ ID NO:21) and
gAA gTC ACT ggA ACg (SEQ ID NO:21)
Where g=N2-(imidazolylethyl)guanine((2-imidazol-4-ylethylamino) hypoxanthine)

Example 143

Synthesis of 5LO sequence 5'-GAA GTC ACT GGA ACG-3'SEQ ID NO: 21 containing 2'-deoxy-2'-(imidazol-4-ylpropyl)adenine at specific positions is performed. A solution of 3',5'-O-(tetraisopropyl disiloxane-1,3-diyl)-9-β-D-arabinofuranosyladenine (10.2 g, 20 mmol) in 200 ml of dry pyridine is cooled in an ice bath and treated with trimethylchlorosilane (6 ml). After 0.5 hr, benzoyl chloride (6 ml) is added and the ice bath is removed. The reaction is chilled after two hr at ambient temperature and treated with 20 ml of cold water followed after 15 min with 20 ml of concentrated ammonia hydroxide. The reaction is evaporated under reduced pressure to an oil which is purified by silica gel chromatography to afford nine g of the 3',5',N6 blocked nucleoside. This material is dissolved in dry acetonitrile (200 ml) and dry DMF (50 ml), chilled in an ice bath, and treated with sodium hydride (400 mg) followed 30 min later with trifluoro-methylsulfonic acid anhydride (5 g) in dry acetonitrile (50 ml) added dropwise. The reaction is evaporated under reduced pressure. The residue is dissolved in ethyl acetate, washed with water, and dried with $MgSO_4$. Removal of the solvent under reduced pressure provides the 2'-trifluoro sulfonate as a hard foam. A sample of this material (4 g, 5.5 mmol) is dissolved in dry ethyl acetate (100 ml) and diisopropylethylamine (800 mg), cooled in an ice bath and treated with 1-(4-imidazolyl)-3-hydroxy-n-propane (750 mg). After two hr at ambient temperature, the reaction is washed with 50 ml of cold water and dried with $MgSO_4$. Removal of the solvent under reduced pressure provides the 2'-(imidazolylpropoxy) adenosine blocked in the 3',5' and N6-positions. This material is dissolved in 50 ml of dry THF and treated with tetrabutylammonium fluoride (10 ml of 1 M in THF) at room temperature for two hr. The solvent is removed under reduced pressure and the residue, absorbed on silica gel, is chromatographed over silica gel, eluting with chloro-form/methanol mixtures. The 5'-DMT and 3'-cyanoethoxy-phosphoramidite of this material is prepared as per examples 107 and 108 above and appropriate quantities of this material is dissoloved in dry acetonitrile and utilized in the automated, solid phase synthesis of the 5LO sequence 5'-GAA GTC ACT GGA ACG.

Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
Where a=2'-O-(imidazol-4-yl-n-propyl)adenine

Example 144

Synthesis of 5LO sequence 5'-GAA GTC ACT GGA ACG-3'(SEQ ID NO:21) containing 2'-(imidazol-4-ylpropyl)thymidine at specific positions is described. A solution of 3',5'-O-(tetraisopropyldisiloxane-1,3-diyl)-9-β-D-arabinofuranosyl-thymine (9.7 g, 20 mmol) is dissolved in dry acetonitrile (200 ml) and dry DMF (50 ml), chilled in an ice bath, and treated with sodium hydride (400 mg) followed 30 min later with trifluoromethylsulfonic acid anhydride (5 g) in dry acetonitrile (50 ml) added dropwise. The reaction is evaporated under reduced pressure. The residue is dissolved in ethyl acetate, washed with water, and dried with MgSO$_4$. Removal of the solvent under reduced pressure provides the 2'-trifluoro sulfonate as a hard foam. A sample of this material (4 g, 5.5 mmol) is dissolved in dry ethyl acetate (100 ml) and diisopropyl ethylamine (800 mg), cooled in an ice bath and treated with 1-(imidazol-4-yl)-3-hydroxy-n-propane (750 mg). After two hr at ambient temperature, the reaction is washed with 50 ml of cold water and dried with MgSO$_4$. The material is further reacted as per examples 107 and 108 above to provide the 5'-DMT-3'cyanoethoxyphosphoramidite. Appropiate quantities of this material is dissoloved in dry acetonitrile and utilized in the automated, solid phase synthesis of the 5LO sequence 5'-GAA GTC ACT GGA ACG. (SEQ ID NO:21)
Modified sequences synthesized will be:
GAA GTC ACt GGA ACG (SEQ ID NO:21)
GAA GtC ACT GGA ACG (SEQ ID NO:21) and
GAA GtC ACt GGA ACG (SEQ ID NO:21)
Where t=2'-O-(imidazol-4-yl-n-propyl)thymine Example 145

Synthesis of the 5LO-sequence 5'-GAA GTC ACT GGA ACG (SEQ ID NO:21) containing 3-deaza-3-(imidazol-4-yl-propyl)guanine at specific positions is described. A solution of 5.2 g, 10 mmol, of 5-(cyanomethyl)-1-(2-deoxy-3,5-di-O-p-toluoyl-β-D-erythro-pentofuranosyl)imidazole-4-carboxylate, *Journal of Medicinal Chemistry*, Vol. 27, p. 1389 (1984), is dissolved in dry THF (100 ml) and treated with sodium hydride (840 mg) at room temperature. After evolution of hydrogen ceases, 4-(2-bromoethyl)imidazole hydrobromide (2.6 g), *Rec. Trav. Chim.*, Vol 89, p. 1189 (1970), is added and the solution stirred at ambient temperature for five hr. The reaction is evaporated to dryness. The residue is dissolved in ethyl acetate, washed with water and dried with MgSO$_4$. The residue obtained after filtration and solvent removal is dissolved in liquid ammonia and kept in a pressure vessel at ambient temperature for 24 hr and the heated to 100° C. for 1 hr. The ammonia is vented and the residue coevaporated with methanol two times. This material is dissolved in methanol, absorbed on silica gel and placed on a silica gel column. Elution with chloroform/methanol provides 2.0 g of 1-(2-deoxy-β-D-erythro-pentofuranosyl)-5-(1-cyano-3-[imidazol-4-yl]prop-1-yl)-4-carboxamide. This material is converted to the 5'-DMT-3'-cyanoethoxy isopropylphosphoramidite as per examples 107 and 108 above, affording a hard foam. Appropriate amounts of this maaterial is dissolved in dry acetonitrile and utilized in the automated, solid phase synthesis of the 5LO sequence 5'-GAA GTC ACT GGA ACG (SEQ ID NO:21).
Modified sequences synthesized will be:
gAA GTC ACT GGA Acg (SEQ ID NO:21)
gAA GTC ACT gGA Acg (SEQ ID NO:21)
gAA gTC ACT GGA Acg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT gGA ACg (SEQ ID NO:21)
Where g=3-deaza-3-(4-imidazolylethyl)guanine Example 146

Synthesis of the 5LO sequence 5'-GAA GTC ACT GGA ACG containing 7-(imidazol-4-yl-methyl)-7,8-dihydro-imidazo[4,5-c]pyrrolo[3,2-e]pyridin-4(5H)-one at specific sites is performed. A solution of methyl 1-(3,5-di-O-toluoyl-β-D-erythro-pentofuranosyl)-5-cyanomethyl-imidazole-4-carboxylate (10.34 g, 20 mmol), *Journal of Medicinal Chemistry*, Vol. 27, p. 1389 (1984), and dry acetonitrile is treated with sodium hydride (500 mg). After stirring at ambient for 30 min, the solution is treated with 1-bromo-3-(1-t-Boc-imidazol-4-yl-)-2-oxo ethylene ketal (7.24 g) and stirring is continued for 16 hr. The reaction is evaporated under reduced pressure and the residue is distributed between ethyl acetate and water. The solvent is dried and removed under reduced pressure. The residue is placed in a Parr pressure vessel with liquid ammonia. The reaction is carried out for eight hr at 80 C. cooled and vented. The residue is co-evaporated with methanol several times, dissolved in hot aqueous ethanol and adjusted to pH 4 with hydrochloric acid. After one hour the solution is selectively hydrogenated in the presence of Raney nickel. After one equivalent of hydrogen is taken up, the reaction is filtered and adjusted to pH 7. The solution is evaporated to dryness under reduced pressure. This material is absorbed on silica gel with the aid of methanol and chromatographed over silica gel, eluting with methanol/chloroform to afford 3.2 g of 1-(2-deoxy-β-D-erythro-pentofuranosyl)-7-(imidazol-4-yl-methyl)-7,8-dihydro-imidazo[4,5-c]-pyrrolo[3,2-e]pyridin-4(5H)-one. This material is converted to the 5'-DMT-3'-cyanoethoxyphosphoramidite-5,6-diisobutryl according to the procedures of examples 107 and 108 above and inserted into the 5LO-sequence 5'-GAA GTC ACT GGA ACG (SEQ ID NO:21) via automated, solid phase DNA synthesis.
Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
Where g will be 7-(imidazol-4-yl-methyl)-7,8-dihydroimidazo[4,5-c]pyrrolo [3,2-e]pyridin-4(5H)-one Example 147

Synthesis of the 5LO sequence 5'-GAA GTC ACT GGA ACG (SEQ ID NO:21) containing 8-(imidazol-4-yl-methyl)-7,8-dihydroimidazo[4,5-c]pyrrolo[3,2-e]pyridin-4 (5H)-one within the oligonucleotide is performed. A solution of methyl 1-(3,5-di-O-toluoyl-β-D-erythro-pentofuranosyl)-5-cyanomethylimidazole-4-carboxylate (10.34 g, 20 mmol) in dry acetonitrile is treated with sodium hydride (500 mg). After stirring at ambient temperature for 30 min, the solution is treated with 2-bromo-3-(1-t-Boc-imidazol-4-yl)-propanone ethylene ketal (7.24 g) and stirring is continued for 16 hr. The reaction is worked up and further reacted as described above to provide 1-(2-deoxy-β-D-erythropentofuranosyl)-8-(imidazol-4-yl-methyl)-7,8-dihydroimidazo-[4,5-c]pyrrolo[3,2-e]pyridin-4(5H)-one. This material is converted to the 5'-DMT-3-cyanoethoxy-phosphoramidite-5,6-di isobutryl according to examples 107 and 108 above and inserted into the 5LO-sequence 5'-GAA GTC ACT GGA ACG (SEQ ID NO:21) via automated, solid phase DNA synthesis.
Modified sequences synthesized will be:
gAA GTC ACT GGA Acg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)

gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACG (SEQ ID NO:21)
Where g=8-(imidazol-4-yl-methyl)-7,8-dihydro-imidazo[4,5-c]pyrrolo[3,2-e]pyridin-4(5H)-one

Example 148

Synthesis of the 5LO sequence 5'-GAA GTC ACT GGA ACG (SEQ ID NO:21) containing 5-(imidazol-4-yl-ethoxymethyl)imidazole-2(H)one 4-carboxamide within the sequence is performed. A mixture of ethyl 5-bromomethyl-2-oxo-imidazlole 4-carboxylate (5.4 g, 20 mmol), imidazol-4-yl-2-ethanol (2.3 g), dry acetonitrile (100 ml) is treated with sodium hydride (750 mg) and stirred for 5 hr at ambient tempera-ture. The solution is adjusted to approximately pH 7 with acetic acid and evaporated to dryness. Purification by chromatography provides the desired material in 30% yield. This material dissolved in dry pyridine (100 ml) and N-ethyl-diisopropyl amine (8 ml) is treated with diphenylaminocarbonyl chloride (5 ml). Stirring is continued for 5 hr. The solution is evaporated to dryness under reduced pressure and the residue is distributed between ethyl acetate and water. The organic layer is dried with magnesium sulfate and evaporated to dryness. Purification by silica gel chromatography afforded the bis(diphenylcarbamoyl) protected imidazole (3.5 g, 5 mmol). This is dissolved in dry acetonitrile (50 ml) and treated with sodium hydride (130 mg) after stirring at ambient temperature for 30 min, 3,5-di-O-(p-toluoyl)-α-D-erythro-pentofuransyl chloride is added. The mixture is stirred for 8 hr and filtered. The filtrate is evaporated to dryness and the filtered residue washed with water. The remaining residue is dissolved in ethyl acetate and combined with the filtrate residue. This material is purified by chromatography over silica gel to yield 4 g of blocked nucleoside. This is dissolved in methanol saturated at 20° C. with ammonia. The solution is allowed to stir at ambient temperature overnight. Evaporation under reduced pressure and subsequent silica gel chromatography provides the sugar deprotected nucleoside. This material is converted by procedures of examples 107 and 108 above into its 5'-DMT-3'-β-cyanoethylphosphoramidite which is inserted into the 5LO-sequence 5'-GAA GTC ACT GGA ACG (SEQ ID NO:21) via automated, solid phase DNA synthesis. Modified sequences synthesized will be:
gAA GTC ACT GGA Acg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
Where g=5-(imidazol-4-yl-ethoxymethyl)-imidazole-2(H)-one 4-carboxamide.

Example 149

Synthesis of the 5LO sequence 5'-GAA GTC ACT GGA ACG (SEQ ID NO:21) containing 4-amino-5-(imidazol-4-yl-ethoxymethyl)-imidazole-2(3H)one at specific sites is described. A mixture of 2,4-dibromo-5-nitroimidazole (5.4 g, 20 mmol), imidazol-4-yl-2-ethanol (2.3 g), dry acetonitrile (100 ml) is treated with sodium hydride (750 mg) and stirred for 5 hr at ambient temperature. The solution is adjusted to approximately pH 7 with acetic acid and evaporated to dryness. Purification by chromatography provides the desired material in 30% yield. This material dissolved in dry pyridine (100 ml) and N-ethyldiisopropyl amine (8 ml) is treated with diphenylaminocarbonyl chloride (5 ml). Stirring is continued for 5 hr. The solution is evaporated to dryness under reduced pressure and the residue distributed between ethyl acetate and water. The organic layer is dried with magnesium sulfate and evaporated to dryness. Purification by silica gel chromatography afforded the bis (diphenylcarbamoyl) protected imidazole (3.5 g, 5 mmol). This is dissolved in dry acetonitrile (50 ml) and treated with sodium hydride (130 mg) after stirring at ambient temperature for 30 min, 3,5-di-O-(p-toluoyl)-α-D-erythropentofuransyl chloride is added. The mixture is stirred for 8 hr and filtered. The filtrate is evaporated to dryness. The filtered residue is washed with water and the remaining residue is dissolved in ethyl acetate and combined with the filtrate residue. This material is purified by chromatography over silica gel to yield 4 g of blocked nucleoside. This is dissolved in methanol saturated at 20° C. with ammonia. The solution is allowed to stir at ambient temperature overnight. Evaporation under reduced pressure and subsequent silica gel chromatography provides the sugar deprotected nucleoside. This material is converted by procedures of examples 107 and 108 above into its 5'-DMT-3'-β-cyanoethylphosphoramidite which is inserted into the 5LO-sequence 5'-GAA GTC ACT GGA ACG (SEQ ID NO:21) via automated, solid phase DNA synthesis. Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g is 4-amino-5-(imidazol-4-yl-ethoxymethyl)-imidazole-2(H)-one.

Example 150

Synthesis of the 5LO sequence 5'-GAA GTC ACT GGA ACG (SEQ ID NO:21) containing 4-amino-5-(imidazol-4-yl-ethoxymethyl)-imida-zole at specific sites is described. A mixture of 2,4-dibromo-5-nitro imidazole (5.4 g, 20 mmol), 2-(1-benzylimidazol-4-yl)-ethanol, dry acetonitrile (100 ml) is treated with sodium hydride (750 mg) and stirred for 5 hr at ambient temperature. The solution is adjusted to approximately pH 7 with acetic acid and evaporated to dryness. Purification by chromatography provides the desired material in 30% yield. This is dissolved in dry acetonitrile (50 ml) and treated with sodium hydride (130 mg) after stirring at ambient temperature for 30 min, 3,5-di-O-(p-toluoyl)-α-D-erythro-pentofuransyl chloride is added. The mixture is stirred for 8 hr and filtered. The filtrate is evaporated to dryness. The filtered residue is washed with water and the remaining residue is dissolved in ethyl acetate and combined with the filtrate residue. This material is purified by chromatography over silica gel to yield 4 g of blocked nucleoside. This is dissolved in methanol saturated at 20° C. with ammonia. The solution is allowed to stir at ambient temperature overnight. Evaporation under reduced pressure and subsequent silica gel chromatography provides the sugar deprotected nucleoside. Catalytic reduction of this material with hydrogen provides 2-amino-1-(2-deoxy-β-D-erythropentofuranosyl)-5-(imidazol-4-yl-ethoxymethyl) imidazole. Transient benzoylation provides the 4-benzoylamino-5-(1-benzoylimidazol-4-yl-ethoxymethyl) derivative. This material is converted by procedures of examples 107 and 108 above into its 5'-DMT-3'-b- cyanoethylphosphoramidite which is inserted into the 5LO-sequence 5'-GAA GTC ACT GGA ACG (SEQ ID NO:21) via automated, solid phase DNA synthesis. Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g is 4-amino-5-(imidazol-4-yl-ethoxymethyl)-imidazole.

Example 151

Synthesis of the 5LO sequence 5'-GAA GTC ACT GGA ACG (SEQ ID NO:21) containing 5-(imidazol-4-yl-ethoxymethyl)imidazole-2(H)one at specific sites will be carried out. A mixture of 4-bromoimidazole-2(H)one (20 mmol), and diphenylaminocarbonyl chloride is treated with sodium hydride (750 mg) and stirred for 5 hr at ambient temperature. The solution is adjusted to approximately pH 7 with acetic acid and evaporated to dryness. Purification by chromatography provides the desired material in 30% yield. This is dissolved in dry acetonitrile (50 ml) and treated with sodium hydride (130 mg). After stirring at ambient temperature for 30 min, 3,5-di-O-(p-toluoyl)-α-D-erythropentofuransyl chloride is added. The mixture is stirred for 8 hr and filtered. The filtrate is then evaporated to dryness. The filtered residue is washed with water and the remaining residue dissoloved in ethyl acetate and combined with the filtrate residue. This material is purified by chromatography over silica gel to yield 4 g of blocked nucleoside. This is dissolved in methanol saturated at 20° C. with ammonia. The solution is allowed to stir at ambient temperature overnight. Evaporation under reduced pressure and subsequent silica gel chromatography provides the sugar deprotected nucleoside. This material is then hydroxymethylated in the 5-position. Hydrogenolysis of this material with hydrogen provides 1-(2-deoxy-β-D-erythropentofuranosyl)-5-hydroxymethylimidazole. Transient benzoylation provides the 4-benzoylamino-5-(1-benzoylimidazo-4-yl-ethoxymethyl) derivative. This material is converted by procedures of examples 107 and 108 above into its 5'-DMT-3'-β-cyanoethyl phosphoramidite which is inserted into the 5LO-sequence 5'-GAA GTC ACT GGA ACG (SEQ ID NO:21) via automated, solid phase DNA synthesis.
Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACg (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g=4-amino-5-(imidazol-4-yl-ethoxymethyl)-imidazole.

Example 152

Synthesis of the 5LO sequence 5'-GAA GTC ACT GGA ACG (SEQ ID NO:21) containing 2-amino-5-(imidazol-4-yl-ethoxymethyl)-imidazole at specific sites is described. A mixture of 4-bromo-2-nitroimidazole (20 mmol), acetonitrile (100 ml), and sodium hydride is stirred at 50° C. for 30 min, cooled and treated with 3,5-di-O-p-methyl benzoyl-α-D-erythropentofuranosyl chloride. The solution is stirred at ambient temperature for eight hours and filtered to remove sodium chloride. The filtrate is evaporated to dryness and purified by silica gel chromatography. This material is chloromethylated in the 5-position. Subsequent nucleophilic displacement with 2-(imidazol-4-yl) ethanol under basic catalysis provides the 5-(imidazol-4-yl-ethoxymethyl) derivative. Hydrogenolysis of the bromo atom and reduction of the group is accomplished by hydrogen and paladium on charcoal conditions. Transient benzoylation is used to protect the 5-position imidazole derivative. This material is converted by procedures of examples 107 and 108 above into its 5'-DMT-3'-b-cyano-ethylphosphoramidite which is inserted into the 5LO-sequence 5'-GAA GTC ACT GGA ACG (SEQ ID NO:21) via automated, solid phase DNA synthesis.
Modified sequences synthesized will be:
GaA GTC ACT GGA ACG (SEQ ID NO:21)
GaA GTC ACT GGA aCG (SEQ ID NO:21)
Gaa GTC ACT GGA ACG (SEQ ID NO:21)
GAA GTC ACT GGa aCG (SEQ ID NO:21)
GAA GTC aCT GGA ACG (SEQ ID NO:21)
GAA GTC ACT GGa ACG (SEQ ID NO:21)
GAa GTC ACT GGA ACG (SEQ ID NO:21)
Gaa GTC aCT GGA ACG (SEQ ID NO:21) and
Gaa GTC aCT GGa aCG (SEQ ID NO:21)
where a is 2-amino-5-(imidazol-4-yl-ethoxymethyl) imidazole.

Example 153

Synthesis of the 5LO sequence 5'-GAA GTC ACT GGA ACG (SEQ ID NO: 21) containing 1-(imidazol-4-yl-ethyl) thymin-6-yl at specific sites is described. A mixture of 3,5-di-O-p-methyl-benzoyl-α-D-erythropentofuranosyl chloride in aceto-nitrile is cooled to 0° C. and treated with 6-litho-1-(1-[benzoyl]-imidazol-4-yl-)ethyl-3-benzylthymine. The solution is allowed to warm to room temperature and after three hours at ambient temperature the mixture is evaporated to dryness under reduced pressure. Silica gel chromatography with choroform and methanol) afforded and material which is then debenzoylated with methanolic ammonia at room temperature overnight. Recrystallization from ethanol provides 6'-(2-deoxy-β-D-erythropentofuranosyl)-1-(imidazol-4-yl-ethyl)thymine. This material is converted by procedures of examples 107 and 108 above into its 5'-DMT-3'-β-cyanoethylisopropyl phosphoramidite which is inserted into the 5LO-sequence 5'-GAA GTC ACT GGA ACG (SEQ ID NO:21) via automated, solid phase DNA synthesis. Modified sequences synthesized will be:
GAA GtC ACt GGA ACG (SEQ ID NO:21)
GAA GTC ACt GGA ACG (SEQ ID NO:21) and
GAA GtC ACt GGA ACG (SEQ ID NO:21)
where t=1-(imidazol-4-yl-ethyl)thymin-6-yl.

Example 154

Synthesis of the 5LO sequence 5'-GAA GTC ACT GGA ACG (SEQ ID NO:21) containing 2-amino-4-oxo(3H)-8-(imidazol-4-yl-[propyl]quanazolin-7-oxy at specific sites is described. A solution of 2-isobutryamide-4-diphenyaminocarbonyloxy-8-[1-(benzoyl)imidazol-4-yl-propylquanazolin-7-ol is treated with sodium hydride at room temperature for 1 hour and then heated to 50° C. for 10 min. This solution is treated with 3,5-di-O-p-methylbenzoyl-α-D-erythropentofuranosyl chloride. The solution is stirred at ambient temperature for three hours and evaporated to dryness under reduced pressure. Silica gel chromatography (choroform/methanol) is followed by selectively debenzoylation with methanolic ammonia at room temperature overnight. Recrystallization from ethanol provides 7-(2-deoxy-β-D-erytheopentofuranosyl)-8-(1-[benzoyl]imidazol-4-yl-propyl)-2-isobutryamide-4-diphenyamino carbonyloxypropylquanazolin-7-yl. This material is converted by procedures of examples 107 and 108 above into its 5'-DMT-3'-b-cyanoethylphosphoramidite which is inserted into the 5LO-sequence 5'-GAA GTC ACT GGA ACG (SEQ ID NO:21) via automated, solid phase DNA synthesis.

Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g is 2-amino-4-oxo(3H)-8-(imidazol-4-yl-[propyl] quanazolin-7-oxy.

Example 155

Synthesis of 5LO sequence 5'-GAA GTC ACT GGA ACG -3'(SEQ ID NO: 21) containing 4-amino-7-(imidazol-4-yl-)-ethoxyimidazo[4,5-d]pyridazine at specific positions is described. A solution of 4,7-dichloroimidazo[4,5-d] pyridazine, *Journal of Organic Chemistry,* Vol. 23, p. 1534 (1958), in acetonitrile (100 ml) is treated with sodium hydride for one hour and then heated to 50° C. for 10 min. This solution is treated with 3,5-di-O-(methylbenzoyl)-α-D-erythro-pentofuranosyl chloride. After stirring at ambient temperature for three hours the mixture is filtered. The filtrate is evaporated to dryness under reduced pressure providing a foam which is chromatographed over silica gel. The pure product is aminated with liquid ammonia to provide 4-amino-7-chloro-1-(2-deoxy-β-D-erythro-pentofuranosyl)imidazo [4,5-d]-pyridazine. Recrystallization of this material from ethanol/water provides pure deblocked nucleoside. This material is dissolved in DMF and treated with the disodium salt of 2-(imidazol-4-yl) ethanol. The solution is heated at 100° C. for one hour and then evaporated to dryness under reduced pressure. The residue is recrystallized from water. After drying at 100° C. (0.1 torr) for 2 hours, the material is transiently benzoylated on the 4-amino and 7-position imdazole ring as previously described. M. J. Gait, *Oligonucleotide Synthesis,* (IRL Press 1985). This material is converted by procedures of examples 107 and 108 above into its 5'-DMT-3'-β-cyanoethyl phosphoramidite which is inserted into the 5LO-sequence 5'-GAA GTC ACT GGA ACG (SEQ ID NO:21) via automated, solid phase DNA synthesis.

Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 4-amino-7-(imidazol-4-yl-)-ethoxyimidazo[4,5-d]pyridazine.

Example 156

Synthesis of 5LO sequence 5'-GAA GTC ACT GGA ACG-3'(SEQ ID NO:21) containing 2'-deoxy-2'-(imidazol-4-yl-)-ethoxyadenosine at specific positions is described. A solution of 3',5'-(1,1,3,3-tetraisopropyldisiloxanyl)-9-(β-D-arabino-furanosy) adenine in pyridine is transiently benzoylated by subquent treatment with chlorotrimethylsilane, benzoyl chloride, and methanolic ammonia. The resulting solution is evaporated to dryness and recrystallized from ethanol. The pure product, dissolved in dry acetonitrile, is treated with trifluoromethylsulfonic acid anhydride and sodium hydride at 0° C. The solution is stirred at 0° C. for one hour and then is allowed to warm to ambient temperature (one hour). The solution is evaporated to dryness and purified by silca gel chromatography (methylene chloride/methanol). This material, N6-benzoyl-3',5'-(1,1,3,3-tetraisopropyldisiloxanyl)-2'-trifluoromethylsulfonyl-9-(β-D-arabinofuranosy)adenine, serves as the starting material for the synthesis of adenosines substituted in the 2'-position with a variety of functional groups and tethered functional groups. The β-D-arabinofuranosyl derivatives of guanine, cytosine, and thymine (Aldrich Chemical Co.) (as well as analog bases) protected such as by the N2-isobutryl, and N6-benzoyl, respectively, by conventional procedures can be 2'-modified as just described. The 2'-modified ribonucleotides can be inserted into sequence-specific oligonucleotides as of examples 107 and 108 above. A solution of N6-benzoyl-3',5'-(1,1,3,3-tetraisopropyl disiloxanyl)-2'-trifluoromethylsulfonyl-9-(β-D-arabinofuranosy)adenine and acetonitrile is cooled to 0° C. and treated with the disodium salt of 2-(imidazol-4-yl)ethanol in acetonitrile. The suspension is allowed to warm to room temperature and stirred at ambient temperature for two hours. The suspension is neutralized with acetic acid, treated with tetrabutylammoniun fluoride for 5 hours at room temperature, and evaporated to dryness under reduced pressure. The residue is dissolved in pyridine and transiently benzoylated as described above. After removal of the solvents, the residue is purified by silica gel chromatography. The resulting N6-benzoyl-2'-deoxy-2'-(1-[benzoyl]imidazol-4-yletoxy) adenosine is converted by procedures described above into its 5'-DMT-3'-β-cyanoethylphosphoramidite which is inserted into the 5LO-sequence 5'-GAA GTC ACT GGA ACG via automated, solid phase DNA synthesis.

Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(imidazo-4-yl-)ethoxyadenosine.

Example 157

Synthesis of 5LO sequence 5'-GAA GTC ACT GGA ACG-3'(SEQ ID NO:21) containing 2'-deoxy-2'-(9-[3-chloro-6-methoxyacridinyl]amino-n-pentyloxy)adenosine at specific positions is described. A solution of N6-benzoyl-3',5'-(1,1,3,3-tetraisopropyldisiloxanyl)-2'-trifluoromethylsulfonyl-9-(β-D-arabinofuranosy)adenine, 3-chloro-6-methoxyacridinyl-9-amino-n-pentanol, and acetonitrile is cooled to 0° C. and treated with the sodium hydride. The solution is allowed to warm to room temperature, then stirred at ambient temperature for two hours, and treated with tetrabutylammonium fluoride for two hours. The solution is evaporated to dryness and the residue purified by silica gel chromatography. This material is converted by procedures of examples 107 and 108 above into its 5'-DMT-3'-β-cyanoethyldiisopropylphosphoramidite derivative which is inserted into the 5LO-sequence 5'-GAA GTC ACT GGA ACG (SEQ ID NO:21) via automated, solid phase DNA synthesis. Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(9-[3-chloro-6-methoxyacridinyl]amino-n-pentyloxy)adenosine.

Example 158

Synthesis of 5LO sequence 5'-GAA GTC ACT GGA ACG-3'(SEQ ID NO:21) containing 2'-deoxy-2'-(N1,N1,N2-trimethoxycarbonyl-N2-methylcarbamoylethoxy) ethylenediamine adenosine at specific positionsis described. A solution of N6-benzoyl-3',5'-(1,1,3,3-tetraisopropyldisiloxanyl)-2'-trifluoromethylsulfonyl-9-(β-D-arabinofuranosy)adenine and acetonitrile is cooled to 0° C. and treated with the sodium salt of (N1,N1,N2-trimethoxycarbonyl-N2-methylcarbamoyl-ethanol) ethylenediamine in acetonitrile. The solution is allowed to warm to room temperature, then stirred at ambient temperature for two hours, and treated with tetrabutyl ammonium fluoride for two hours. The solution is evaporated to dryness and the residue purified by silica gel chromatography. This material is converted by procedures of examples 107 and 108 above into its 5'-DMT-3'-β-cyanoethylphosphoramidite derivative which is inserted into the 5LO-sequence 5'-GAA GTC ACT GGA ACG (SEQ ID NO:21) via automated, solid phase DNA synthesis. Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(N1,N1,N2-trimethoxycarbonyl-N2methyl carbamoylethoxy)ethylenediamine adenosine.

Example 159

Synthesis of 5LO sequence 5'-GAA GTC ACT GGA ACG-3'(SEQ ID NO:21) containing 2'-deoxy-2'-nonanoxyadenosine at specific positions is performed. A solution of N6-benzoyl-3',5'-(1,1,3,3-tetraisopropyldisiloxanyl)-2-trifluoromethylsulfonyl-9-(β-D-arabinofuranosy)adenine and acetonitrile is cooled to 0° C. and treated with the sodium salt of nananol in acetonitrile. The solution is allowed to warm to room temperature, then stirred at ambient temperature for two hours, and treated with tetrabutylammonium fluoride for two hours. The solution is evaporated to dryness and the residue purified by silica gel chromatography. This material is converted by procedures of examples 107 and 108 above into its 5'-DMT-3'-b-cyanoethyldiisopropyl phosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-nonanoxyadenosine.

Example 160

Synthesis of 5LO sequence 5'-GAA GTC ACT GGA ACG-3' SEQ ID NO:21) containing 2'-deoxy-2'-dimethylamino-tris(ethylamino)adenosine at specific positions is described. A 0° C. solution of N6-benzoyl-3',5'-(1,1,3,3-tetraisopropyldisiloxanyl)-2'-trifluoromethylsulfonyl-9-(b-D-arabinofuranosy)adenine, dimethylaminotris (ethylamine), ethyl isopropylamine, and acetonitrile is allowed to warm to room temperature and stirred at ambient temperature for 3 hours and then treated with tetrabutylammonium fluoride for two hours. The solution is evaporated to dryness and the residue purified by silica gel chromatography. This material is converted by procedures of examples 107 and 108 above into its 5'-DMT-3'-β-cyanoethyl phosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-dimethylamino-tris(ethylamino)adenosine.

Example 161

Synthesis of 5LO sequence 5'-GAA GTC ACT GGA ACG-3' (SEQ ID NO:21) containing 2'-deoxy-2'-(methoxytris-ethoxy)adenosine at specific position is described. A 0° C. solution of N6-benzoyl-3',5'-(1,1,3,3-tetraisopropyldisiloxanyl)-2'-trifluoromethylsulfonyl-9-(β-D-arabinofuranosy)adenine, methoxybisethoxyethanol and acetonitrile is treated with sodium hydride and allowed to warm to room temperature, stirred at ambient temperature for 3 hours, and then treated with tetrabutylammonium fluoride for two hours. The solution is evaporated to dryness and the residue purified by silica gel chromatography. This material is converted by procedures of examples 107 and 108 above into its 5'-DMT-3'-b-cyanoethyldiisopropylphosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(methoxytris-ethoxy)adenosine.

Example 162

Synthesis of 5LO sequence 5'-GAA GTC ACT GGA ACG-3' (SEQ ID NO:21) containing 2'-deoxy-2'-(N1,N1,N2-trimethoxycarbonyl-N2-methyl carbamoylethoxy) ethylenediamine adenosine at specific positions is described. A solution of 2-chloro-2'-deoxyadenosine, *Journal of the American Chemical Society*, Vol. 106, p. 6379 (1984), DMF, and potassium thiomethylate is heated at 100° C. for one hour, cooled to room temperature and treated with meta-chloroperbenzoate. After stirring at room temperature for three hours the solution is evaporated to dryness under reduced pressure. The residue is subjected to silica gel chromatography purication. The resulting 2-methylsulfonyl-2'-deoxyadenosine is benzoylated via the transient method as of examples 107 and 108 above. The N6-benzoyl-2'-deoxy-2-methylsulfonyladenosine thus prepared serves as the starting material for the preparation of a variety of 2'-deoxyadenosine and 2'-deoxyguanosine substituted in the 2-position. A solution of N6-benzoyl-2'-deoxy-2-methylsulfonyladenosine in DMF is treated with a solution of the sodium salt of (N1,N1,N2-trimethoxycarbonyl-N2-methylcarbamoylethanol)ethylenediamine in acetonitrile. The solution is heated to 100° C. for 30 min and evaporated to dryness under reduced pressure. Recrystallization of the residue affords N6-benzoyl-2'-deoxyadenosine with the ethylenediamine derivative in the 2-position. This material is converted by procedures of examples 107 and 108 above into its 5'-DMT-3'-b-cyanoethylphosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(N1,N1,N2-trimethoxycarbonyl-N2 methyl carbamoylethoxy)ethylenediamine adenosine.

Example 163

Synthesis of 5LO sequence 5'-GAA GTC ACT GGA ACG-3' (SEQ ID NO:21) containing 2'-deoxy-2'-(9-[3-chloro-6-methoxyacridinyl]amino-n-pentylamino) adenosine at specific positions is performed. A solution of N6-benzoyl-2'-deoxy-2-methylsulfonyladenosine, ethyl diisopropylamine, 9-[3-chloro-6-methoxyacridinyl]amino-n-pentylamine, and DMF is heated to 100° C. for 30 min and evaporated to dryness under reduced pressure. Recrystallization of the residue affords N6-benzoyl-2'-doxyadenosine with the aminoacridine derivative in the 2-position. This material is converted by procedures of examples 107 and 108 above into its 5'-DMT-3'-β-cyanoethylphosphor-amidite derivative which is inserted into the 5LO-sequence 5'-GAA GTC ACT GGA ACG (SEQ ID NO:21) via automated, solid phase DNA synthesis. Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2-(9-[3-chloro-6-methoxyacridinyl] amino-n-pentylamino)adenosine.

Example 164

Synthesis of 5LO sequence 5'-GAA GTC ACT GGA ACG-3' (SEQ ID NO:21) containing 2-dimethylamino-tris (ethylamino)adenosine at specific positions is described. A solution of N6-benzoyl-2'-deoxy-2-methyl sulfonyladenosine, ethyl diisopropylamine, 2-dimethylamino-tris(ethylamine, and DMF is heated to 100° C. for 30 min and evaporated to dryness under reduced pressure. Recrystallization of the residue affords N6-benzoyl-2'-doxyadenosine with the polyamine derivative in the 2-position. This material is converted by procedures of examples 107 and 108 above into its 5'-DMT-3'-β-cyanoethyl diisopropylphosphoramidite derivative which is inserted into the 5LO-sequence 5'-GAA GTC ACT GGA ACG via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2-dimethylamino-tris(ethylamino)adenine.

Example 165

Synthesis of 5LO sequence 5'-GAA GTC ACT GGA ACG-3' (SEQ ID NO:21) containing 2-(methoxybisethoxyethylamino)adenine at specific positions is described. A solution of N6-benzoyl-2'-deoxy-2-methyl sulfonyladenosine, ethyl diisopropylamine, methoxybisethoxy ethylamine, and DMF is heated to 100° C. for 30 min and evaporated to dryness under reduced pressure. Recrystallization of the residue affords N6-benzoyl-2'-doxyadenosine with the ethyleneglycol derivative in the 2-position. This material is converted by procedures of examples 107 and 108 above into its 5'-DMT-3'-β-cyanoethyl phosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2-(methoxybisethoxyethylamino)adenine.

Example 166

Synthesis of 5LO sequence 5'-GAA GTC ACT GGA ACG-3' (SEQ ID NO:21) containing 2-octanoxyadenine at specific positions is described. A solution of N6-benzoyl-2'-deoxy-2-methyl-sulfonyladenosine, ethyl diisopropylamine, octanoylamine, and DMF is heated to 100° C. for 30 min and evaporated to dryness under reduced pressure. Recrystallization of the residue affords N6-benzoyl-2'-deoxyadenosine with the carbon chain in the 2-position. This material is converted by procedures of examples 107 and 108 above into its 5'-DMT-3'-β-cyanoethyldiisopropylphosphoramidite derivative which is inserted into the 5LO-sequence 5'-GAA GTC ACT GGA ACG (SEQ ID NO:21) via automated, solid phase DNA synthesis.

Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2-octanoylaminoadenine.

Example 167

Synthesis of 5LO sequence 5'-GAA GTC ACT GGA ACG-3' (SEQ ID NO:21) containing 2'-deoxy-6'-(imidazol-4-yl-ethoxy)carbocyclic guanosine at specific positions is described. A solution of 2'-deoxy-3',5'-di-O-benzyl-6'-a-hydroxy-N6-methoxyethoxy carbocyclic guanosine, *Journal of Chemical Society, Chemical Communications, London*, pp. 1083–1084 (1987), is isobutrylated by the transitent method (pyridine, chlorotrimethylsilane, then isobutryl chloride, then methanol/ammonia. This material is reacted with 2-(1-benzoyl imidazol-4-yl)ethanol, triphenylphosphine/DEAD, and acetonitrile at room temperature for three hours. The solution is evaporated to dryness under reduced pressure. The residue is recrystallized from ethanol providing product which is debenzylated and deblocked with palladium/charcoal, hydrogen, and hydrochloric acid to provide 2'-deoxy-6'-α-(imidazol-4-yl-ethoxy)-N2-isobutrylcarbocyclic guanosine. This material is converted by procedures of examples 107 and 108 above into its 5'-DMT-3'-β-cyanoethylphosphoramidite derivative which is inserted into the 5LO-sequence 5'-GAA GTC ACT GGA ACG (SEQ ID NO:21) via automated, solid phase DNA synthesis.

Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g is 2'-deoxy-6'-(imidazol-4-yl-ethoxy)carbocyclic guanosine.

Example 168

Synthesis of 5LO sequence 5'-GAA GTC ACT GGA ACG-3' (SEQ ID NO:21) containing 2'-deoxy-6'-α-(N1,N1,N2-trimethoxycarbonyl-N2-methylcarbamoylethoxy)ethylenediamine)carbocyclic guanosine at specific positions is described. A solution of 2'-deoxy-3',5'-di-O-benzyl-6'-α-hydroxy-N6-methoxyethoxy carbocyclic guanosine, *Journal of Chemical Society, Chemical Communications, London*, pp. 1083–1084 (1987), is isobutrylated by the transitent method pyridine/chlorotrimethylsilane, then isobutryl chloride, then methanol/ammonia. The purified material is reacted with N1,N1,N2-trimethoxycarbonyl-N2-methylcarbamoylethoxy)ethylenediamine diphenyldiazine, and acetonitrile at room temperature for three hours. The solution is evaporated to dryness under reduced pressure. The residue is recrystallized from ethanol providing product which is debenzylated and deblocked with palladium/charcoal, hydrogen, and hydrochloric acid to provide 2'-deoxy-6'-α-(N1,N1,N2-trimethoxycarbonyl-N2-methylcarbamoylethoxy)ethylenediamine)-N2-isobutrylcarbocyclic guanosine. This material is converted by procedures of examples 107 and 108 above into its 5'-DMT-3'-β-cyanoethylphosphoramidite derivative which is inserted into the 5LO-sequence 5'-GAA GTC ACT GGA ACG (SEQ ID NO:21) via automated, solid phase DNA synthesis.

Modified sequences synthesized will be:
gAA GTC ACT GGA ACg (SEQ ID NO:21)
gAA GTC ACT gGA ACg (SEQ ID NO:21)
gAA gTC ACT GGA ACg (SEQ ID NO:21)
GAA GTC ACT GGA ACg (SEQ ID NO:21)
GAA GTC ACT ggA ACG (SEQ ID NO:21)
GAA gTC ACT GGA ACG (SEQ ID NO:21)
gAA GTC ACT GGA ACG (SEQ ID NO:21)
GAA GTC ACT GgA ACG (SEQ ID NO:21)
GAA gTC ACT GGA ACG (SEQ ID NO:21) and
gAA gTC ACT ggA ACg (SEQ ID NO:21)
where g is 2'-deoxy-6'-α-(N1,N1,N2-trimethoxycarbonyl-N2-methylcarbamoylethoxy)ethylenediamine)carbocyclic guanosine.

Example 169

Synthesis of 5LO sequence 5'-GAA GTC ACT GGA ACG-3' (SEQ ID NO:21) containing 2'-deoxy-2'-(imidazo-4-yl)ethoxy-α-D-adenosine at specific positions was performed. The 3',5'-positions of N6-Benzoyl-α-adenosine are simultaneously protected with 1,3-dichloro-1,1,3,3-tetraisopropyldisiloxane according to the known procedure. *Nucleic Acid Chemistry, Improved and New Synthetic Procedures, Methods, and Techniques*, Part 3, page 229 (1986). The 2'-hydroxy group is coupled with (1-benzoylimidazol-4-yl)ethanol with triphenylphosphine/DEAD according to the Mitsunobu procedure. Synthesis 1 (1981). The purified product is silyl deprotected with tetrabutylammonium fluoride and the resulting nucleoside is converted by procedures of examples 107 and 108 above into its 5'-DMT-3'-β-cyanoethylphosphoramidite derivative which is inserted into the 5LO-sequence 5'-GAA GTC ACT GGA ACG (SEQ ID NO:21) via automated, solid phase DNA synthesis.

Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(imidazo-4-yl)ethoxy-α-D-adenosine.

Example 170

Synthesis of 5LO sequence 5'-GAA GTC ACT GGA ACG-3' containing 2'-deoxy-2'-(N1,N1,N2-trimethoxycarbonyl-N2-methylcarbamoylethoxyethylenediamine)-α-D-adenosine at specific positions was performed. A solution of N6-benzoyl-3',5'-(1,1,3,3-tetraisopropyldisiloxanyl)-2'-trifluoromethylsulfonyl-9-(7-α-D-arabinofuranosy)adenine is coupled with (N1,N1,N2-trimethoxy carbonyl-N2-methylcarbamoylethanol)ethylenediamine with according to the Mitsunobu procedure. This material is deprotected with fluoride ion as of examples 107 and 108 above. The resultant material is converted by procedures described above into its 5'-DMT-3'-β-cyanoethyldiisopropylphosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(N1,N1,N2-trimethoxycarbonyl-N2-methylcarbamoylethoxyethylenediamine)-α-D-adenosine.

Example 171

Synthesis of 5LO sequence 5'-GAA GTC ACT GGA ACG-3' (SEQ ID NO:21) containing 2'-deoxy-2'-(9-[3-chloro-6-methoxyacridinyl]amino-n-pentyloxy-α-D-erythropentofuranosyl)adenine at specific positions is performed. A solution of N6-benzoyl-3',5'-(1,1,3,3-tetraisopropyldisiloxanyl)-2'-trifluoromethylsulfonyl-9-(β-D-arabinofuranosy)adenine is coupled with chloro-6-methoxyacridinyl-9-amino-n-pentanol according to the Mitsunobu procedure. The disilyl protection group is removed with fluoride ion and the resulting material is converted by procedures of examples 107 and 108 above into its 5'-DMT-3'-β-cyanoethyldiisopropylphosphoramidite derivative which is inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-(9-[3-chloro-6-methoxyacridinyl] amino-n-pentyloxy)adenosine.

Example 172

Synthesis of 5LO sequence 5'-GAA GTC ACT GGA ACG-3' (SEQ ID NO:21) containing 2'-deoxy-2'-[dimethylamino-bis(ethylamino)ethoxy]-α-D-adenosine at specific positions was performed. A solution of N6-benzoyl-3',5'-(1,1,3,3-tetraisopropyldisiloxanyl)-2'-trifluoromethylsulfonyl-9-(-β-D-arabinofuranosy)adenine is coupled with dimethylamino-bis(ethylamino)ethanol] according to the Mitsunobu procedure. The disilyl protection group is removed with fluoride ion and the resulting material is converted by procedures of examples 107 and 108 above into its 5'-DMT-3'-β-cyanoethylphosphoramidite derivative which was inserted into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 2'-deoxy-2'-[dimethylamino-bis(ethylamino) ethoxy]-α-D-adenosine.

Example 173

Synthesis of 5LO sequence 5'-GAA GTC ACT GGA ACG-3' (SEQ ID NO:21) containing 1'-(imidazo-4-yl) ethoxymethyladenosine at specific positions was performed. Psicofuranine, *Carbohydr. Res.*, Vol. 44, p. 112 (1975) is N6-benzoylated via the transient procedure as set forth by R. A. Jones in *Oligonucleotide Synthesis—A Practical Approach*, M. J. Gait, Ed., (IRL Press, Washington, DC, 1985) and subsequently the 3',5'-hydroxyls groups are simultaneously protected with 1,3-dichloro-1,1,3,3-tetraisopropyldisiloxane according to a known procedure. *Nucleic Acid Chemistry, Improved and New Synthetic Procedures, Methods, and Techniques*, Part 3, page 229, (1986). The 1'-hydroxymethyl group is treated with triphenylmethyl chloride in pyridine to afford protection of the primary alcohol. 2'-Deoxygenation is performed as described by M. J. Robins, et al, in *J. Am. Chem. Soc.*, Vol. 105, p. 4059 (1983). The resulting 2'-deoxy nucleoside is selectively detritylated with dilute trifluoroacetic acid. The 1'-hydroxymethyl group is coupled with 1-(benzoyl-imidazo-4-yl)ethanol according to the Mitsunobu conditions. Removal of the silyl protecting group and subsequent conversion of the resulting nucleoside to the 5'-DMT and the 3'-cyanoethyldiisopropylphosphite according to the procedures of examples 107 and 108 will afford monomers suitable for insertion into the 5LO-sequence 5'-GAA GTC ACT GGA ACG (SEQ ID NO:21) via automated, solid phase DNA synthesis.
Modified sequences synthesized will be:
GAa GTC ACT GGA aCG (SEQ ID NO:21)
GaA GTC ACT GGA aCG (SEQ ID NO:21)
GaA GTC aCT GGA aCG (SEQ ID NO:21)
GAA GTC aCT GGA ACG (SEQ ID NO:21)
GAA GTC ACT GGA aCG (SEQ ID NO:21)
GaA GTC ACT GGA ACG (SEQ ID NO:21)
GAA GTC ACT GGa ACG (SEQ ID NO:21)
GAa GTC ACT GGA ACG (SEQ ID NO:21) and
Gaa GTC aCT GGa aCG (SEQ ID NO:21)
where a is 1'-(imidazo-4-yl)ethoxymethyladenosine.

Example 174

Synthesis of 5LO sequence 5'-GAA GTC ACT GGA ACG-3' (SEQ ID NO:21) containing 4'-(imidazo-4-yl) ethoxymethylthymine at specific positions was preformed. 4'-Hydroxymethyl-thymidine, *J. Org. Chem.*, Vol. 44, p. 1309 (1979) is selectively ',5' protected with the TIPS group and then converted to its 3'-THP derivative. This material is silyl deprotected with fluoride ion and subsequently selectively 5'-tritylated. The 3'-hydroxy group is coupled to 2-(1-benzoyl imidazo-4-yl)ethanol via the Mitsunobu reaction conditions. This material is treated with acid to remove the trityl and THP groups and subsequently converted, as of examples 107 and 108 above, into the 5'-DMT and 3'-b-cyanoethoxydiisopropylphosphor-amidite groups. This material is inserted into the 5LO-sequence 5'-GAA GTC ACT GGA ACG (SEQ ID NO:21) via automated, solid phase DNA synthesis.

Modified sequences synthesized will be:
GAA GtC ACT GGA ACG (SEQ ID NO:21)
GAA GTC ACt GGA ACG (SEQ ID NO:21) and GAA GtC ACt GGA ACG (SEQ ID NO:21)

where t=4'-(imidazo-4-yl)ethoxymethylthymine

What is claimed is:

1. A compound represented by one of the Formulas 3, 4, 5, 6 and 7:

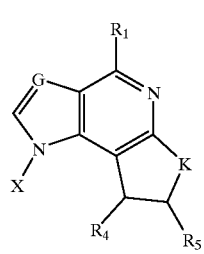

3

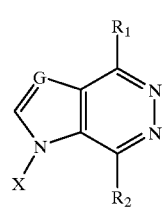

4

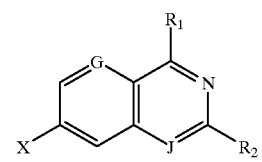

5

6

7

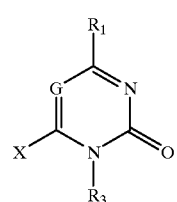

where:
  G and K are, independently, $CR_{3A}$ or N;
  J is N or $CR_{3B}$;
  $R_1$ is OH or $NH_2$;
  $R_2$, $R_{3A}$, $R_{3B}$, and $R_3$ are H, $NH_2$, lower alkyl, substituted lower alkyl, lower alkenyl, aralkyl, alkylamino, aralkylamino, substituted alkylamino, heterocycloalkyl, heterocycloalkylamino, aminoalkylamino, polyalkylamino, or a RNA cleaving moiety;
  $R_4$ and $R_5$ are H, OH, $NH_2$, lower alkyl, substituted lower alkyl, substituted amino, or a RNA cleaving moiety;
  $R_6$ and $R_7$ are H, OH, $NH_2$, SH, halogen, $C(O)NH_2$, $C(NH)NH_2$, $C(O)O$-alkyl, $C(S)NH_2$, CN, $C(NH)$NHOH, lower alkyl, substituted lower alkyl, substituted amino, or a RNA cleaving moiety;
  X is represented by one of the formulas:

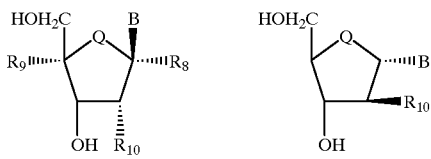

where:
  Q is O or $CHR_{11}$;
  $R_8$ and $R_9$ are H, lower alkyl, substituted lower alkyl, or a RNA cleaving moiety;
  $R_{10}$ is H, OH, lower alkyl, substituted lower alkyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2C\equiv CH$, $OC\equiv CH$, aralkyl, heteroaralkyl, heterocycloalkyl, aminoalkylamino, heterocycloalkyl, polyalkylamino, substituted silyl, or a RNA cleaving moiety;
  $R_{11}$ is H, OH lower alkyl, substituted lower alkyl, or a RNA cleaving moiety;
  provided that when said compound is represented by Formula 4 and when G is N and $R_{10}$ is H or OH, then $R_2$ is not H;
  further provided that when said compound is represented by Formula 6 and $R_6$ is H and $R_2$ is $NH_2$ and $R_7$ is $C(O)NH_2$, $C(S)NH_2$, $C(O)O$-alkyl, $C(NH)NH_2$ or $C(NH)NHOH$ then $R_{10}$ is not H or OH;
  further provided that when said compound is represented by Formula 6 and $R_6$ is H, OH or SH and $R_7$ is $C(O)O$-alkyl or $C(NH)NH_2$ and $R_2$ is $-CH_2CN$ then $R_{10}$ is not H or OH; and
  further provided that when said compound is represented by Formula 7 and $R_3$ is H and G is C, $R_{10}$ is not H or OH.

2. The compound of claim 1 wherein said RNA cleaving moiety comprises a portion reactive with said RNA.

3. The compound of claim 2 wherein the reactive portion comprises a basic functionality capable of catalyzing the hydrolysis of phosphodiester bonds in RNA.

4. The compound of claim 2 wherein said reactive portion comprises a coordination complex of a metal.

5. The compound of claim 2 wherein said reactive portion comprises a moiety capable of stabilizing the transition state formed in hydrolysis of a phosphodiester bond of RNA.

6. The compound of claim 5 wherein the moiety is capable of providing an octahedral coordination complex having two vacant sites.

7. The compound of claim 2 wherein said reactive portion comprises an acidic functionality capable of catalyzing the hydrolysis of phosphodiester bonds in RNA.

8. The compound of claim 2 wherein said reactive portion comprises a heterocycle.

9. The compound of claim 8 wherein the heterocycle is either a tetrazole or triazole.

10. The compound of claim 2 wherein said RNA cleaving moiety comprises an imidazole.

11. The compound of claim 2 wherein said reactive portion comprises an alkylating functionality.

12. The compound of claim 11 wherein the alkylating functionality is selected from the group consisting of sulfonyl halide, aziridines, nitrogen mustard compositions and Michael reaction accepting compositions.

13. The compound of claim 2 wherein said reactive portion comprises a functionality capable of forming free radicals.

14. The compound of claim 13 wherein the free radical functionality is selected from the group consisting of quinones, streptonigrins, mitomycins, coumarins, and active oxygen producing agents.

15. The compound of claim 1 wherein said RNA cleaving moiety further comprises a tether portion for attaching the reactive portion to the balance of the compound.

16. The compound of claim 1 wherein said RNA cleaving moiety comprises a nitrogen heterocycle.

17. The compound of claim 1 wherein said RNA cleaving moiety comprises an imidazole.

18. The compound of claim 1 wherein X is represented by the formula:

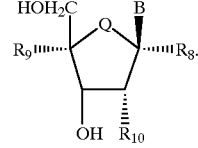

19. The compound of claim 1 wherein X is represented by the formula:

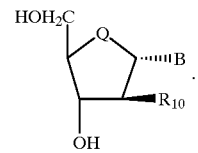

20. The compound of claim 1 represented by Formula 3.
21. The compound of claim 1 represented by Formula 4.
22. The compound of claim 1 represented by Formula 5.
23. The compound of claim 1 represented by Formula 6.
24. The compound of claim 1 represented by Formula 7.
25. A compound represented by one of the formulas:

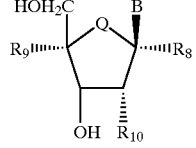 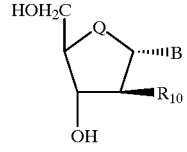

where:
  Q is O or $CHR_{11}$;
  $R_8$ and $R_9$ are H, lower alkyl, substituted lower alkyl, or a RNA cleaving moiety;
  $R_{10}$ is lower alkyl, substituted lower alkyl, F, Cl, Br, CN, $CF_3$, $OCF_3$, OCN, O-alkyl, S-alkyl, SOMe, $SO_2Me$, ONO$_2$, NO$_2$, N$_3$, NH$_2$, NH-alkyl, OCH$_2$CH=CH$_2$, OCH=CH$_2$, OCH$_2$C≡CH, OC≡CH, aralkyl, heteroaralkyl, heterocycloalkyl, polyalkylamino, substituted silyl, or a RNA cleaving moiety; and R$_{11}$ is H, OH lower alkyl, substituted lower alkyl, or a RNA cleaving moiety;

B is a naturally occurring or synthetic base moiety;

provided that when B is adenine, guanine, uracil, thymine, or cytosine, and R$_8$ and R$_9$ are H, then R$_{10}$ is not F, Cl, Br, NH$_2$, N$_3$, O-alkyl, S-alkyl, O-allyl or O-benzyl.

26. The compound of claim 25 wherein B is a pyrimidinyl-1 or purinyl-9 moiety.

27. The compound of claim 25 wherein B is a nucleoside or deoxynucleoside base.

28. The compound of claim 25 wherein B is adenine, guanine, uracil, thymine, cytosine or 5-methylcytosine.

29. A compound represented by Formula 2:

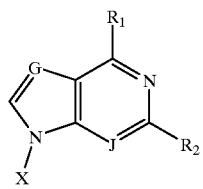

2 where:

G is CR$_3$;

J is N or CR$_3$;

R$_1$ is OH or NH$_2$;

R$_2$ and R$_3$ are H, NH$_2$, lower alkyl, substituted lower alkyl, lower alkenyl, aralkyl, alkylamino, aralkylamino, substituted alkylamino, heterocycloalkyl, heterocyclo-alkylamino, aminoalkylamino, hetrocycloalkylamino, polyalkylamino, a RNA cleaving moiety, a group for improving the pharmacokinetic properties of an oligonucleotide or a group for improving the pharmacodynamic properties of an oligonucleotide;

X is represented by one of the formulas:

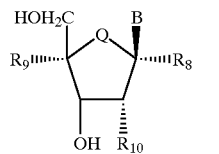 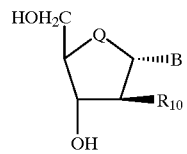

where:

Q is O or CHR$_{11}$;

R$_8$ and R$_9$ are H, lower alkyl, substituted lower alkyl, a RNA cleaving moiety, a group for improving the pharmacodynamic properties of an oligonucleotide or a group for improving the pharmacokinetic properties of an oligonucleotide;

R$_{10}$ is lower alkyl, substituted lower alkyl, F, Cl, Br, CN, CF$_3$, OCF$_3$, OCN, O-alkyl, S-alkyl, SOMe, SO$_2$Me, ONO$_2$, NO$_2$, N$_3$, NH$_2$, NH-alkyl, OCH$_2$CH=CH$_2$, OCH=CH$_2$, OCH$_2$C≡CH, OC≡CH, aralkyl, heteroaralkyl, heterocycloalkyl, amino-alkylamino, heterocycloalkyl, polyalkylamino, or substituted silyl; and R$_{11}$ is H, OH lower alkyl, substituted lower alkyl, a RNA cleaving moiety, a group for improving the pharmacokinetic properties of an oligonucleotide, or a group for improving the pharmacodynamic properties of an oligo-nucleotide;

provided that when R$_1$ is NH$_2$ and R$_2$ and R$_3$ are H, then J is not N.

* * * * *

```
                          SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
          (A) LENGTH: 15 bases
          (B) TYPE: nucleic acid
          (C) STRANDEDNESS: single
          (D) TOPOLOGY: linear (xi) SEQUENCE DESCRIPTION: SEQ ID NO:1:

GCAAGGTCAC TGAAG                                                15

(2) INFORMATION FOR SEQ ID NO:2:

(i) SEQUENCE CHARACTERISTICS:
          (A) LENGTH: 21 bases
          (B) TYPE: nucleic acid
          (C) STRANDEDNESS: single
          (D) TOPOLOGY: linear (xi) SEQUENCE DESCRIPTION: SEQ ID NO:2:

ACCGACGATC ATGTCGTACG C                                         21

(2) INFORMATION FOR SEQ ID NO:3:

(i) SEQUENCE CHARACTERISTICS:
          (A) LENGTH: 15 bases
          (B) TYPE: nucleic acid
          (C) STRANDEDNESS: single
          (D) TOPOLOGY: linear (xi) SEQUENCE DESCRIPTION: SEQ ID NO:3:

CGACTATGCA AGTAC                                                15

(2) INFORMATION FOR SEQ ID NO:4:

(i) SEQUENCE CHARACTERISTICS:
          (A) LENGTH: 15 bases
          (B) TYPE: nucleic acid
          (C) STRANDEDNESS: single
          (D) TOPOLOGY: linear (xi) SEQUENCE DESCRIPTION: SEQ ID NO:4:

CGACTATGCA AAAAC                                                15

(2) INFORMATION FOR SEQ ID NO:5:

(i) SEQUENCE CHARACTERISTICS:
          (A) LENGTH: 18 bases
          (B) TYPE: nucleic acid
          (C) STRANDEDNESS: single
          (D) TOPOLOGY: linear (xi) SEQUENCE DESCRIPTION: SEQ ID NO:5:

CTCGTACCAT TCCGGTCC                                             18

(2) INFORMATION FOR SEQ ID NO:6:
```

```
    (i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:6:

GGACCGGAAN GGTACGAG                                                        18

(2) INFORMATION FOR SEQ ID NO:7:

(i) SEQUENCE CHARACTERISTICS:
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:7:

GGACCGGAAN GGUACGAG                                                        18

(2) INFORMATION FOR SEQ ID NO:8:

(i) SEQUENCE CHARACTERISTICS:
        (A) LENGTH: 15 bases
        (B) TYPE: nucleic acid
        (C) STRANDEDNESS: single
        (D) TOPOLOGY: linear (xi) SEQUENCE DESCRIPTION: SEQ ID NO:8:

CGACAATGCA AGGGT                                                           15

(2) INFORMATION FOR SEQ ID NO:9:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:9:

GGACCGGAAG GTACGAG                                                         17

(2) INFORMATION FOR SEQ ID NO:10:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:10:

ACCGAGGATC ATGTCGTACG C                                                    21

(2) INFORMATION FOR SEQ ID NO:11:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:11:

GCCGAGCTCC ATGTCGTACG C                                                    21

(2) INFORMATION FOR SEQ ID NO:12:
```

(i) SEQUENCE CHARACTERISTICS:
    (A) LENGTH: 21 bases
    (B) TYPE: nucleic acid
    (C) STRANDEDNESS: single
    (D) TOPOLOGY: linear (xi) SEQUENCE DESCRIPTION: SEQ ID NO:12:

ACCGAGGTCC ATGTCGTACG C                                              21

(2) INFORMATION FOR SEQ ID NO:13:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:13:

CTCGTACCTT CCGGTCC                                                   17

(2) INFORMATION FOR SEQ ID NO:14:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:14:

TCCAGGTGTC CGCATC                                                    16

(2) INFORMATION FOR SEQ ID NO:15:

(i) SEQUENCE CHARACTERISTICS:
        (A) LENGTH: 12 bases
        (B) TYPE: nucleic acid
        (C) STRANDEDNESS: single
        (D) TOPOLOGY: linear (xi) SEQUENCE DESCRIPTION: SEQ ID NO:15:

GCCTGATCAG GC                                                        12

(2) INFORMATION FOR SEQ ID NO:16:

(i) SEQUENCE CHARACTERISTICS:
        (A) LENGTH: 15 bases
        (B) TYPE: nucleic acid
        (C) STRANDEDNESS: single
        (D) TOPOLOGY: linear (xi) SEQUENCE DESCRIPTION: SEQ ID NO:16:

CGACTATGCA AGGGC                                                     15

(2) INFORMATION FOR SEQ ID NO:17:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:17:

CTCGTACCTT TCGGTCC                                                   17

(2) INFORMATION FOR SEQ ID NO:18:

(i) SEQUENCE CHARACTERISTICS:

```
        (A) LENGTH: 18 bases
        (B) TYPE: nucleic acid
        (C) STRANDEDNESS: single
        (D) TOPOLOGY: linear (xi) SEQUENCE DESCRIPTION: SEQ ID NO:18:

CTCGTACCTT TCCGGTCC                                             18

(2) INFORMATION FOR SEQ ID NO:19:

(i) SEQUENCE CHARACTERISTICS:
        (A) LENGTH: 19 bases
        (B) TYPE: nucleic acid
        (C) STRANDEDNESS: single
        (D) TOPOLOGY: linear (xi) SEQUENCE DESCRIPTION: SEQ ID NO:19:

CGACTATGCA AGTACAAAT                                            19

(2) INFORMATION FOR SEQ ID NO:20:

(i) SEQUENCE CHARACTERISTICS:
        (A) LENGTH: 15 bases
        (B) TYPE: nucleic acid
        (C) STRANDEDNESS: single
        (D) TOPOLOGY: linear (xi) SEQUENCE DESCRIPTION: SEQ ID NO:20:

CGUUCCAGUG ACUUC                                                15

(2) INFORMATION FOR SEQ ID NO:21:

(i) SEQUENCE CHARACTERISTICS:
        (A) LENGTH: 15 bases
        (B) TYPE: nucleic acid
        (C) STRANDEDNESS: single
        (D) TOPOLOGY: linear (xi) SEQUENCE DESCRIPTION: SEQ ID NO:21:

GAAGTCACTG GAACG                                                15
```